US008546090B2

(12) United States Patent
Haigis et al.

(10) Patent No.: US 8,546,090 B2
(45) Date of Patent: Oct. 1, 2013

(54) SIRT4 ACTIVITIES

(71) Applicant: Massachusetts Institute of Technology, Cambridge, MA (US)

(72) Inventors: Marcia C. Haigis, Stoneham, MA (US); Leonard P. Guarente, Newton, MA (US)

(73) Assignee: Massachusetts Instittue of Technology, Cambridge, MA (US)

( * ) Notice: Subject to any disclaimer, the term of this patent is extended or adjusted under 35 U.S.C. 154(b) by 0 days.

(21) Appl. No.: 13/646,148

(22) Filed: Oct. 5, 2012

(65) Prior Publication Data

US 2013/0096179 A1    Apr. 18, 2013

Related U.S. Application Data

(63) Continuation of application No. 12/851,225, filed on Aug. 5, 2010, now abandoned, which is a continuation of application No. 11/409,170, filed on Apr. 21, 2006, now abandoned.

(60) Provisional application No. 60/673,565, filed on Apr. 21, 2005.

(51) Int. Cl.
*G01N 33/567* (2006.01)

(52) U.S. Cl.
USPC ........................................ 435/7.21; 435/455

(58) Field of Classification Search
USPC ................................. 435/7.21, 455
See application file for complete search history.

(56) References Cited

U.S. PATENT DOCUMENTS

| | | | |
|---|---|---|---|
| 4,873,191 A | 10/1989 | Wagner et al. |
| 5,010,175 A | 4/1991 | Rutter et al. |
| 5,093,246 A | 3/1992 | Chech et al. |
| 5,223,409 A | 6/1993 | Ladner et al. |
| 5,270,163 A | 12/1993 | Gold et al. |
| 5,270,170 A | 12/1993 | Schatz et al. |
| 5,283,173 A | 2/1994 | Fields et al. |
| 5,288,514 A | 2/1994 | Ellman |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,565,323 A | 10/1996 | Parker et al. |
| 5,569,588 A | 10/1996 | Ashby et al. |
| 5,593,853 A | 1/1997 | Chen et al. |
| 5,705,350 A | 1/1998 | Mudryj et al. |
| 5,744,300 A | 4/1998 | Linskens et al. |
| 5,817,782 A | 10/1998 | Jazwinski |
| 5,840,493 A | 11/1998 | Davis et al. |
| 5,874,210 A | 2/1999 | Guarente et al. |
| 5,919,618 A | 7/1999 | Guarente et al. |
| 5,965,543 A | 10/1999 | Campisi et al. |
| 5,998,131 A | 12/1999 | Barr et al. |
| 6,027,883 A | 2/2000 | Herrnstadt et al. |
| 6,146,831 A | 11/2000 | Davis et al. |
| 6,218,512 B1 | 4/2001 | Guarente et al. |
| 6,228,583 B1 | 5/2001 | Guarente et al. |
| 6,291,172 B1 | 9/2001 | Davis et al. |
| 6,787,300 B2 | 9/2004 | Guarente et al. |
| 6,835,563 B1 | 12/2004 | Lawn et al. |
| 6,884,597 B1 | 4/2005 | Taya et al. |
| 7,452,664 B2 | 11/2008 | Guarente et al. |
| 7,572,575 B2 | 8/2009 | Guarente et al. |
| 2003/0082668 A1 | 5/2003 | Tamai et al. |
| 2003/0124101 A1 | 7/2003 | Gu et al. |
| 2003/0207325 A1 | 11/2003 | Guarente et al. |
| 2003/0228607 A1 | 12/2003 | Wagner et al. |
| 2004/0091951 A1 | 5/2004 | Schultz |
| 2005/0136429 A1 | 6/2005 | Guarente et al. |
| 2005/0164969 A1 | 7/2005 | Guarente et al. |
| 2006/0252076 A1 | 11/2006 | Guarente et al. |
| 2007/0099830 A1 | 5/2007 | Guarente et al. |
| 2009/0155834 A1 | 6/2009 | Guarente et al. |
| 2010/0105036 A1 | 4/2010 | Guarente et al. |
| 2010/0240029 A1 | 9/2010 | Guarente et al. |
| 2011/0098190 A1 | 4/2011 | Guarente et al. |
| 2013/0071378 A1 | 3/2013 | Guarente et al. |

FOREIGN PATENT DOCUMENTS

| | | |
|---|---|---|
| WO | WO 91/19735 | 12/1991 |
| WO | WO 92/00091 | 1/1992 |
| WO | WO 93/20242 | 10/1993 |
| WO | WO 95/05459 | 2/1995 |
| WO | WO 96/05850 | 2/1996 |
| WO | WO 98/17823 | 4/1998 |
| WO | WO 99/10482 | 3/1999 |
| WO | WO 01/12851 A2 | 2/2001 |
| WO | WO 01/79842 A2 | 10/2001 |
| WO | WO 02/31111 A2 | 4/2002 |
| WO | WO 02/102981 A2 | 12/2002 |
| WO | WO 03/004621 A2 | 1/2003 |
| WO | WO 03/046207 A2 | 6/2003 |
| WO | WO 2005/002527 A2 | 1/2005 |
| WO | WO 2007/146023 A1 | 12/2007 |

OTHER PUBLICATIONS

Carson et al. "Pharmacogenomic identification of targets for adjuvant therapy with the topoisomerase poison camptothecin", Cancer Research, 2004, 64:2096-2104.*

Abedin, S.A., et al., "Environmental Sensing Capacity by VDR and Related Nuclear Receptors," *Anticancer Research*, 25(30): 2279 (2005).

Abraham, J., et al., "Posttranslational Modification of p53 Protein in Response to Ionizing Radiation Analyzed by Mass Spectrometry", *J. Mol. Biol.*, 295:853-864 (2000).

Abstracts of papers presented at the 2004 meeting on Molecular Genetics of Aging, Oct. 6-Oct. 10, 2004, abstract papers Nos. 21, 23, 47, 49, 56, 108 and 110. Cold Springs Harbor Laboratory, Cold Springs Harbor, New York.

Alfred, J. "Counting the Calories to Immortality", *Nat. Rev. Genet.*, 1(2):88, (Nov. 2000).

Allsopp, R.C., et al., "Telomere Length Predicts Replicative Capacity of Human Fibroblasts", *Proc. Natl. Acad. Sci. USA* 89:10114-10118 (Nov. 1992).

(Continued)

*Primary Examiner* — Bin Shen
(74) *Attorney, Agent, or Firm* — Hamilton, Brook, Smith & Reynolds, P.C.

(57) ABSTRACT

Methods of modulating insulin secretion and treating metabolic disorders by modulating the expression or activity of Sirt4 are provided.

13 Claims, 9 Drawing Sheets

(56) References Cited

OTHER PUBLICATIONS

Anderson, R.M., et al., "Manipulation of a Nuclear NAD⁺ Salvage Pathway Delays Aging Without Altering Steady-State NAD⁺ Levels," *Jour. of Biol. Chem.* 277(21):18881-18889 (May 2002).
Angello, J.C., et al., "Cell Enlargement: One Possible Mechanism Underlying Cellular Senescence", *J. Cell. Physiol.* 140:288-294 (Feb. 1989).
Angello, J.C., et al., "Proliferative Potential of Human Fibroblasts: An Inversive Dependence on Cell Size", *J. Cell. Physiol.* 132:125-130 (1987).
Aparicio, O.M., et al., "Modifiers of Position Effect are Share Between Telomeric and Silent Mating-Type Loci in *S. cerevisiae*," *Cell*, 66:1279-1287 (Sep. 1991).
Ashcroft, M., et al., "Stress Signals Utilize Multiple Pathways to Stabilize p53", *Mol. Cell Biol.*, 20(9):3224-3233 (May 2000).
Avalos, J.L., et al., "Structure of a Sir2 Enzyme Bound to an Acetylated p53 Peptide", *Molecular Cell*, 10(3):523-535 (Sep. 2002).
Avantaggiati, M.L., et al., "Recruitment of p300/CB0 in p53-Dependent Signal Pathways", *Cell*, 89:1175-1184 (Jun. 1997).
Bairoch, A., "Go Hunting in Sequence Databases but Watch Out for the Traps," *Trends in Genetics*, 12(10): 425-427 (Oct. 1996).
Brachmann, C., et al., "The SIR2 Gene Family, Conserved from Bacteria to Humans, Functions in Silencing, Cell Cyle Progression, and Chromosome Stability," *Genes & Development*, 9(23):2888-2902 (Oct. 1995).
Barak, Y., et al., "mdm2 Expression is Induced by6 Wild Type p53 Activity", *EMBO J.*, 12(2):461-468 (1993).
Bedalov, A., et al., "Identification of a Small Molecule Inhibitor of Sir2p", *Proc. Natl. Acad. Sci.*, 98:15113-15118 (Dec. 2001).
Bernstein, B.E., et al., "Genomewide Studies of Histone Deacetylase Function in Yeast", *Proc. Natl. Acad. Sci. USA*, 97:13708-13713 (Dec. 2000).
Bertrand, H., et al., "An Extrachromosomal Plasmid is the Etiological Precursor of kalDNA Insertion Sequences in the Mitochrondial Chromosome of Senescent Neurospora", *Cell*, 47:829-837 (Dec. 1986).
Bitterman, K.J., et al., "Inhibition of Silencing and Accelerated Aging by Nicotinamide, a Putative Negative Regulator of Yeast SIR2 and Human SIRT1," *Journal of Biological Chemistry*, 277(47): 45099-45107 (Nov. 2002).
Blander, G., et al., "SIRT1 Shows No Substrate Specifity in Vitro," *J. Biol. Chem.*, 280(11):9780-9785 (Mar. 2005).
Bork, P., "Powers and Pitfalls in Sequence Analysis: the 70% Hurdle," *Genome Research*, 10:398-400 (2000).
Borra, M.T., et al., "Conserved Enzymatic Production and Biological Effect of O-Acetyl-ADP-Ribose by Silent Information Regulator 2 -Like NAD¹ Dependent Dcacetylases," *Jour. Biol. Chem.* 277(15): 12632-12641 (Apr. 2002).
Bowie, J.U., et al, "Deciphering the Message in Protein Sequences: Tolerance to Amino Acid Substitutions," *Science*, 247:1306-1310 (Mar. 1990).
Braunstein, M., et al., "Efficient Transcriptional Silencing in *Saccharomyces cerevisiae* Requires a Heterochromatin Histone Acetylation Pattern," *Molecular and Cellular Biology*, 16(8):4349-4356 (Aug. 1996).
Braunstein, M., et al., "Transcriptional Silencing in Yeast Associated with Reduced Acetylation," *Genes & Development*, 7(4):592-604 (Feb. 1993).
Brenner, S.E., "Errors in Genome Annotation," *Trends in Genetics*, 15(4):132-133 (Apr. 1999).
Brower, M., et al., "Growth of cell lines and clinical specimens of human non-small cell lung cancer in a serum-free defined medium", *Cancer Research*, 46(2):798-806 (Feb. 1986).
Bryk, M., et al., "Transcriptional Silencing of Ty1 Elements in the *RDN1* Locus of Yeast," *Genes & Development*, 11:255-269 (1997).
Buckley, A.R., et al., "Alterations in *pim-1* and *c-myc* Expression Associated with Sodium Butyrate-Induced Growth Factor Dependency in Autonomous Rat Nb2 Lymphoma Cells", *Cell Growth Differ.*, 17: 1713-1721 (Dec. 1996).

Butler, L.M., et al., "Suberoylanilide Hydroxamic Acid, an Inhibitor of Histone Deacetylase Suppresses the Growth of Prostate Cancer Cells in Vitro and in Vivo", *Cancer Res.*, 60:5165-5170 (Sep. 2000).
Cabib, E., et al., "A Molecular Model for Morphogenesis: The Primary Septum of Yeast", *Curr. Top. Cell. Regul.*,8:1-32 (1974).
Campbell, D.A. and J.C. Bermak, "Phosphonate Ester Synthesis Using a Modified Mitsunobu Condensation," *J. Org. Chem.*, 59:658 (1994).
Campisi, J., "Aging, Chromatin, and Food Restriction-Connecting the Dots", *Science*, 289, pp. 2062-2063 (Sep. 2000).
Canman, C.E., et al., "Activation of the ATM Kinase by Ionizing Radiation and Phosphorylation of p53", *Science*, 281:1677-1679 (Sep. 1998).
Chao, C., et al., "p53 Transcriptional Activity is Essential for p53-Dependent Apoptosis Following DNA Damage", *EMBO J.*, 19:4967-4975 (Jul. 2000).
Chehab, N. H., et al., "Phosphorylation of Ser-20 Mediates Stabilization of Human p53 in Response to DNA Damage", *Proc. Nati. Acad. Sci. USA*, 96:13777-13782 (Nov. 1999).
Chen, Q.M., et al., "Apoptosis or Senescence-Like Growth Arrest: Influence of Cell-Cycle Position, p53, p21 and bax in $H_2O_2$ Response of Normal Human Fibroblasts", *Biochem. J.*, 347:543-551 (2000).
Chen, X., et al., "sir2 Mutants of *Kluyveromyces lactis* are Hypersensitive to KNA-Targeting Drugs", *Mol. Cell. Biol.*, 14:4501-4508 (Jul. 1994).
Cheng, H.L., et al., "Developmental Defects and p53 Hyperacetylation in Sir2 (SIRT1)-Deficient Mice," *Proc. Nati. Acad. Sci. USA*, 100(19): 10794-10799 (Sep. 2003), epub. www.pnas..org_cgi_doi1-.1073_pnas.1934713100.
Cheung, P., et al., "Signaling to Chromatin Through Histone Modifications", *Cell*, 103:263-271 (Oct. 2000).
Chien, C., et al., "The Two-Hybrid System: a Method to Identify and Clone Genes for Proteins that Interact with a Protein of Interest", *Proc. Natl. Acad. Sci. USA*, 88:9578-9582 (Nov. 1991).
Cho, C.Y., et al., "An Unnatural Biopolymer", *Science*, 261:1303-1305 (Sep. 1993).
Chresta. C.M. and J.A. Hickman, "Oddball p53 in testicular tumors", *Nat. Med.*, 2:745-746 (Jul. 1996).
Cristofalo, V.J. and D.Kritchevsky, "Cell Size and Nucleic Acid Content in the Diploid Human Cell Line W1-38 During Aging", *Med. Exp.* 19:313-320 (1969).
Cristofalo, V.J., et al., "Growth factors as Probes of Cell Aging", Exp. Gerontol. 24:367-374 (1989).
Cull, M.G., et al., "Screening for Receptor Ligands Using Large Libraries of Peptides Linked to the C Terminus of the *lac* Repressor", *Proc. Natl. Acad. Sci. USA*, 89:1865-1869 (Mar. 1992).
Cummings, D.J., et al., "Excision—Amplification of Mitochrondial DNA During Senescence in *Podospora anserina*", *J. Mol. Biol.*, 185:659-680 (Mar. 1985).
Cwirla, S.E., et al., "Peptides on Phage: A Vast Library of Peptides for Identifying Ligands", *Proc. Natl. Acad. Sci. USA*, 87:6378-6382 (Aug. 1990).
Cziepluch, C., et al., "Sequencing Analysis of a 40.2 kb Fragment of Yeast Chromosome X Reveals 19 Open Reading Frames Including URA2 (5' end), TRK1, PBS2, SPT10, GCD14, RPE1, PHO86, NCA3, ASF1, CCT7, GZF3, Two tRNA Genes, Three Remnant Delta Elements and a Ty4 Rransposon", *Yeast*, 12:1471-1474 (Jun. 1996).
De Witt, S.H., et al., "'Diversomes': An Approach to Nonpeptide, Nonoligomeric Chemical Diversity", *Proc. Natl. Acad. Sci. USA*, 90:6909 (Aug. 1993).
deBeus, E., et al., "Yeast NOP2 Encodes an Essential Nuleolar Protein with Homology to a Human Proliferation Marker," *Journal of Biological Chemisty*, 127(6):1799-1813 (Dec. 1994).
Devlin, J.J., et al., "Random Peptide Libraries: a Source of Specific Protein Binding Molecules", *Science*, 249:404-406 (Jul. 1990).
Dhar, S., et al., "Inactivation of 14-3-3sigma Influences Telomere Behavior and Ionizing Radiation-Induced Chromosomal Instability", *Mol. Cell. Biol.*, 20:7764-7772 (Oct. 2000).
Di Cristofano, A., et al., "Impaired Fas Response and Autoimmunity in Pten⁺/⁻ Mice", *Science*, 285:2122-2125 (Sep. 1999).
Dimri, G.P., et al.,"A Biomarker that Identifies Senescent Human Cells in Culture and in Aging Skin in vivo," *Proc. Natl. Acad. Sci. USA*, 92:9363-9367 (Sep. 1995).

Doerks, T., "Protein Annotation: Detective Work for Function Prediction," *Genetwork*, 14(6): 248-250 (Jun. 1998).
D'Mello, N.P. et al., "Molecular Analysis of a Young-Specific Gene in the Yeast *Saccharomyces cerevisiae*," *Abstracts of the 92nd General Meeting of the American Society for Microbiology*, H-284, p. 230 (May 26-30, 1992).
Dumaz, N. and D.W. Meek, "Serine 15 Phosphorylation Stimulates p53 Transactivation But Does Not Directly Influence Interaction with HDM2", *EMBO J.*, 18(24):7002-7010 (1999).
Edgington, S.M., "Is Biopharmaceutical Discovery Entering a New Evolutionary Stage?" *Bio/Technology*, 11:285 (Mar. 1993).
Egilmez, N. K. and S.M. Jazwinski, "Evidence for the Involvement of a Cytoplasmic Factor in the Aging of the Yeast *Saccharomyces cerevisiae*," *Journal of Bacteriology*, 171(1):37-42 (Jun. 1989).
Egilmez, N.K., et al., "Preparation and Partial Characterization of Old Yeast Cells", *J. Gerontol. Biol. Sci.* 45:B9-B17 (1990).
Egilmez, N.K., et al., "Specific Alterations in Transcript Prevalence During the Yeast Life Span," *The Journal of Biological Chemistry*, 264(24):14312-14317 (Apr. 1989).
El-Deriry, W.S., et al., "WAF1, a Potential Mediator of p53 Tumor Suppression", *Cell*, 75:817-825 (Nov. 1993).
Erb, E., et al., "Recursive Deconvolution of Combinatorial Chemical Libraries", *Proc. Natl. Acad. Sci. USA*, 91:11422-11426 (Nov. 1994).
Felici, J., "Selection of Antibody Ligands From a Large library of Oligopeptides Expressed on a Multivalent Exposition Vector", *J. Mol. Biol.*, vol. 222, pp. 301-310 (1991).
Ferbeyre, G., et al., "MIL is Induced by Oncogenic *ras* and Promotes Premature Senescence", *Genes Dev.*, 14:2015-2027 (Jun. 2000).
Finkel, T. and N.J. Holbrook, "Oxidants, Oxidative Stress and the Biology of Ageing", *Nature*, 408:239-247 (Nov. 2000).
Finnin, M.S., et al., "Structure of the Histone Deacetylase SIRT2", *Nat. Struct. Biol.*, 8:621-625 (Jul. 2001).
Finnin, M.S., et al., "Structures of a Histone Deacetylase Homologue Bound to the TSA and SAHA Inhibitors", *Nature*, 401: 188-193 (Sep. 1999).
Fleming, J.E., et al., "Role of Oxidative Stress in *Drosophila* Aging," *Mutation Research*, 275:267-279 (May 1992).
Fodor, S.P.A., et al., "Multiplexed Biochemical Assays with Biological Chips", *Nature*, 364:555-556 (Aug. 1993).
Franco, S., et al., Clonal Variation in Phenotype and Life Span of Huamn Embryonic Fibroblasts (MRC-5) Transduced with the Catalytic Component of Telemerase (hTERT), Experimental Cell Research, 2001, 268:14-25 (2001), doi:10.1006/excr.2001.5264, available online at http://www.ideallibrary.com.
Freedman, D.A., et al., "Functions of the MDM2 Oncoprotein", *Cell. Mol. Life Sci.*, 55(1):96-107 (1999).
Friedman, D.B. and T.E. Johnson, "A Mutation in the *age-1* Gene in *Caenorhabditis elegans* Lengthens Life and Reduces Hermaphrodite Fertility", *Genetics*, 118:75-86 (Jan. 1988).
Frye, R.A., "Characterization of Five Human cDNAs with Homology to the Yeast SIR2 Gene: Sir2-Like Proteins (Sirtuins) Metabolize NAD and May Have Protein ADP-Ribosyltransferase Activity," *Biochemical and Biophysical Res. Comm.*, 260:273-279 (May 1999).
Frye, R.A., "Phylogenetic Classification of Prokaryotic and Eukaryotic Sir2-Like Proteins", *Biochem. Biophys. Res. Commun.*, 273:793-798 (May 2000).
Frye, R.A., "Human Sir2-Like Proteins (sirtuins) are NAD-Metabolizing Protein (ADP-Ribosyl) Tranferases," *Proc. of American Assoc. for Cancer Res.*, 40:436 (Mar. 1999).
Fulco, M., et al., "SIR2 Regulates Skeletal Muscle Differentiation as a Potential Sensor of the Redox State," *Molecular Cell*, 12:51-62 (Jul. 2003).
Gallop, M.A., et al., "Applications of Combinatorial Technologies to Drug Discovery. 1. Background and Peptide Combinatorial Libraries", *J. Med. Chem.*, 37:1233 (Apr. 1994).
Garrus, J.E., et al., "Tsg101 and the Vacuolar Protein Sorting Pathway are Essential for HIV-1 Budding", *Cell*, 107(1):55-65 (Oct. 2001).
Gartenberg, M.R. "The Sir proteins of *Saccharomyces cerevisiae*: mediators of transcriptional silencing and much more", *Curr. Opin. Microbiol.*, vol. 3, pp. 132-137 (2000).
GenBank Acc. No. AL133551, "Human DNA Sequence from Clone RP11-57G10 on Chromosome 10 Contains . . . The SIRT1 Gene for Sirtuin (Silent Mating Type Information Regulation 2 Homolog) 1 (*S. cerevisiae*)," version of May 18, 2005).
GenBank Acc. No. BC026650, "*Mus musculus* Sirtuin 7 (Silent Mating Type Information Regulation 2, Homolog) 7 (*S. cerevisiae*)," version of Jun. 30, 2004.
GenBank Acc. No. BC052763, "*Mus musculus* Sirtuin 6 (Silent Mating Type Information Regulation 2, Homolog) 6 (*S. cerevisiae*)," version of Jun. 30, 2004.
GenBank Acc. No. NM_012238, "*Homo sapiens* Sirtuin (Silent Mating Type Inforamtion Regulation 2 Homolog) 1 (*S. cerevisiae*)(SIRT1)," version of Oct. 4, 2003.
GenBank Acc. No. NP_036370, Sirtuin 1: Sirtuin Silent Mating Type Information Regulation 2 Homolog 1 (*S. cerevisiae*)[*Homo sapiens*], version of Oct. 4, 2003.
GenBank Accession No. NP_036372; GI No. 6912662, first seen at NCBI on Feb. 7, 2000.
GenBank Accession No. Q8R216; GI No. 38258616, first seen at NCBI on Nov. 11, 2003.
GenBank Accession No. AA105536 (1996).
GenBank Accession No. AA199012 (1997).
GenBank Accession No. AA260334 (1997).
GenBank Accession No. AI465098 (1999).
GenBank Accession No. AI65820 (1999).
Giaccia, A.J. and M.B. Kastan, "The complexity of p53 modulation: emerging patterns from divergent signals", *Genes Dev.*, 12:2973-2983 (Oct. 1998).
Giles, R.H., et al., "Conjunction Dysfunction: CBP/p300 in Human Disease", *TIG*, 14(5):178-183 (May 1998).
Goncalves, M.A.F.V. "A Concise Peer Into the Background, Initial Thoughts and Practices of Human Gene Therapy," *Bioessays*, 27:506-517 (2005).
Goodman, R.H. and S. Smolik, "CBP/p300 in cell growth, transformation, and development", *Genes Dev.*, 14(13):1553-1577 (2000).
Gotta, M., et al., "The Clustering of Telomeres and Colocalization with Rap1, Sir3 and Sir4 Proteins in Wild-Type *Saccharomyces cerevisae*," *Journal of Cell Biology*, 134(6):1349-1363 (Sep. 1996).
Gottlieb, S., et al., "A New Role for Yeast Transcriptional Silencer Gene, SIR2, in Regulation of Recombination in Ribosoman DNA," *Cell*, 56:771-776 (Mar. 1989).
Gottschling, D.E., "Gene Silencing: Two Faces of SIR2", *Curr. Biol.*, 10: R708-R711 (2000).
Grozinger, C.M., et al., "Deacetylase Enzymes: Biological Functions and the Use of Small-Molecule Inhibitors," *Chemisty & Biology*, 3:3-16 (Jan. 2002).
Grozinger, C.M., et al., "Identification of a Class of Small Molecule Inhibitors of the Sirtuin Family of NAD-Dependent Dcacetylases by Phenotypic Screening," *Jour. of Biol. Chem.*, 276(42):38837-38843 (Oct. 2001).
Grunstein, M., "Yeast Heterochromatin: Regulation of Its Assembly and Inheritence by Histones," *Cell*, 93:325-328 (May 1998).
Gu, W., et al., "A Novel Human SRB/MED-Containing Cofactor Complex, SMCC, Involved in Transcription Regulation", *Mol. Cell*, 3:97-108 (Jan. 1999).
Gu, W., et al., "Activation of p53 Sequence-Specific DNA Binding by Acetylation of the p53 C-Terminal Domain", *Cell*, 90:595-606 (Aug. 1997).
Gu, W., et al., "Synergistic Activation of Transcription by CBP and p53", *Nature*, 387:819-823 (Jun. 1997).
Guarente, L., et al., "Genetic Pathways That Regulate Ageing in Model Organisms", *Nature*,408:255-262 (Nov. 2000).
Guarente, L. "UASs and Enhancers: Common Mechanism of Transcriptional Activation in Yeast and Mammals", *Cell*, 52:303-305 (Feb. 1988).
Guarente, L., "SIR2 and Aging—the Exception that Proves the Rule," *Trends in Genetics*, 17(7):391-392 (Jul. 2001).
Guarente, L., "Sir2 Links Chromatin Silencing, Metabolism, and Aging", *Genes Dev.*, 14:1021-1026 (2000).
Guarente, L., "Diverse and Dynamic Functions of the Sir Silencing Complex", *Nat. Genet.*, 23:281-285 (Nov. 1999).
Guo, J.C., et al., "Dual Analyte Flow Injection Fluorescence Immunoassays Using Thiophilic Gel Reactors and Synchronous Scanning Detection", *Analyst*, 125(10):1707-1708 (Sep. 2000).

Guo, A., et al., "The Function of PML in p53-Dependent Apoptosis", *Nat. Cell Biol.*, 2:730-736 (Oct. 2000).
Hamlyn, N., et al. EMBL/GenBank/DDBJ databases Accession No. Z46833 (Nov. 1994).
Hardy, C.F.J., et al., "A RAP1-Interacting Protein Involved in Transcriptional Silencing and Telemere Length Regulation," *Genes & Development*, 6:801-814 (Mar. 1992).
Harley, C.B., et al., "Telomeres Shorten During Ageing of Human Fibroblasts", *Nature*, 345:458-460 (May 1990).
Hass, B.S., et al., "Effects of caloric restriction in animals on cellular function, oncogene expression, and DNA methylation in vitro", *Mutat. Res.*, 295(4-6): 281-289 (Oct. 1993).
Hayflick, I. and P.S. Moorhead, "The Serial Cultivation of Human Diploid Cell Trains", *Exp. Cell Res.*, 25:585-621 (May 1961).
Hayflick, I., "The Limited in vitro Lifetime of Human Diploid Cell Strains", *Exp. Cell Res.*, 37:614-636 (1965).
Herrero-Yraola, A., et al., "Regulation of Glutamate Dehydrogenase by Reversible ADP-Ribosylation in Mitochondria," *The EMBO Journal*, 20(10):2404-2412 (Mar. 2001).
Hill, A.A., et al., "Genomic Analysis of Gene Expression in *C. elegans*", *Science*, 290: 809-812 (Oct. 2000).
Hirao, A., et al., "DNA damage-induced activation of p53 by the checkpoint kinase Chk2", *Science*, 287(5459):1824-1827 (Mar. 2000).
Hirsch, H.R., "Accumulation of a Senescence Factor in Yeast Cells," *Experimental Gerontology*, 28(2):195-204 (1993).
Hirschmann et al., "Nonpeptidal Peptidomimetics with a β-D-Glucose Scaffolding. A Partial Somatostatin Agonist Bearing a Close Structural Relationship to a Potent, Selective Substance P Antagonist", *J. Amer. Chem. Soc.*, vol. 114, pp. 9217-9218 (1992).
Hollstein, M., et al., "Database of p53 Gene Somatic Mutations in Human Tumors and Cell Lines", *Nucleic Acids Res.*, 22:3551-3555 (1994).
Hollstein, M. et al., "New Approaches to Understanding p53 Gene Tumor Mutation Spectra", *Mutat. Res.*, 431(2):199-209 (Jun. 1999).
Holtzman, D.A., et al., "Synthetic-Lethal Interactions Identify Two Novel Genes, SLA1 and SLA2, That Control Membrane Cytoskeleton Assembly in *Saccharomyces Cerevisiae*", J. Cell Bio., 122:635-644 (Aug. 1993).
Honda, R. and H. Yasuda, "Association of p19(ARF) With Mdm2 Inhibits Ubiquitin Ligase Activity of Mdm2 for Tumor Suppressor p53", *EMBO J.*, 18(1):22-27 (1999).
Houghten, R.A., et al., "Generation and Use of Synthetic Peptide Combinatorial Libraries for Basic Research and Drug Discovery", *Nature*, 354:84-88 (Nov. 1991).
Howitz, K.T., et al., "Small Molecule Activators of Sirtuins Extend *Saccharomyces cerevisiae*Lifespan," *Nature*, 425:191-196 (Sep. 2003).
Imai, S., et al., "Transcriptional Silencing and Longevity Protein Sir2 is an NAD-Dependent Histone Deacetylase", *Nature*, 403:795-800 (Feb. 2000).
Imai, S., et al., "Sir2: an NAD-Dependent Histone Deacetylase that Connects Chromatin Silencing, Metabolism, and Aging," *Cold Spring Harbor Symp. Quant. Biol.*, 65:297-302 (2000).
International Search Report PCT/US07/13384 dated Nov. 14, 2007.
International Search Report for PCT/US04/21630 Dated Mar. 27, 2006.
International Search Report for PCT/US94/09351 Dated Jan. 23, 1995.
International Search Report PCT/US02/21461 dated Jan. 25, 2005.
Ito, M., et al., "Identity between TRAP and SMCC Complexes Indicates Novel Pathways for the Function of Nuclear Receptors and Diverse Mammalian Activators", *Mol. Cell.*, 3:361-370 (Mar. 1999).
Ito, A., et al., "p300/CBP[mediated p53 Acetylation is Commonly Induced by p532-Activating Agents and Inhibited by MDM2", *EMBO J.*, 20:1331-1340 (2001).
Ivy, J.M., et al., "Cloning and Characterization of Four SIR Genes of *Saccharomyces cerevisiae*," Molecular and Cellular Biology, 6(2):688-702 (Feb. 1986).
Ivy, J.M., et al., "Map Positions of Yeast Genes SIR1, SIR3 and SIR4," *Genetics III*, 735-744 (Dec. 1985).
Jackson, M.D. and J.M. Denu, "Structural Identification of 2'- and 3'-O-Acetyl-ADP-Ribose as Novel Metabolites Derived from the SIR2 Family of β-$NAD^+$-Dependent Histone/Protein Deacetylases," *Jour. Biol. Chem.*, 277(21):18535-18544 (May 2002).
Jamet-Vierny, C., et al., "Senesence in *Podospora anserina*: Amplification of a Mitochondrial DNA Sequence," *Cell*, 21:189-194 (Aug. 1980).
Jazwinski, M., "Longevity, Genes, and Aging", *Science*, 273:54-59 (Jul. 1996).
Jazwinski, S.M., et al., "Replication Control and Differential Gene Expression in Aging Yeast," *Molecular Biology of Aging*, 189-203 (Mar. 1989).
Jazwinski, S.M., "Genes of Youth: Genetics of Aging in Baker's Yeast," *ASM News*, 59(4):172-178 (1993).
Jazwinski, S.M., "Aging and Senescence of the Budding Yeast *Saccharomyces cerevisiae*," Molecular Microbiology, 4(3):337-343 (Oct. 1990).
Jimenez et al., "A Transactivation-Deficient Mouse Model Provides Insights Into Trp53 Regulation and Function", *Nat. Genet.*, 26:37-43 (2000).
Juan, L., et al., "Histone Deacetylases Specifically Down-Regulate p53-Dependent Gene Activation", *J. Biol. Chem.*, 275(27):20436-20443 (Jul. 2000).
Kadowaki, T., et al., "Nuclear mRNA Accumulation Causes Nucleolar Fragmentation in Yeast mtr2 Mutant," *Molecular Biology of the Cell*, 5:1253-1263 (Nov. 1994).
Kaeberlein, M., et al., "The SIR2/3/4 Complex and SIR2 Alone Promote Longevity in *Saccharomyces cerevisiae* by Two Different Mechanisms," *Genes & Development*, 13:2570-2580 (Aug. 1999).
Karpen, G.H., and R.C. Allshire, "The Case for Epigenetic Effects on Centromere Identity and Function," *TIG*, 13(12):489-496 (Dec. 1997).
Kastan, M.B., et al., "A Mammalian Cell Cycle Checkpoint Pathway Utilizing P 53 and TGADD45 is Defective in Ataxia-Telangiectasis", *Cell*, 71:587-597 (Nov. 1992).
Kennedy, B.K., et al., "Redistribution of Silencing Proteins from Telomeres to the Nucleolus is Associated with Extension of Life Span in *S. cerevisiae*," *Cell*, 89:381-391 (May 1997).
Kenyon, C., et al., "A *C. elegans* Mutant That Lives Twice as Long as Wild Type", *Nature*,366:461-464 (Dec. 1993).
Khanna, K.K. et al., "ATM Associates With and Phosphorylates P53: Mapping the Region of Interaction", *Nat. Genet.*, 20(4):398-400 (Dec. 1998).
Kobet, E., et al., "MDM2 Inhibits p300-Mediated P53 Acetylation and Activation by Forming a Ternary Complex With the Two Proteins", *Proc. Natl. Acad. Sci. USA*, 97:12547-12552 (Nov. 2000).
Kofler, B., et al., "Purification and Characterization of NAD+: ADP-Ribosyltransferase (Polymerizing) from *Dictyostelium discoideum*," *Biochem, J.*, 293:275-281 (1993).
Kohl, N.E., et al., "Selective Inhibition of ras-Dependent Transformation by a Farnesyltransferase Inhibitor", *Science*, 260:1934 (Jun. 1993).
Koll, F., et al., "A 1100-bp Sequence of Mitochondiral DNA is Involved in Senescence Process in Podospora: Study of Senescent and Mutant Cultures", *Plasmid*, 14:106-117 (Jun. 1985).
Kouzarides, T., "Acetylation: a Regulatory Modification to Rival Phosphorylation?" *EMBO J.*, 19:1176-1179 (2000).
Kung, A.L., et al., "Gene Dose-Dependent Control of Hematopoiesis and Hematologic Tumor Suppression by CBP", *Genes Dev.*, 14(3):272-277 (2000).
Kuo, M.H., et al., "Roles of histone acetyltransferases and deacetylases in gene regulation", BioEssays, vol. 20, pp. 615-626 (1998).
Lam, P.YS., et al., "Rational Design of Potent, Bioavailable, Nonpeptide Cyclic Ureas As HIV Protease Inhibitors", *Science*, 263:380 (Jan. 1994).
Lam, K.S., et al. "A New Type of Synthetic Peptide Library for Identifying Ligand-Binding Activity", *Nature*, 354:82-84 (Nov. 1991).
Lambert, P.F., et al., "Phosphorylation of p53 Serine 15 Increases Interaction with CBP", *J. Biol Chem.*, 273:33048-33053 (Dec. 1998).
Landry, J., et al., "The Silencing Protein SIR2 and its Homolog are NAD-Dependent Protein Deacetylases," PNAS, 97(11):5807-5811 (May 2000).

Landry, J., et al., "Role of NAD(+) in the Deacetylase Activity of the SIR2-like Proteins", *Biochem. Biophys. Res. Commun.*, 278:685-690 (Oct. 2000).

Langley, E., et al., "Human SIR2 Deacetylates p53 and Antagonizes PM/p53-Induced Cellular Senescence," *EMBO Journal*, 21:2383-2396 (2002) (month not available).

Lavitrano, M., et al., "Sperm Cells as Vectors for Introducing Foreign DNA into Eggs: Genetic Transformation of Mice", *Cell*, 57:717-723 (Jun. 1989).

Lazarus, C.M., et al., "Amplification of a Mitochondrial DNA Sequence in the Cytoplasmically Inherited 'Ragged' Mutant of *Aspergillus amstelodami*", *Eur. J. Biochem*, 106:663-641 (1980).

Lee, S. and D.S. Gross, "Conditional Silencing: The HMRE Mating-Type Silencer Exerts a Rapidly Reversible Position Effect on the Yeast HSP82 Heat Shock Gene," *Molecular and Cellular Biology*, 13(2):727-738 (1993).

Lee, S.E., et al., "Role of Yeast SIR Genes and Mating Type in Directing DNA Double-Strand Breaks to Homologous and Non-Homologous Repair Paths", *Curr. Biol.*, 9:767-770 (Jul. 1999).

Levine, AJ, "p53, the Cellular Gatekeeper for Growth and Division", *Cell*, 88:323-331 (Feb. 1997).

Li, Y., et al., "Long-Term Caloric Restriction Delays Age-Related Decline in Proliferation Capacity of Murine Lens Epithelial Cells in vitro and in vivo", *Invest. Ophthalmol.*, 38(1):100-107 (Jan. 1997).

Liang, R., et al., "Parallel Synthesis and Screening of a Solid Phase Carbohydrate Library", *Science*, 274:1520-1522 (Nov. 1996).

Lill, N.L., et al., "Binding and Modulation of p53 by p300/CBP Coactivators", *Nature*, 387:823-827 (Jun. 1997).

Lin, S., et al., "Requirement of NAD and SIR2 for Life-Span Extension by Calorie Restriction in *Saccharomyces cerevisiae*" Science, 289:2126-2128 (Sep. 2000).

Lin, S., et al., "Multiple Tumor Suppressor Pathways Nevatively Regulate Telomerase," *Cell*, 113:881-889 (Jun. 2003).

Liu, L., et al., "p53 Sites Acetylated in vitro by PCAF and p300 are Acetylated in vivo in Response to DNA Damage", *Mol. Cell. Biol.*, 19:1202-1209 (Feb. 1999).

Lo, C.W., "Transformation by Iontophoretic Microinjection of DNA: Multiple Integrations Without Tandem Insertions", *Mol. Cell Biol.*, 3:1803-1814 (Oct. 1983).

Lohrum, M. and K.H. Vousden, "Regulation and Activation of p53 and its Family Members", *Cell Death Differ.*, 6(12):1162-1168 (Oct. 1999).

Longtine, M.S., et al., "Telomere-Mediated Plasmid Segregation in *Saccharomyces cerevisiae* Involves Gene Products Required for Transcriptional Repression at Silencers and Telomeres," *Genetics*, 133:171-182 (Feb. 1993).

Lumpkin, C.K., et al., "Existence of High Abundance Antiproliferative mRNA's in Senescent Human Diploid Fibroblasts", *Science*, 232:393-395 (Apr. 1986).

Lundblad, V., et al., "A Mutant With a Defect in Telomere Elongation Leads to Senescence in Yeast," *Cell*, 57:633-643 (May 1989).

Luo, J., et al., "Deacetylation of p53 Modulates its Effect on Cell Growth and Apoptosis," *Nature*, 408:377-381 (Nov. 2000).

Luo, J., et al., "Negative Control of p53 by Sir2α Promotes Cell Survival Under Stress," *Cell*, 107:137-148 (Oct. 2001).

Lutzker, S.G., et al., "A functionally inactive p53 protein in teratocarcinoma cells is activated by either DNA damage or cellular differentiation", *Nat. Med.*, 2:804-810 (Jul. 1996).

Marasco, W.A., et al., "Design, Intracellular Expression, and Activity of a Human Anti-Human Immunodeficiency Virus Type 1 gp120 Single-Chain Antibody", *Proc. Natl. Acad. Sci. USA*, 90:7889-7893 (Aug. 1993).

Marbois, B., et al., "The COQ7 Gene Encodes a Protein in *Saccharomyces cerevisiae* Necessary for Ubiquinone Biosynthesis", *J. Biol. Chem.*, 271(6), pp. 2995-3004 (Feb. 1996).

Marchler-Bauer, A., et al., "CDD: A Conserved Domain Database for Protein Classification," *Nucleic Acids Research*, 33:192-196 (2005).

Marks, P.A., et al., "Inhibitors of Histone Deacetylase are Potentially Effective Anticancer Agents", *Clin. Cancer Res.*, 7: 759-760 (Apr. 2001).

Marks, P.A., et al., "Histone Deacetylase Inhibitors: Inducers of Differentiation or Apoptosis of Transformed Cells", J. Nat'l Cancer Inst., 92(15):1210-1216 (Aug. 2000).

Marshall, M., et al., "Functional Domains of SIR4, a Gene Required for Position Effect Regulation in *Saccharomyces cerevisiae*," *Molecular and Cellular Biology*, 7(12):4441-4452 (Dec. 1987).

Martin, S.G., et al., "Relocalization of Telomeric Ku and SIR Proteins in Response to DNA Strand Breaks in Yeast," *Cell*, 97:621-63 (May 1999).

Maya, R., et al., "ATM-Dependent Phosphorylation of Mdm2 on Serine 395: Role in p53 Activation by DNA Damage" *Genes Dev.*, 15:1067-1077 (Feb. 2001).

McAinsh, A.D., et al., "DNA Damage Triggers Disruption of Telomeric Silencing and Mec1p-Dependent Relocation of Sir3p", *Curr. Biol.*, 9:963-966 (Aug. 1999).

McBurney, M.W., et al., "The Mammalian SIR2_Protein Has a Role in Embryogenesis and Gametogenesis," *Molecular and Cellular Biology*, 23(1):38-54 (Jan. 2003).

McConnell, S.J., et al., "Temperate-sensitive Yeast Mutants Defective in Mitochondrial Inheritance", *J. Cell Biol.* 111:967-976 (Sep. 1990).

Migliaccio, E., et al., "The p66$^{she}$ Adaptor Protein Controls Oxidative Stress Response and Life Span in Mammals", *Nature*, 402:309-313 (Nov. 1999).

Mills, K.D., et al., "MEC1-Dependent Redistribution of the Sir3 Silencing Protein from Telomeres to DNA Double-Strand Breaks," *Cell*, 97:609-620 (May 1999).

Min, J., et al., "Crystal Structure of a SIR2 Homolog-NAD Complex", *Cell*, 105:269-279 (Apr. 2001).

Miura, T. and R. Sato, "Cellular Senescence in Yeast Caused by Carbon-Source Starvation," *J. Biochem.*, 76(3):593-601 (1974).

Miura, T. and T. Yanagita, "Cellular Senescence in Yeast Caused by Carbon-Source Starvation," *J. Biochem.*, 72(1):141-148 (1972).

Moazed, D., "Common Themes in Mechanisms of Gene Silencing," *Molecular Cell*, 8:489-498 (Sep. 2001).

Moazed, D., "Enzymatic Activities of Sir2 and Chromatin Silencing", Curr. Opin. Cell Biol, 13:232-238 (Apr. 2001).

Moretti, P., et al., "Evidence That a Complex of SIR Proteins Interacts with the Silencer and Telomere-Binding Protein RAP1," *Genes & Development*, 8:2257-2269 (Aug. 1994).

Morgenstern, J.P., et al., "Advanced Mammalian Gene Transfer: High Titre Retroviral Vectors with Multiple Drug Selection Markers and a Complementary Helper-Free Packaging Cell Line", *Nucl. Acids Res.*, 18:3587-3596 (May 1990).

Mortimer, R.K. and J.R. Johnston, "Life Span of Individual Yeast Cells", *Nature*, 183:1751-1752 (1959).

Muller, I. and F. Wolf, "A Correlation Between Shortened Life Span and UV-Sensitivity in Some Strain of *Saccharomyces cerevisiae*", *Mol. Gen. Genet.*, 160:231-234 (1978).

Muller, I., "Experiments on Ageing in Single Cells of *Saccharomyces cerevisiae*", *Arch. Mikrobiol.*, 77:20-25 (Dec. 1971).

Muller, I., "Parental Age and the Life-Span of Zygotes of *Saccharomyces cerevisiae*", *Antonie van Leeuwenhoek*, 51:1-10 (1985).

Muller, I., et al., "Calendar Life Span Versus Budding Life Span of *Saccharomyces cerevisiae*," Mechanisms of Aging and Development, 12(1):47-52 (1980).

Muth. V., et al., "Acetylation of TAF(1)68, a subunit of TIF=IB/SL1, activates RNA polymerase I transcription", *EMBO J.*, 20(6):1353-1362 (2001) (month not available).

Nakamura, S., et al., "Multiple Lysine Mutations in the C-Terminal Domain of p53 Interfere with MDM2-Dependent Protein Degradation and Ubiquitination", *Mol. Cell. Biol.*, 20:9391-9398 (Dec. 2000).

Nakano, K., et al., "PUMA, a Novel Proapoptotic Gene, is Induced by p53", *Mol. Cell*, 7:683-694 (Mac. 2001).

Nehlin, J.O, et al., "The Werner Syndrome. A Model for the Study of Human Aging", *Annals NY Acad. Sci.*, 908:167-179 (2000).

Ngo, J.T., et al., "Computational Complexity, Protein Structure Prediction, and the Levinthal Paradox," The Protein Folding Problem and Tertiary Structure Prediction, 492-495 (1994).

North, B.J., et al., "The Human Sir2 Ortholog, SIRT2, is an NAD+-Dependent Tubulin Deacetylase," *Molecular Cell*, 11:437-444 (Feb. 2003).

Norwood, T.H., et al., "Dominance of the Senescent Phenotype in Heterokaryons Between Replicative and Post-Replicative Human Fibroblast-Like Cells", *Proc. Natl. Acad. Sci. USA*, 71:2231-2235 (Jun. 1974).

Oakes, M., et al., "Structural Alterations of the Nucleolus in Mutants of *Saccharomyces cerevisiae* Defective RNA Polymerase 1," *Molecular and Cellular Biology*, 13(4):2441-2455 (Apr. 1993).

Oda, K., et al., "p53AIP1, a Potential Mediator of p53-Dependent Apoptosis, and its Regulation by Ser-46-Phosphorylated p53", *Cell*, 102(6):849-862 (Sep. 2000).

Oda, E., et al., "Noxa, a BH3-Only Member of the Bcl-2 Family and Candidate Mediator of p53-Induced Apoptosis", *Science*, 288(5468):1053-1058 (May 2000).

Okamoto, K. and D. Beach, "Cyclin G is a Transcriptional Target of the p53 Tumor Suppressor Protein", *EMBO J.*, 13:4816-4822 (1994).

Olovnikov, A.M., "A Theory of Marginotomy: The Incomplete Copying of Template Margin in Enzymic Synthesis of Polynucleotides and Biological Significance of the Phenomenon", *J. Theor. Biol.* 41:181-190 (1973).

Onyango, P., et al., "SIRT3, a Human SIR2 Homologue, is an NAD-Dependent Deacetylase Localized to Mitochondria," *PNAS*, 99(21):13653-13658 (Oct. 2002).

Oren, M., "Regulation of the p53 Tumor Suppressor Protein", *J. Biol. Chem.*, 274:36031-36034 (Dec. 1999).

Orgel, L.E., "Ageing of Clones of Mammalian Cells", *Nature*, 243:441-445 (Jun. 1973).

Pabo, C.O. "Transcription Factors: Structural Families and Principles of DNA Recognition," *Annu. Rev. Biochem.*, 61:1053-1075 (1992).

Palladino, F., et al., "SIR3 and SIR4 are Required for the Positioning and Integrity of Yeast Telomeres," *Cell*, 75:543-555 (Nov. 1993).

Park, P.U., et al., "Effects of Mutations in DNA Repair Genes on Formation of Ribosomal DNA Circles and Life Span in *Saccharomyces cerevisiae*," *Molecular and Cellular Biology*, 19:3848-3856 (May 1999).

Pearson, M., et al., "PML Regulates p53 Acetylation and Premature Senescence Induced by Oncogenic Ras", *Nature*, 406:207-210 (Jul. 2000).

Pelissier, P., et al., "NCA3, a Nuclear Gene Involved in the Mitochondrial Eexpression of Subunits 6 and 8 of the Fo-F1 ATP Synthase of *S. cerevisiae*", *Curr. Genet.* 27:409-416 (1995).

Pereira-Smith, O.M. and J.R. Smith, "Genetic Analysis of Indefinite Division in Human cells: Identification of Four Complementation Groups", *Proc. Natl. Acad. Sci. USA* 85:604-60462 (Aug. 1988).

Picard, F., et al., "Sirl Promotes Fact Mobilization in White Adipocytes by Repressing PPAR-γ," *Nature*, 429:771-776 and corrigendum from vol. 430:921 (Jun. 2004).

Pohley, H., "A formal Mortality Analysis for Populations of Unicellular Organisms (*Saccharomyces cerevisiae*)", *Mechanisms of Ageing and Development*, 38:231-243 (1987).

Pomerantz, J., et al., "The Ink4a Tumor Suppressor Gene Product, p19$^{Arf}$, Interacts with MDM2 and Neutralizes MDM2's Inhibition of p53", Cell, 92(6), pp. 713-723 (Mar. 1998).

Presentation given by Marcia Haigis at Cold Spring Harbor Conference, Oct. 6-10, 2004.

Pringle, J.R., et al., "Fluorescence Microscopy Methods for Yeast", *Methods in Cell Biology*, 31:357-435 (1989).

Prives, C., and P.A. Hall, "The p53 Pathway", *Pathol. J.*, 187:112-126 (1999).

Proft, M., et al., "CAT5, a New Gene Necessary for Derepression of Gluconeogenic Enzymes in *Saccharomyces cerevisiae*", *EMBO J.*, 14(24):6116-6126 (1995).

Rim, J.S. and L.P. Kozak, "Regulatory Motifs for CREB-Binding Protein and Nfe212 Transcription Factors in the Upstream Enhancer of the Mitochondrial Uncouplinig Protein 1 Gene," *Journal of Biological Chemistry*, 277(37): 34589-34600 (Jun. 2002).

Rine, J. and I. Hershkowitz, "Four Genes Responsible for a Position Effect on Expresson from *HML* and *HMR* in *Saccharomyces cerevisae*," *Genetics*, 116:9-22 (May 1987).

Rodriguez, M.S., et al., "Multiple C-Terminal Lysine Residues Target p53 for Ubiquitin-Proteasome-Mediated Degradation", *Mol. Cell. Biol.*, 20:8458-8467 (Nov. 2000).

Rogina, B., and S.L. Helfand, "Cu, Zn Superoxide Dismutase Deficiency Accelerates the Time Course of an Age-Related Marker in *Drosophila melanogaster*", *Biogerontology*, 1:163-169 (2000).

Rogina, B., et al., "*Drosophila Drop-Dead* Mutations Accelerate the Time Course of Age-Related Markers", *Proc. Natl. Acad. Sci. USA*, 94:6303-6306 (Jun. 1997).

Sainsard-Chanet, A. and O. Begel, "Transformation of Yeast and *Podospora*: Innocuity of Senescence-Specific DNAs," *Mol Gen Genet.*, 204:443-451 (1986).

Sakaguchi, K., et al., "DNA Damage Activates p53 Through a Phosphorylation-Acetylation Cascade", *Genes Dev.*, 12:2831-2841 (Jul. 1998).

Sartorelli, V., et al., "The Link Between Chromatin Structure, Protein Acetylation and Cellular Diffierientiation," *Frontiers in Bioscience*, 6:1024-1047 (Sep. 2001).

Schnell, R., et al., "Genetic and Molecular Characterizations of Suppressors of SIR4 Mutations in *Saccharomyces cerevisiae*," *Genetics*,122:29-46 (May 1989).

Schwer, B., et al., "The Human Silent Information Regulator (Sir)2 Homologue hSIRT3 is a Mitochondrial Nicotinamide Adenine Dinucleotide-Dependent Deacetylase," *JCB*, 158(4):647-657 (Aug. 2002).

Scott, J.K. and G.P. Smith, "Searching for Peptide Ligands with an Epitope Library", *Science*, 249:386-390 (Jun. 1990).

Seeler, J.S. and A. Dejean, "The PML Nuclear Bodies: Actors or Extras?," *Curr. Opin. Genet. Dev.*, 9(3):362-367 (Jun. 1999).

Senawong, T., et al., "Involvement of the Histone Deacetylase SIRT1 in Chicken Ovalbumin Upstream Promoter Transcription Factor (COUP-TF)-Interacting Protein 2-Mediated Transcriptional Repression," *J. Biol. Chem.*, 278(44):43041-43050 (Oct. 2003), published *JBC Papers in Press*, Aug. 19, 2003, DOI 10.1074/jbc.M307477200.

Serrano, M., et al., "Oncogenic ras Provokes Premature Cell Senescence Associated with Accumulation of p53 and p16I8NK4a", *Cell*, 88(5):593-602 (Mar. 1997).

Sharpless, N.E. and R.A. DePinho., "The INK4A/ARF Locus and Its Two Gene Products", *Curr. Opin. Genet. Dev.*, 9(1):22-30 (1999).

Sherman, J.M., and L. Pillus, "An Uncertain Silence," *TIG*, 13(8):308-313 (Aug. 1997).

Shi, T., et al., "SIRT3, a Mitochondrial Sirtuin Deacetylase, Regulats Mitochondrial Function and Thermogenesis in Brown Adipocytes," Journal of Biological Chemistry, 280(14):13560-13567 (Apr. 2005).

Sherr, C.J., et al., "The ARF/p53 Pathway", *Curr. Opin. Genet. Dev.*, 10(1):94-99 (2000).

Shieh, S., et al., "DNA Damage-Induced Phosphorylation of p53 Alleviates Inhibition MDM2", *Cell*, 91:325-334 (Oct. 1997).

Shieh, S., et al., "The Human Homologs of Checkpoint Kinases Chk1 and Cds1(Chk2) Phosphorylate p53 at Multiple DNA Damage-Inducible Sites", *Genes Dev.*, 14:289-300 (2000).

Shore, D., "The Sir2 Protein Family: A Novel Deacetylase for Gene Silencing and More", *Proc. Natl. Acad. Sci. USA*, 97:14030-14032 (Dec. 2000).

Shou, W., et al., "Exit from Mitosis is Triggered by Tem1-Dependent Release of the Protein Phosphatase Cdc14 from Nucleolar RENT Complex," *Cell*, 97:233-244 (Apr. 1999).

Siliciano, J.D., et al., "DNA Damage Induces Phosphorylation of the Amino Terminus of p53", *Genes Dev.*, 11:3471-3481 (Nov. 1997).

Simon, R.J., et al., "Peptoids: a Modular Approach to Drug Discovery" *Proc. Natl. Acad. Sci. USA*, 89:9367 (Oct. 1992).

Sinclair, D.A. and L. Guarente, "Extrachromosomal rDNA Circles—A Cause of Aging in Yeast," *Cell*, 97:1033-1042 (Dec. 1997).

Sinclair, D.A., et al. "Molecular Mechanisms of Yeast Aging," *TIBS* 23:131-134 (Apr. 1998).

Sinclair, D.A., et al., "Accelerated Aging and Nuclear Fragmentation in Yeast sgs1 Mutants," Science, 277:1313-1316 (Aug. 1997).

Skolnick, J., et al., "From Genes to Protein Structgure and Function: Novel Applications of Computational Approaches in the Genomoc Era," *Trends in Biology*, 18:34-39 (Jan. 2000).

Smith, J.S., et al., "A Phylogenetically Conserved NAD-Dependent Protein Deacetylase Activity in the Sir2 Protein Family", *Proc. Natl. Acad. Sci. USA*, 97:6658-6663 (Jun. 2000).

Smith, J.S., et al., "Human Sir2 and the 'Silencing' of p;53 Activity," *Trends in Cell Biol.* 12: 404-406 (Sep. 2002).

Smith, J.S. and J.D. Boeke, "An Unusual Form of Transcriptional Silencing in Yeast Ribosomal DNA," *Genes & Development*, 11:241-254 (Dec. 1997).

Smith, T.F. and X. Zhang, "The Challengers of Genome Sequence Annotation or 'The Devil in the Details'," Nature Biotechnology, 15:1222-1223 (Nov. 1997).

Sterner, D.E. and S.L. Berger, "Acetylation of Histones and Transcription-Related Factors", *Microbiol. Mol. Biol. Rev.*, 64(2), pp. 435-459 (Jun. 2000).

Stewart, S.A., et al., "Lentivirus-Delivered Stable Gene Silencing by RNAi in Primary Cells," *RNA* 9(4):493-501 (2003).

Supplementary Partial European Search Report EP 02 74 9837 dated Jun. 29, 2005.

Sussel, L. and D. Shore, "Separation of Transcriptional Activation and Silencing Functions of the RAP1-Encoded Repressor/Activator Protein 1: Isolation of Viable Mutants Affecting Both Silencing and Telomere Length," *Proc. Natl. Acad. Sci. USA*, 88:7749-7753 (Sep. 1991).

Sweeney, R. and V.A. Zakian, "Extrachromosomal Elements Cause a Reduced Division Potential in *nib1* Strains of *Saccharomyces cerevisiae*," *Genetics*, 122:749-757 (Aug. 1989).

Tani, T., et al., "Nucleolar Accumulation of Poly (A)+ RNA in Heat-Shocked Yeast Cells: Implicatin of Nucleolar Involvement in mRNA Transport," *Molecular Biology of the Cell*, 6:1515-1534 (Nov. 1995).

Tanner, K.G., et al., "Silent Information Regulator 2 Family of NAD-Dependent Histone/Protein Deacetylases Generates a Unique Product, 1-O-acetyl-ADP-Ribose", *Proc. Natl. Acad. Sci. USA*, 97:14178-14182 (Dec. 2000).

Tanny, J.C., et al., "Coupling of Histone Deacetylation of NAD Breakdown by the Yeast Silencing Protein Sir2: Evidence for Acetyl Transfer from Substrate to an NAD Breakdown Product", *Proc. Natl. Acad. Sci. USA*, 98:415-420 (Dec. 2001).

Tanny, J.C., et al., "An Enzymatic Activity in the Yeast Sir2 Protein that is Essential for Gene Silencing," *Cell*, 99:735-745 (Dec. 1999).

Tao, W., et al., "Nucleocytoplasmic shuttling of oncoprotein HDM1 is required for HDM2-Mediated Degradation of P53", *Proc. Natl. Acad. Sci. USA*, 96(6):3077-3080 (Mar. 1999).

Tao, W., et al., "P19$^{ARF}$ Stabilizes p53 by Blocking Nucleo-Cytoplasmic Shuttling of Mdm2", *Proc. Natl. Acad. Sci. USA*, 96(12):6937-6941 (Jun. 1999).

Taunton, J., et al., "A Mammalian Histone Deacetylase Related to the Yeast Transcriptional Regulator Rpd3p", *Science*, 272:408-411 (Apr. 1996).

Thompson, S., et al., "Germ Line Transmission and Expression of a Corrected HPRT Gene Produced by Gene Targeting in Embryonic Stem Cells", *Cell*, 56:313-321 (Jan. 1989).

Tissenbaum, H.A., et al., "Increased Dosage of a sir-2 Gene Extends Lifespan in *Caenorhabditis elegans*", *Nature*, 410:227-230 (Mar. 2001).

Triolo, T., and R. Sternglanz, "Role of Interactions Between the Origin Recognition Complex and SIR1 in Transcriptional Silencing," *Nature*, 381:251-253 (May 1996).

Tsai, D.E., et al., "In vitro Selection of an RNA Epitope Immunologically Cross-Reactive with a Peptide", Proc. Natl. Acad. Sci. USA, 89:8864-8868 (Oct. 1992).

Tsai, D.E. and J.D. Keene, "In Vitro Selection of RNA Epitopes Using Autoimmune Patient Serum[1]", *Immunology*, 150:1137 (Feb. 1993).

Tsang, A.W., and J.C. Escalante-Semerena, "CobB, a New Member of the SIR2 Family of Eucaryotic Regulatory Proteins is Required to Compensate for the Lck of Nicotinate Mononucleotide:5,6-Dimethylbenzimidazole Phosphoribosyltransferase Activity in *cobT* Mutants During Cobalamin Biosynthesis in *Salmonella typhimurium* LT2*," *Journal of Biological Chemistry*, 273(48); 31788-31794 (Nov. 1998).

Tyner, S.D., et al., "p53 Mutant Mice that Display Early Ageing-Associated Phenotypes", *Nature*, 415:45-53 (Jan. 2002).

Unger, T., et al., "Critical Role for Ser20 of Human p53 in the Negative Regulation of p53 by Mdm2", *EMBO J.*, 18(7):1805-1814 (1999).

Urrestarazu, et al., Protein Sequence Database, Accession No. S38114 (May 3, 1994).

Van Der Putten, H., et al., "Efficient Insertion of Genes Into the Mouse Germ Line Via Retroviral Vectors", *Proc. Natl. Acad. Sci. USA*, 82:6148-6152 (Sep. 1985).

Vaughn, T.J., et al., "Human Antibodies with Sub-nanomolar Affinities Isolated from a Large Non-immunized Phage Display Library," *Nature Biotechnology*, 14(3):309-314 (Mar. 1996).

Vaziri, H., et al., "Analysis of Genomic Integrity and p53-Dependent G1 Checkpoint in Telomerase-Induced Extended-Life-Span Human Fibroblasts", *Mol. Cell. Biol.*, 19:2373-2379 (Mar. 1999).

Vaziri, H., et al., "ATM-Dependent Telomere Loss in Aging Human Diploid Fibroblasts and DNA Damage Lead to the Post-Translational Activation of p53 Protein Involving Poly (ADP-Ribose) Polymerase", *EMBO J.*, 16:6018-6033 (1997).

Vaziri, H., et al., "hSIR2sirt1 Functions as an NAD-Dependent p53 Deacetylase," Cell, 107:149-159 (Oct. 2001).

Vogelstein, B., et al., "Surfing the p53 Network", *Nature*, 408:307-310 (Nov. 2000).

Vousden, K.H., "p53: Death Star", *Cell*, 103(5):691-694 (Nov. 2000).

Weber, J.D., et al., "Nucleolar Arf Sequesters Mdm2 and Activates p53", *Nat. Cell. Biol.*, 1(1):20-26 (May 1999).

Weindruch, R., et al., "The Retardation of Aging in Mice by Dietary Restriction: Longevity, Cancer, Immunity and Lifetime Energy Intake", *Journal of Nutrition*, 116(4):641-654 (Nov. 1985).

Wells, J.A., "Additivity of Mutational Effects in Proteins," Perspectives in Biochemistry, 29(37):8509-8517 (Sep. 1990).

Wolf, N.S. and W.R. Pendergrass, "The Relationships of Animal Age and Caloric Intake to Cellular Replication In Vivo and In Vitro: A Review", *J. Gerontol. A Bio. Sci. Med. Sci.*, 54(11):B502-B517 (1999).

Wolffe, A.P., et al., "Review: Chromatin Structural Features and Targets That Regulate Transcription", *J. Struct. Biol.*, 29(2-3):102-122 (2000).

Wu. W., et al., "The p53-mdm-2 Autoregulatory Feedback Loop", *Genes Dev.*, 7:1126-1132 (Apr. 1993).

Yang, X.H., et al., "Cloning and Characterization of Two Mouse Genes with Homology to the Yeast *Sir2* Gene," *Genomics*, 69:355-369 (Nov. 2000).

Yin, Y., et al., "Involvement of p85 in p53-Dependent Apoptotic Response to Oxidative Stress", *Nature*, 391:707-710 (Feb. 1998).

Yu, A., et al., "Activation of p53 or loss of the Cockayne syndrome group B repair protein causes metaphase fragility of human U1, U2, and 58 genes", *Mol. Cell*, 5:801-810 (May 2000).

Yu, Y., et al., "PUMA Induces the Rapid Apoptosis of Colorectal Cancer Cell," *Molecular Cell*, 7:673-682 (Mar. 2001).

Zhang, Y., et al., "SAP30, a Novel Protein Conserved Between Human and Yeast, is a Component of a Histone Deacetylase Complex", *Mol. Cell*, 1:1021-1031 (Jun. 1998).

Ziegler, M., et al., "New Functions of a Long-Known Molecule—Emerging Roles of NAD in Cellular Signaling," *Eur. J. Biochem.*, 267:1550-1564 (Jan. 2000).

Carroll, S.F. and R.J. Collier, "Photoaffinity labeling of active site residues in ADP-ribosylating toxins", *Methods Enzymol.*, 235:631-639 (1994).

Furka, A., et al. "General Method for Rapid Synthesis of Multicomponent Peptide Mixtures", *Int. J. Pept. Prot. Res.*, 37:487-493 (1991).

Gordon, J.W., "Transgenic Animals," *Intl. Rev. Cytol.*, 115:171-229 (1989).

Hagihara, M., et al., "Viylogous Polypeptides: An Alternative Peptide Backbone," *J. Amer. Chem. Soc.*, 114: 6568-6570 (1992).

Houghten, R.A., et al. "The Use of Synthetic Peptide Combinatorial Libraries for the Identification of Bioactive Peptides," *Biotechniques*, 13:412-421 (1992).

Kari, F.W., et al., "Roles for Insulin-Like Growth Factor-1 in Mediating the Anti-Carcinogenic Effects of Caloric Restriction", *J. Nutr. Health Aging*, 3(2):92-101 (1999).

Mitsudomi, T., et al., "p53 Gene Mutations in Non-Small-Cell Lung Cancer Cell Lines and Their Correlation With the Presence of Ras Mutations and Clinical Features", *Oncogene*, 7:171-180 (1992).

NCBI Accession No. O46955, submitted Aug 1995.

NCBI Accession No. P25339, submitted May 1996.

NCBI Accession No. P46955, submitted Aug. 1995.

Tsang, N. M., et al., "Abrogation of p53 Function by Transfection of HPV16 E6 Gene Enhances the Resistance of Human Diploid Fibroblasts to Ionizing Radiation", *Oncogene*, 10:2403-2408 (1995).

Tibbetts, R.S., et al., "The DnaJ family of protein chaperones in *Trypanosoma cruzi*", *Mol. Biochem. Parasitol.*, 91(2):319-326 (1998).

Yoshida, M., et al., "Trichostatin A and Trapoxin: Novel Chemical Probes for the Role of Histone Acetylation in Chromatin Structure and Function", *Bioessays*, 5:423-430 (Feb. 1995).

Zuckermann, R.N., et al., "Discovery of Nanomolar Ligands for 7-Transmembrane G-protein-coupled Receptors from a Diverse N-(Substituted)glycine Peptoid Library", *J. Med. Chem.*, 37:2678-2685 (1994).

U.S. Office Action dated Dec. 10, 2003 for U.S. Appl. No. 09/826,752.

U.S. Office Action dated Jul. 15, 2006 for U.S. Appl. No. 11/409,170.

U.S. Office Action dated Nov. 3, 2008 for U.S. Appl. No. 11/409,170.

U.S. Office Action dated May 25, 2010 for U.S. Appl. No. 10/885,977.

U.S. Office Action dated Oct. 23, 2008 for U.S. Appl. No. 10/885,977.

U.S. Office Action dated Mar. 19, 2008 for U.S. Appl. No. 10/885,977.

U.S. Office Action dated Dec. 21, 2006 for U.S. Appl. No. 10/885,977.

U.S. Office Action dated Jul. 1, 1996 for U.S. Appl. No. 08/396,001.

U.S. Office Action dated Jun. 1, 1998 for U.S. Appl. No. 08/861,464.

U.S. Office Action dated Apr. 7, 2000 for U.S. Appl. No. 09/323,433.

U.S. Office Action dated Apr. 18, 2003 for U.S. Appl. No. 09/826,752.

U.S. Office Action dated Mar. 23, 2006 for U.S. Appl. No. 10/993,903.

U.S. Office Action dated Oct. 23, 2006 for U.S. Appl. No. 10/993,903.

U.S. Office Action dated Apr. 23, 2007 for U.S. Appl. No. 10/993,903.

U.S. Office Action dated Nov. 15, 2007 for U.S. Appl. No. 10/993,903.

U.S. Office Action dated Jul. 21, 2009 for U.S. Appl. No. 10/993,903.

U.S. Office Action dated Jun. 9, 2010 for U.S. Appl. No. 10/993,903.

U.S. Office Action dated Jul. 8, 2011 for U.S. Appl. No. 10/993,903.

Haigis et al., "SIRT4 inhibits Glutamate dehydrogenase and opposes the effects of calorie restriction in pancreatic beta cells," *Cell*, 126: 941-954 (2006).

GenBank AF083109 data sheet, 2 pages, 2012.

Einhauer et al., "The FLAG peptide, a versatile fusion tag for the purification of recombination proteins," *J of Biochemical and Biophysical Methods*, 49: 455-465 (2001).

Appella et al., "Signaling to p53: breaking the posttranslational modification code," *Pathol. Biol.*, 48: 227-245 (2000).

Bordone, L. et al., "Sir1 Regulates Insulin Secretion by Repressing UCP2 in Pancreatic β Cells," *Plos. Biol.*, 4(2): 0210-0220 (Feb. 2006).

Brachmann et al., "The SIR2 gene family, conserved from bacteria to humans, functions in silencing, cell cycle progression, and chromosome stability," *Genes Dev.*, 9: 2888-2902 (1995).

Burnett, C. et al., "Absence of Effects of Sir2 Overexpression on Lifespan in *C. elegans* and *Drosphila*," *Nature*, 477:482 (2011).

Feige, J.N., et al., "DisSIRTing on LXR and Cholesterol Metabolism," *Cell Metabolism*, 6:343-345 (Nov. 2007).

Gabbi, C., et al., "Minireview: Liver X Receptor β: Emerging Roles in Physiology and Diseases," *Mol. Endocrinol.* 23(2): 129-136 (Feb. 2009).

Gayther et al., "Mutations truncating the EP300 acetylase in human cancers," *Nat. Genet.*, 24(3): 300-303 (2000).

GenBank Accession No. AI466061 (1999).

Gray and Ekstrom, "The human histone deacetylase family," *Exp. Cell Res.*, 262: 75-83 (2001).

Lambert et al., "Use of primary cultures of rat hepatocytes for the study of ageing and caloric restrictions," *Exp. Gerontol.*, 35(5): 583-594 (2000).

Ledford, H., "Longevity Genes Challenged," [on-line], Sep. 21, 2011, retrieved from the internet URL: http://www.nature.com/news/2011/110921/full/news.2011.549.html;doi:10.1038/news.2011.549.

Li, X. et al., Interventions in Aging and Age-Related Diseases: The Present and the Future, Age, 28(1):1-75 (Mar. 2006).

Lombard, D.B. et al., "Longevity Hits a Roadblock," Nature 477: 410-411 (2011).

Rizki, G. et al., "The Evolutionary Conserved Longevity Determinants HCF-1 and SIR2.11 Collaborate to Regulate DAF-15/FOXO," PLoS Genetics, 7(9): e1002235, 1-16 (2011).

Tissenbaum et al., "Regulation of *Caenorhabditis elegans* Lifespan by Sir-2.1 Transgenes," *Nature*, 477: E1-E2 (2011).

Viswanathan, M. et al., "A Role for SIR-2.1 Regulation of ER Stress Resonse Genes in Determining *C. elegans* Life Span," Development Cell, 9: 605-615 (2005).

Non-Final Office Action for U.S. Appl. No. 12/851,225; Date Mailed: Apr. 9, 2012.

Final Office Action for U.S. Appl. No. 10/993,903; Date Mailed: Mar. 28, 2012.

Final Office Action for U.S. Appl. No. 12/303,721; Date Mailed: Oct. 31, 2011.

Notice of Allowance for U.S. Appl. No. 12/408,575; Date Mailed: Mar. 15, 2012.

Final Office Action for U.S. Appl. No. 12/408,575; Date Mailed: Sep. 8, 2011.

Non-Final Office Action for U.S. Appl. No. 13/523,412; Date Mailed: Mar. 25, 2013.

Office Action for U.S. Appl. No. 12/209,847; Date Mailed: Jul. 25, 2011.

Office Action for U.S. Appl. No. 12/209,847; Date Mailed: Jul. 28, 2011.

U.S. Office Action dated Oct. 13, 2010 for U.S. Appl. No. 09/735,786.

U.S. Office Action dated Sep. 29, 2010 for U.S. Appl. No. 12/209,847.

U.S. Office Action dated Jul. 17, 2006 for U.S. Appl. No. 09/461,580.

U.S. Office Action dated Nov. 15, 2005 for U.S. Appl. No. 09/461,580.

U.S. Office Action dated Mar. 26, 2004 for U.S. Appl. No. 09/461,580.

U.S. Office Action dated Nov. 6, 2001 for U.S. Appl. No. 09/461,580.

U.S. Office Action dated Aug. 15, 2008 for U.S. Appl. No. 11/404,146.

U.S. Office Action dated Jan. 25, 2008 for U.S. Appl. No. 11/404,146.

U.S. Office Action dated Jun. 27, 2007 for U.S. Appl. No. 11/404,146.

Office Action for U.S. Appl. No. 10/191,121; Date Mailed: Dec. 15, 2004.

Office Action for U.S. Appl. No. 09/461,580; Date Mailed: Oct. 31, 2007.

Notice of Allowance for U.S. Appl. No. 09/461,580; Date Mailed: Aug. 8, 2008.

Office Action for U.S. Appl. No. 12/408,575; Date Mailed: Feb. 28, 2011.

* cited by examiner

FIG. 2D  hSIRT3  mafwgwraaaalrlwgrvverveagggvgp
         hSIRT4  mkmsfaltfrsakgrwianpsqpcskasiglf

US 8,546,090 B2

SIRT4 ACTIVITIES

RELATED APPLICATIONS

This application is a continuation of U.S. application Ser. No. 12/851,225, filed Aug. 5, 2010, now abandoned, which is a continuation of U.S. application Ser. No. 11/409,170, filed Apr. 21, 2006, now abandoned, which claims the benefit of U.S. Provisional Application No. 60/673,565, filed on Apr. 21, 2005. The entire teachings of the above applications are incorporated herein by reference.

GOVERNMENT FUNDING

This invention was made with government support under grant numbers R01 AG015339 and F32 AG022775 awarded by the National Institutes of Health. The government has certain rights in the invention.

INVENTION SUMMARY

In one aspect, the disclosure features a method of evaluating Sirt4 activity. The method includes providing a composition (e.g., a cell-free composition) that includes one or more of: a Sirt4 protein, an ADP-ribosyl donor, and a substrate; and evaluating ADP-ribosylation activity in the composition. The ADP-ribosyl donor can be NAD or an NAD analog, e.g., a labeled version of the donor, e.g., radio-labeled versions thereof, e.g., $^3$H, $^{14}$C, $^{32}$P- or $^{33}$P-labeled. ADP-ribosylation activity can be evaluated by detecting a radiolabel associated with the substrate, e.g., NAD. ADP-ribosylation activity can be evaluated by detecting the modification of the substrate or the ADP-ribosyl donor (e.g., NAD). The substrate can be separated from the composition prior to evaluation of ADP-ribosylation activity.

The substrate can include, e.g., glutamate dehydrogenase (GDH), aldehyde dehydrogenase (ADH), adenine nucleotide transporter (ANT) or a homolog thereof, or histones, or a fragment of any of the above. The substrate can be from a human or other mammal, e.g., a mouse, rat, pig, or cow. In one embodiment, the substrate includes a peptide, e.g., a peptide from a mitochondrial protein.

In one embodiment, the composition includes a test compound.

In one embodiment, the Sirt4 protein is at least 10% pure, e.g., 10%, 20%, 30%, 40%, 50%, 75%, 80%, 90%, 95%, or 99% pure. The Sirt4 protein can be expressed in recombinant cells and isolated therefrom. The Sirt4 protein can be expressed in, e.g., E. coli cells, and isolated therefrom. The concentration of the Sirt4 protein in the composition can be between 0.1 pM and 0.1 µM, e.g., between 0.1 pM and 10 pM, 10 pM and 1 nM, or 1 nM and 0.1 µM.

In one embodiment, the Sirt4 protein can include the core domain of Sirt4 or other biologically active portion of full-length Sirt4. The Sirt4 protein can include the core domain of Sirt4, but not all sequences of a full-length Sirt4. Alternatively, the Sirt4 protein can include a full-length Sirt4. The Sirt4 protein can include a sequence that is at least 85% identical, e.g., 85%, 90%, 95%, 98%, 99% identical, to SEQ ID NO:3 (an exemplary fragment of human Sirt4). The Sirt4 protein can include a sequence at least 85% identical, e.g., 85%, 90%, 95%, 98%, 99%, or 100% identical, to SEQ ID NO:1 (full-length human Sirt4) or can include one or more of a sequence at least 85% identical, e.g., 85%, 90%, 95%, 98%, 99%, or 100% identical, to amino acid residues 29-314, 29-308, 30-314, 36-308, 42-308, 42-300, or 36-314 of SEQ ID NO:1. The Sirt4 protein can be human. The Sirt4 protein can include an artificial mutation, e.g., an alanine-scanned mutation.

In another aspect, this disclosure features a method of evaluating Sirt4 activity in a cell. The method includes altering Sirt4 expression in an isolated cell and evaluating ADP-ribosylation activity associated with the cell. Sirt4 expression can be decreased, e.g., by introducing to the cell a nucleic acid that decreases expression, e.g., an siRNA. Sirt4 expression can be increased, e.g., by introducing to the cell a nucleic acid that encodes Sirt4 (e.g., a protein that includes a Sirt4 core domain) operably linked to a promoter that drives expression of Sirt4. The isolated cell can include an exogenous nucleic acid that includes a sequence encoding a Sirt4 protein. The isolated cell can be modified by introduction of an exogenous promoter into an endogenous Sirt4 encoding gene. The cell can be, e.g., a yeast cell or a mammalian cell, e.g., a pancreatic cell, brain cell, liver cell, adipose cell, muscle cell, skin cell, or kidney cell.

In one embodiment, the method further includes comparing the activity evaluated in the presence of the test compound with the Sirt4 activity evaluated in the absence of the test compound. In one embodiment, the method further includes evaluating the test compound in a cellular or animal model of insulin secretion, diabetes, or a neurodegenerative disorder, e.g., Alzheimer's disease.

In another aspect, this disclosure features a method of evaluating the effect of a test compound on Sirt4. The method includes providing a reaction mixture including a Sirt4 protein and a test compound, and evaluating an activity of Sirt4. In one embodiment, the activity of Sirt4 is an enzymatic activity, e.g., an ADP-ribosyltransferase activity. The reaction mixture can include NAD or an NAD analog. The NAD or NAD analog can be radiolabeled, e.g., with $^3$H, $^{14}$C, $^{32}$P or $^{33}$P. The reaction mixture can include an ADP-ribosylation substrate, e.g., GDH, aldehyde dehydrogenase (ADH), an adenine nucleotide transporter (ANT), or a histone.

In another embodiment, the activity of Sirt4 is a binding activity. The binding activity can be binding to the test compound or binding to a Sirt4 binding partner, e.g., GDH, adenine nucleotide transporter 1 or 2 (ANT), or insulin-degrading enzyme (IDE). The reaction mixture can include a Sirt4 binding partner, e.g., GDH, ANT, or IDE.

The test compound can be, e.g., a small molecule, a peptide, a protein, or an antibody. In one embodiment, the method is repeated for each of a plurality of test compounds from a chemical library.

In one embodiment, the Sirt4 protein is at least 10% pure, e.g., 10%, 20%, 30%, 40%, 50%, 75%, 80%, 90%, 95%, or 99% pure. The Sirt4 protein can be expressed in recombinant cells and isolated therefrom. The Sirt4 protein can be expressed in, e.g., E. coli cells, and isolated therefrom. The concentration of the Sirt4 protein in the composition can be between 0.1 pM and 0.1 µM, e.g., between 0.1 pM and 10 pM, 10 pM and 1 nM, or 1 nM and 0.1 µM.

In one embodiment, the Sirt4 protein includes the core domain of Sirt4. The Sirt4 protein can include the core domain of Sirt4, but not all sequences of a full-length Sirt4. Alternatively, the Sirt4 protein can include a full-length Sirt4. The Sirt4 protein can include a sequence that is at least 85% identical, e.g., 85%, 90%, 95%, 98%, 99% identical, to SEQ ID NO:3 (an exemplary fragment of human Sirt4). The Sirt4 protein can include a sequence at least 85% identical, e.g., 85%, 90%, 95%, 98%, 99% identical, to SEQ ID NO:1 (full-length human Sirt4) or amino acid residues 29-314, 29-308, 30-314, 36-308, 42-308, 42-300, or 36-314 of SEQ ID NO:1. The Sirt4 protein can be human. The Sirt4 protein can include an artificial mutation, e.g., an alanine scanned mutation. The Sirt4 protein can be a processed Sirt4 protein, e.g., a Sirt4 protein that lacks at least amino acids 1-14, 1-20, 1-27, or 1-28 of SEQ ID NO:1.

In one embodiment, the method further includes comparing the activity evaluated in the presence of the test compound with the Sirt4 activity evaluated in the absence of the test compound. In one embodiment, the method further includes evaluating the test compound in a cellular or animal model of insulin secretion, diabetes, or a neurodegenerative disorder, e.g., Alzheimer's disease.

In another aspect, this disclosure features a method of identifying a compound that alters a Sirt4-associated parameter in a cell. The method includes contacting a test compound to a cell that expresses Sirt4, and evaluating a Sirt4-associated parameter associated with the cell. The Sirt4-associated parameter can be expression of Sirt4, e.g., measured as levels of Sirt4 mRNA or protein. The Sirt4-associated parameter can be ADP-ribosylation activity, e.g., measured as ADP-ribosylation of a mitochondrial protein, e.g., GDH. The Sirt4-associated parameter can be binding of Sirt4 to a protein, e.g., a mitochondrial protein, e.g., GDH, ANT, or IDE. The Sirt4-associated parameter can be the subcellular localization of Sirt4, e.g., measured by immunofluorescence microscopy. The Sirt4-associated parameter can be a parameter indicative of mitochondrial function. The Sirt4-associated parameter can be the proteolytic modification state of Sirt4, e.g., an N-terminal proteolytic modification. The Sirt4-associated parameter can be a level of a primary or secondary metabolite.

The test compound can be, e.g., a small molecule, a peptide, a protein, or an antibody. In one embodiment, the method is repeated for each of a plurality of test compounds from a chemical library. The cell can be, e.g., a yeast cell or a mammalian cell, e.g., a pancreatic cell, brain cell, liver cell, adipose cell, muscle cell, skin cell, or kidney cell. A peptide is generally a polymer of less than 24 amino acids in length. Exemplary peptides include peptides between 3-24, 3-20, 3-12, 3-8, or 5-12 amino acids in length.

In one embodiment, the method further includes comparing the parameter evaluated in the presence of the test compound with the Sirt4-associated parameter evaluated in the absence of the test compound. In one embodiment, the method further includes evaluating the test compound in a cellular or animal model of insulin secretion, diabetes, or a neurodegenerative disorder, e.g., Alzheimer's disease, Parkinson's disease, or Huntington's disease or other neurological disorder.

In another aspect, this disclosure features a method of modulating insulin secretion in response to glucose. The method includes modulating the expression or activity of Sirt4 in an insulin-secreting cell. Insulin secretion can be increased, e.g., by decreasing the expression or activity of Sirt4. Insulin secretion can be decreased, e.g., by increasing the expression or activity of Sirt4. Insulin secretion can be modulated in vitro, e.g., in a cultured cell or tissue explant. Insulin secretion can be modulated in a subject, e.g., a mammal, e.g., a human, by administering an agent that modulates Sirt4 expression or activity.

In another aspect, this disclosure features an isolated cell including an RNA (e.g., a dsRNA, anti-sense RNA, or siRNA) that inhibits the expression of Sirt4. The cell can be a pancreatic cell, e.g., a pancreatic β-cell. The cell can be an insulin-secreting cell.

In another aspect, this disclosure features a method of treating or preventing diabetes or a diabetes-related disorder (e.g., pre-diabetes) by administering to a subject an agent that decreases the expression or activity of Sirt4 in an amount effective to treat or prevent diabetes or the diabetes-related disorder. The agent can be an agent identified by any of the screening methods described herein.

In another aspect, this disclosure features a method of treating or preventing a disorder, e.g., a metabolic disorder. The method includes administering to a subject an agent that modulates the expression or activity of Sirt4 in an amount effective to treat or prevent the disorder, e.g., the metabolic disorder. The metabolic disorder can be, e.g., diabetes, insulin resistance, metabolic syndrome (syndrome X), obesity, or pre-diabetes. The expression or activity of Sirt4 can be modulated in an insulin-secreting cell, e.g., a pancreatic β-cell. In one embodiment, the expression or activity of Sirt4 is decreased, thus increasing insulin secretion. In one embodiment, the expression or activity of Sirt4 is increased, thus decreasing insulin secretion. The agent can be an antagonistic nucleic acid that reduces Sirt4 expression, e.g., an siRNA that targets Sirt4.

A related method includes providing a composition that includes an agent that modulates expression or activity of Sirt4, evaluating an aliquot of the composition (e.g., using a method described herein), e.g., for ability of the aliquot to modulate expression or activity of Sirt4, and administering to a subject an agent that modulates the expression or activity of Sirt4 in an amount effective to treat or prevent the disorder, e.g., the metabolic disorder, or diabetes.

In another aspect, this disclosure features a method of treating or preventing a symptom of a neurodegenerative disorder, e.g., Alzheimer's disease, Parkinson's disease, or Huntington's disease, or other neurological disorder. The method includes administering to a subject a compound that increases the expression or activity of Sirt4 in an amount effective to treat or prevent the neurodegenerative disorder. The neurodegenerative disorder can be one, e.g., that involves accumulation of β-amyloid peptide.

In another aspect, this disclosure features a method that includes evaluating a Sirt4-associated parameter in a pancreatic cell, brain cell, or other Sirt4-expressing cell. The Sirt4-associated parameter can be an indicator of expression of Sirt4, levels of Sirt4 mRNA or protein, or ADP-ribosylation activity by Sirt4 protein. The Sirt4-associated parameter can be an indicator of ADP-ribosylation of a mitochondrial protein, e.g., GDH. The Sirt4-associated parameter can be an indicator of binding of Sirt4 to a Sirt4 binding partner, e.g., a mitochondrial protein, e.g., GDH, ANT, or IDE. For example, the Sirt4 binding partner is a human protein.

In another aspect, this disclosure features a method that includes evaluating a Sirt4-associated parameter in mitochondria, e.g., isolated mitochondria. The Sirt4-associated parameter can be an indicator of levels of Sirt4 protein, or ADP-ribosylation activity by Sirt4 protein. The Sirt4-associated parameter can be an indicator of ADP-ribosylation of a mitochondrial protein, e.g., GDH. The Sirt4-associated parameter can be an indicator of binding of Sirt4 to a Sirt4 binding partner, e.g., GDH, ANT, or IDE. The Sirt4-associated parameter can be mitochondrial function.

In another aspect, this disclosure features a method that includes evaluating the ADP-ribosylation state of glutamate dehydrogenase in a pancreatic cell, brain cell, or other Sirt4-expressing cell. The cells can include human cells.

In another aspect, this disclosure features an antibody that binds to Sirt4, e.g., human Sirt4, and distinguishes between mature, processed Sirt4, e.g., human Sirt4, and unprocessed Sirt4, e.g., human Sirt4. The antibody can bind preferentially to mature, processed Sirt4, relative to unprocessed Sirt4. For example, the antibody binds to amino acid residues 29-32 of a Sirt4 whose N-terminus begins at a residue corresponding to residue 29 of SEQ ID NO:1. The antibody can bind preferentially to unprocessed Sirt4, relative to mature, processed Sirt4. For example, the antibody binds to an epitope within amino acid residues 1-28 of SEQ ID NO:1.

In another aspect, this disclosure features a method that includes processing state of Sirt4, e.g., in the N-terminal region, e.g., to determine if one or more amino acids from amino acid residues 1-28 of SEQ ID NO:1 are present or absent. The method can be used to evaluate a sample that includes Sirt4. The sample can include, or contain, e.g., a cell, a cell-free extract, or mitochondria, e.g., isolated mitochondria. The method can include determining the N-terminal sequence of Sirt4, the sequence of one or more amino acids in the N-terminal 20% of the protein, or the size of peptide fragments of Sirt4 (e.g., using mass spectroscopy and optionally proteolysis). The method can include contacting the sample to an antibody that binds to Sirt4, e.g., human Sirt4, and distinguishes between mature, processed Sirt4, e.g., human Sirt4, and unprocessed Sirt4, e.g., human Sirt4. The sample can include a pancreatic cell, brain cell, or other Sirt4-expressing cell. The sample can include human cells.

In another aspect, this disclosure features a method of directing expression of a target sequence to an insulin-producing cell. The method includes providing a pancreatic cell that contains a nucleic acid that includes regulatory sequences from the SIRT4 gene operably linked to a target sequence for expression, wherein the target sequence is not a sequence from the Sirt4 gene. The target sequence can encode a protein, e.g., insulin or another secreted protein. The target sequence can encode an anti-sense nucleic acid.

In another aspect, this disclosure features a method of isolating a Sirt4 protein. The method includes isolating mitochondria from a cell that expresses a Sirt4 protein and separating the Sirt4 from at least one other mitochondrial protein. The Sirt4 protein can be proteolytically processed. The cell can be a human cell.

In another aspect, this disclosure features a method of isolating a Sirt4 protein. The method includes isolating mitochondria from a cell that expresses a Sirt4 protein and separating the Sirt4 from at least one other mitochondrial protein. The Sirt4 protein can be proteolytically processed.

In another aspect, this disclosure features a kit including a Sirt4 protein and an ADP-ribosylation substrate, e.g., GDH. The kit can further include an ADP-ribosyl donor, e.g., NAD or an NAD analog.

In one aspect, the invention features a method that includes genotyping a human gene that encodes a sirtuin, e.g., SIRT4 or another SIRT4 and recording information about the genotype in association with information about a metabolic disorder, e.g., diabetes, pre-diabetes, or hyperinsulinemia, or other disorder described herein (including, e.g., neurological disorders).

The invention also features a method that includes genotyping a human gene that encodes a sirtuin, e.g., SIRT4 or another SIRT4 and recording information about the genotype in association with information about a metabolic disorder or other disorder described herein.

In one aspect, the invention features a method that includes a) determining the identity of at least one nucleotide in the SIRT4 locus on human chromosome 12q of a subject; and b) creating a record which includes information about the identity of the nucleotide and information relating to a metabolic disorder, e.g., diabetes, or other disorder described herein, e.g., a disorder-related parameter of the subject, wherein the a metabolic disorder (e.g., diabetes, or other disorder described herein) is other than the genotype of a nucleotide in the 12q region. The method can be used, e.g., for gathering genetic information.

In one embodiment, the determining includes evaluating a sample including human genetic material from the subject.

Another method includes: a) evaluating a parameter of a SIRT4 molecule from a mammalian subject; b) evaluating a parameter associated with a metabolic disorder, e.g., diabetes, or other disorder described herein of the subject wherein the parameter is other than a parameter of a SIRT4 molecule; and c) recording information about the SIRT4 parameter and information about the parameter, wherein the information about the parameter and information about the phenotypic trait are associated with each other in the database. For example, the parameter is a phenotypic trait of the subject.

In one embodiment, the SIRT4 molecule is a polypeptide and the SIRT4 parameter includes information about a SIRT4 polypeptide. In another embodiment, the SIRT4 molecule is a nucleic acid and the SIRT4 parameter includes information about identity of a nucleotide in the SIRT4 gene.

In an embodiment, the subject is an embryo, blastocyst, or fetus. In another embodiment, the subject is a post-natal human, e.g., a child or an adult (e.g., at least 20, 30, 40, 50, 60, 70 years of age).

In one embodiment, step b) is performed before or concurrent with step a). In one embodiment, the human genetic material includes DNA and/or RNA.

The method can further include comparing the SIRT4 parameter to reference information, e.g., information about a corresponding nucleotide from a reference sequence. For example, the reference sequence is from a reference subject, e.g., a subject who has a common allele, especially one who is homozygous for a common allele. In another embodiment, the reference sequence is from a reference subject that has a metabolic disorder, e.g., diabetes, e.g., early or late-onset diabetes, or other disorder described herein.

In one embodiment, the method further includes comparing the nucleotide to a corresponding nucleotide from a genetic relative or family member (e.g., a parent, grandparent, sibling, progeny, prospective spouse, etc.).

In one embodiment, the method further includes evaluating risk or determining diagnosis of a metabolic disorder, e.g., diabetes, or other disorder described herein in the subject as a function of the genotype.

In one embodiment, the method further includes recording information about the SIRT4 parameter and parameter, e.g., in a database. For example, the information is recorded in linked fields of a database (e.g., SIRT4 parameter is linked to at least one of: corresponding SIRT4 parameter and/or data regarding comparison with the reference sequence). The nucleotide can be located in an exon, intron, or regulatory region of the SIRT4 gene. For example, the nucleotide is a SNP. The identity of at least one SNP from Table 1 can be evaluated. In one embodiment, a plurality of nucleotides (e.g., at least 10, 20, 50, 100, 500, or 1000 nucleotides are evaluated (e.g., consecutive or non-consecutive)) in the SIRT4 locus are evaluated. In another embodiment, a single nucleotide is evaluated.

In one embodiment, the method includes one or more of: evaluating a nucleotide position in the SIRT4 locus on both chromosomes of the subject; recording the information (e.g., as phased or unphased information); aligning the genotyped nucleotides of the sample and the reference sequence; and identifying nucleotides that differ between the subject nucleotides and the reference sequence.

The method can be repeated for a plurality of subjects (e.g., at least 10, 25, 50, 100, 250, 500 subjects).

In one embodiment, the method can include comparing the information of step a) and step b) to information in a database, and evaluating the association of the genotyped nucleotide(s) with a metabolic disorder, e.g., diabetes, or other disorder described herein.

In another aspect, the disclosure features a protein, e.g., an isolated protein, that includes a Sirt4 core domain, but that does not include all or part of the Sirt4 leader sequence. For example, the protein can be lacking at least amino acids that correspond to 1-14, 1-20, 1-26, 1-27, or 1-28 of SEQ ID NO:1, e.g., such amino acids of SEQ ID NO:1 itself. The protein may include another amino acid or another amino acid sequence, e.g., amino terminal to the remaining region of SIRT4. For example, there may be a methionine immediately amino terminal to residue 29 of SEQ ID NO:1, a tag sequence, or a heterologous leader sequence.

The protein can be recombinantly produced, e.g., from $E.$ $coli$. The protein can be provided in a preparation that is substantially free of mitochondrial proteins. In some embodiments, the preparation includes one, but not more than five species of mitochondrial proteins.

An "isolated" or "purified" polypeptide or protein is separated from at least some cellular material or other contaminating proteins from the cell or tissue source from which the protein is derived, or substantially free from chemical precursors or other chemicals when chemically synthesized. An isolated protein can be substantially free of contaminating materials. "Substantially free" means that the protein of interest in the preparation is at least 10% pure. In an embodiment, the preparation of the protein has less than about 30%, 20%, 10% and more preferably 5% (by dry weight), of a contaminating component (e.g., a protein not of interest, chemical precursors, and so forth). When the protein or biologically active portion thereof is recombinantly produced, it is also preferably separated from culture medium, e.g., culture medium represents less than about 20%, more preferably less than about 10%, and most preferably less than about 5% of the volume of the protein preparation. Exemplary preparations of proteins described herein include isolated or purified preparations of at least 0.01, 0.1, 1.0, and 10 milligrams in dry weight.

A "non-essential" amino acid residue is a residue that can be altered from the wild-type sequence of protein without abolishing or substantially altering activity, e.g., the activity is at least 20%, 40%, 60%, 70% or 80% of wild-type. An "essential" amino acid residue is a residue that, when altered from the wild-type sequence results in abolishing activity such that less than 20% of the wild-type activity is present. Conserved amino acid residues are frequently predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a protein is preferably replaced with another amino acid residue from the same side chain family. Alternatively, in another embodiment, mutations can be introduced randomly along all or part of a coding sequence, such as by saturation mutagenesis, and the resultant mutants can be screened for biological activity to identify mutants that retain activity. Following mutagenesis, the encoded protein can be expressed recombinantly and the activity of the protein can be determined.

As used herein, a "biologically active portion" of a protein includes a fragment of a protein of interest, e.g., a target protein, which participates in an interaction, e.g., an intramolecular or an inter-molecular interaction, e.g., a binding or catalytic interaction. An inter-molecular interaction can be a specific binding interaction or an enzymatic interaction (e.g., the interaction can be transient and a covalent bond is formed or broken). An inter-molecular interaction can be between the protein and another protein, between the protein and another compound, or between a first molecule and a second molecule of the protein (e.g., a dimerization interaction). Biologically active portions of a protein include peptides comprising amino acid sequences sufficiently homologous to or derived from the amino acid sequence of the protein which include fewer amino acids than the full length, natural protein, and exhibit at least one activity of the natural protein.

Biologically active portions can be identified by a variety of techniques including truncation analysis, site-directed mutagenesis, and proteolysis. Mutants or proteolytic fragments can be assayed for activity by an appropriate biochemical or biological (e.g., genetic) assay. In some embodiments, a biologically active portion is folded, e.g., the portion includes one or more folded domains, e.g., independently folded domains.

Exemplary biologically active portions can include at least a minimal enzymatic core domain that has an active site and detectable enzymatic activity in vitro.

Exemplary biologically active portions include between 5-100% of a protein, e.g., between 10-99, 10-95, 15-94, 15-90, 20-90, 25-80, 25-70, 25-60, 25-50, 25-40, 5-25, or 75-90% of the protein, e.g. a target protein. Biologically active portions can include, e.g., internal deletions, insertions (e.g., of a heterologous sequence), terminal deletions, and substitutions (e.g., conservative substitutions). Typically, biologically active portions comprise a domain or motif with at least one activity of the protein.

The terms "modulated" and "differentially regulated" include increasing (including, for example, activation or stimulation) and decreasing (including, for example, inhibition or suppression) relative to a reference level.

The details of one or more embodiments are set forth in the accompanying drawings and the description below. Other features, objects, and advantages of the invention will be apparent from the description and drawings, and from the claims.

BRIEF DESCRIPTION OF THE DRAWINGS

FIG. 1. Sirt4 is an ADP-ribosyltransferase.

FIG. 4. The role of Sirt4 in insulin secretion.

FIG. 5A. Mitochondria (50 mg) from 293T cells were incubated with [$^{32}$P]-NAD at 37° C. for 30 min. Proteins were separated by SDS-PAGE, transferred to a nitrocellulose membrane, and radioactivity was measured by exposure to film. FIG. 5B. Mitochondrial proteins were ADP-ribosylated as described for FIG. 5A, and lysis was performed in NP-40 buffer containing 10 mM DTT and 0.5 mM EDTA. Clarified lysate was incubated with protein A resin that had been pre-incubated with antibodies against hSirt4, ANT or glutamate dehydrogenase (GDH). FIG. 5C. 293T cells were transiently transfected with 10 μg of pCMV (V) or phSirt4-FLAG (4). Cells were harvested and lysed in NP-40 buffer containing protease inhibitors and 1 mM DTT. The clarified lysate was incubated for 2 h at 4° C., while rotating, with resin that had been pre-incubated with antibodies for Gal4, FLAG, hSirt4, or GDH. The resin was washed six times with lysis buffer and protein complexes were subjected to western blot analysis using antibodies against FLAG or GDH. FIG. 5D. An endogenous interaction between Sirt4 and glutamate dehydrogenase was determined in MIN6 cells. 5-10 cm plates of MIN6 cells were harvested and lysed as described above. Lysates were incubated with resin pre-incubated with antibodies for mSirt4 or Gal4. Protein complexes were subjected to western blot analysis using antibodies for mSirt4 or GDH. FIG. 5E. The effect of Sirt4 overexpression on glutamate dehydrogenase ADP-ribosylation was investigated in 293T cells that were transiently transfected with hSirt4-FLAG. Mitochondria were labeled with [$^{32}$P]-NAD, and then proteins were immunoprecipitated using antibodies against FLAG or GDH. Proteins were separated by SDS-PAGE, transferred to nitrocellulose membrane, and the radioactivity was measured by exposure to x-ray film.

FIG. 6. Glutamate dehydrogenase inhibition by Sirt4.

FIG. 7A. MIN6 cells were co-infected with RNAi for Sirt4 and glutamate dehydrogenase, and protein levels were compared to control infections. FIG. 7B. Insulin secretion assays were performed in double-infected or control cells as described previously. FIG. 7C. Insulin secretion assays were performed in control or Sirt4 RNAi treated cells in the presence or absence of BCH, an activator of glutamate dehydrogenase.

FIG. 8. ATP and respiration in Sirt4 RNAi treated cells.

DETAILED DESCRIPTION OF THE INVENTION

Figure 1D:
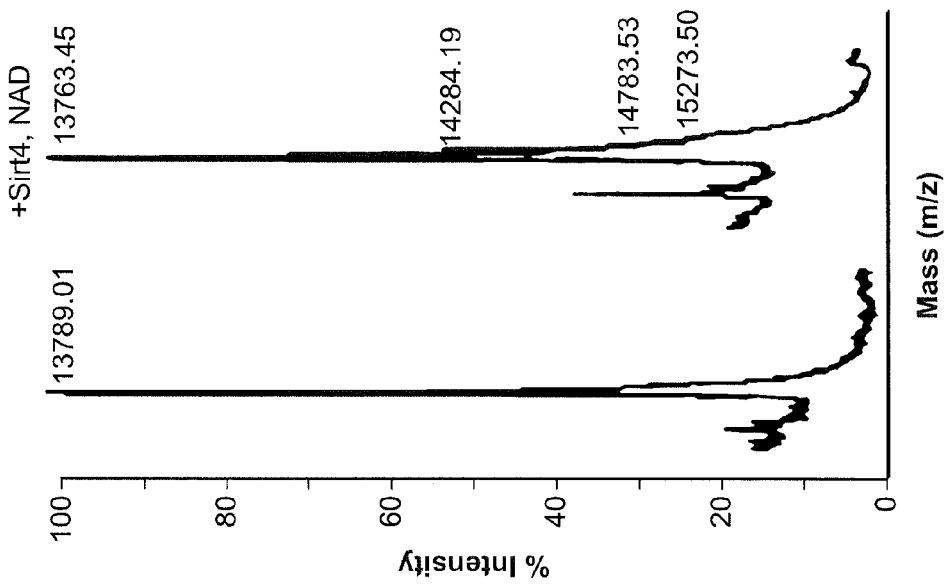
FIG. 1D. Mass spectrometry was used to analyze histone 2A protein that was incubated for 30 min at 37° C. in the presence of 1 mM NAD+ with or without Sirt4.

Sirt4 is a mitochondrial protein. It interacts with glutamate dehydrogenase, insulin degrading enzyme and an adenine nucleotide transporter, and can regulate insulin secretion. Agents that modulate the expression or activity of Sirt4, e.g., agents described herein or identified by the methods described herein, can be useful in treating or preventing metabolic disorders, e.g., the metabolic syndrome, obesity, elevated cholesterol, or diabetes (e.g., type 1 diabetes mellitus or type 2 diabetes mellitus); and neurodegenerative disorders, e.g., Alzheimer's disease, as well as other disorders.

Sirt4 Proteins

The Sirt4 proteins belong to the sirtuin family, proteins identified as sharing significant sequence identity to *Saccharomyces cerevisiae* SIR2.

As used herein, the term "Sirt4" or "Sirt4 protein" refers to proteins, e.g., eukaryotic proteins, e.g., mammalian proteins, comprising a conserved core domain classified in the Conserved Domain Database group cd01049 (SIRT4) (Marchler-Bauer et al. (2005) *Nucleic Acids Res.* 33: D192-6), functional domains, fragments (e.g., functional fragments), e.g., fragments of at least 8 amino acids, e.g., at least 8, 18, 28, 64, 128, 150, 180, 200, 220, 240, 260, or 280 amino acids, and variants thereof. Exemplary Sirt4 proteins include those designated GenBank NP_036372 (human Sirt4) and Q8R216 (mouse Sirt4). Homologs of Sirt4 proteins will share 60%, 80%, 85%, 90%, 95%, 98%, 99% sequence identity to a known Sirt4 protein and, e.g., feature ADP-ribosyltransferase activity. Eukaryotic Sirt4 proteins may be localized, e.g., to mitochondria.

An exemplary human Sirt4 sequence (NP_036372) is as follows:

(SEQ ID NO: 1)
MKMSFALTFRSAKGRWIANPSQPCSKASIGLFVPASPPLDPEKVKELQR

FITLSKRLLVMTGAGISTESGIPDYRSEKVGLYARTDRRPIQHGDFVRS

APIRQRYWARNFVGWPQFSSHQPNPAHWALSTWEKLGKLYWLVTQNVDA

LHTKAGSRRLTELHGCMDRVLCLDCGEQTPRGVLQERFQVLNPTWSAEA

HGLAPDGDVFLSEEQVRSFQVPTCVQCGGHLKPDVVFFGDTVNPDKVDF

VHKRVKEADSLLVVGSSLQVYSGYRFILTAWEKKLPIAILNIGPTRSDD

LACLKLNSRCGELLPLIDPC

An exemplary mouse Sirt4 sequence (Q8R216) is as follows:

(SEQ ID NO: 2)
MSGLTFRPTKGRWITHLSRPRSCGPSGLFVPPSPPLDPEKIKELQRFIS

LSKKLLVMTGAGISTESSIPDYRSEKVGLYARTDRRPIQHIDFVRSAPV

RQRYWARNFVGWPQFSSHQPNPAHWALSNWERLGKLHWLVTQNVDALHS

KAGSQRLTELHGCMHRVLCLNCGEQTARRVLQERFQALNPSWSAEAQGV

APDGDVFLTEEQVRSFQVPCCDRCGGPLKPDVVFFGDTVNPDKVDFVHR

RVKEADSLLVVGSSLQVYSGYRFILTAREQKLPIAILNIGPTRSDDLAC

LKLDSRCGELLPLIDPRRQHSDVQRLEMNFPLSSAAQDP

Sirt4 is post-translationally processed to form mature Sirt4 by cleavage of the N-terminus after serine 28 of SEQ ID NO:1 (underlined). The N-terminus of SEQ ID NO:2 is predicted to be similarly cleaved (underlined).

The conserved Sirt4 core domain of human Sirt4 (SEQ ID NO:3) includes about amino acids 47-308 of SEQ ID NO:1. That of murine Sirt4 includes about amino acids 44-305 of SEQ ID NO:2. Other exemplary fragments of human Sirt4 include: 29-314, 29-308, 30-314, 36-308, 42-308, 42-300, and 56-314.

Human and mouse Sirt4 share about 89% sequence identity within this conserved core domain. It is also possible to make chimeric proteins that include one or more segments from human Sirt4 and one or more segments from mouse Sirt4. Such chimeras, for example, will include a number of proteins that are between 89% to 100% identical to human or mouse Sirt4.

Some simple examples include proteins that have an N-terminal half from one of the two species and a C-terminal half from the other. The switch over point can be located at an amino acid residue between about 5-10, 10-20, 20-30, 30-40, 40-50, 50-60, 60-70, 70-80, 80-90, or 90-95% of the length of human Sirt4.

A fragment of full length Sirt4 can have at least one function of Sirt4 protein and/or be folded. Functional fragments can, for example, have ADP-ribosyltransferase activity and/or ability to interact with a Sirt4 binding partner, e.g., glutamate dehydrogenase (GDH), adenine nucleotide transporter 1 or 2 (ANT), or insulin-degrading enzyme (IDE).

Variants of Sirt4 proteins can be produced by standard means, including site-directed and random mutagenesis. Preferably, amino acid 61 is a threonine, amino acid 70 is a glycine, amino acid 71 is an isoleucine, amino acid 144 is an asparagine, or amino acid 146 is an aspartic acid.

Assays

This disclosure includes methods for evaluating Sirt4, including Sirt4 enzymatic activity. One general category of methods including evaluating, directly or indirectly, ADP ribosylation activity of a Sirt4 protein. The protein can be a full length Sirt4 protein, a fragment thereof, or other variant thereof.

Detection of ADP ribosylation activity can be used to evaluate artificial or naturally occurring variants of a Sirt4 protein. In a first exemplary implementation, a Sirt4 genomic nucleic acid or mRNA (e.g., as cDNA) is amplified from a subject (e.g., a human subject. Protein encoded by the nucleic acid is evaluate for ADP ribosylation activity. In a second exemplary implementation, a Sirt4 gene is subjected to artificial mutagenesis to produce varied nucleic acids. One or more Sirt4 proteins encoded by such nucleic acids are evaluated for ADP ribosylation activity. Examples of artificial mutagenesis include random point mutagenesis, site-directed mutagenesis (e.g., alanine scanning), DNA shuffling, and partial exonuclease treatment.

It is also possible to evaluate Sirt4 activity in the presence of a test compound or test condition. The method can be used to screen a collection of compounds, e.g., a chemical library of small molecules. The method can also be used to evaluate a single compound, e.g., a quality control step, e.g., for a pharmaceutical or other product.

One exemplary method includes providing a reaction mixture that includes Sirt4 and a test compound, and evaluating an activity of Sirt4. Another exemplary method includes contacting a test compound to a cell that expresses Sirt4 and evaluating a Sirt4 parameter, e.g., expression or activity, in the cell. In some embodiments, in initial rounds of screening, it is possible to use mixtures (e.g., pools) of different compounds.

The activity of Sirt4 can be assayed, e.g., in the presence of a compound. Exemplary "Sirt4 activities" include ADP-ribosyltransferase function (e.g., ability to ADP-ribosylate a substrate, e.g., glutamate dehydrogenase, aldehyde dehydrogenase, or a histone); and interaction with a Sirt4 binding partner, e.g., physical association with a Sirt4 binding partner such as glutamate dehydrogenase (GDH), insulin degrading enzyme (IDE), or adenine nucleotide translocase (ANT), or fragments thereof.

In one aspect, the effect of a test compound on Sirt4 activity is evaluated by providing a reaction mixture that includes Sirt4 and the test compound, and evaluating an activity of Sirt4. The reaction mixture can include nicotinamide adenine nucleotide (NAD) or an NAD-like compound, e.g., comprising a radioactive isotope, e.g., $^{32}P$, $^{33}P$, $^{14}C$, $^{3}H$. An "NAD-like compound" refers to a compound (e.g., a synthetic or naturally occurring chemical, drug, protein, peptide, small organic molecule) that possesses structural similarity to component groups of NAD (e.g., adenine, ribose and phosphate groups) or functional similarity (e.g., oxidation of substrates, supports ADP-ribosylation of a histone in the presence of Sir2). For example, NAD-like compounds can be NADH, NADP, NADPH, 3-aminobenzamide or 1,3-dihydroisoquinoline (Vaziri et al. (1997) *EMBO J.* 16:6018-6033), nicotinamide, iso-nicotinamide, non-hydrolyzable NAD, biotinylated NAD, and fluorescent analogs of NAD (e.g., 1,N6-ethenoNAD).

A parameter associated with Sirt4 can be evaluated, e.g., in the presence or absence of a test compound. Exemplary Sirt4-associated parameters include transcription of Sirt4 mRNA, levels of Sirt4 mRNA, levels of Sirt4 protein, ADP-ribosylation activity of Sirt4, levels of ADP-ribosylation of mitochondrial proteins (e.g., glutamate dehydrogenase), activity of Sirt4-regulated proteins (e.g., glutamate dehydrogenase activity, measured by monitoring NADH absorption at 340 nm), binding of Sirt4 to Sirt4-binding partners (e.g., GDH, ANT, and IDE), bound vs. unbound state of Sirt4-associated proteins, and mitochondrial function, monitored by measuring respiration and ATP production. Other parameters that can be evaluated include qualitative or quantitative measures of insulin secretion, insulin levels, β-amyloid levels, β-amyloid degradation activity, or levels of other biomolecules including primary and secondary metabolites, e.g., small molecules, carbohydrates (e.g., glucose), peptides, lipids, or lipoproteins (e.g., low density lipoproteins, high density lipoproteins). The primary and secondary metabolites assayed can be endogenous, or as a result of the administration of a compound. Sirt4-associated parameters can be evaluated singly or in combination, e.g., to form a profile.

The assays described herein can also be adapted for other sirtuin proteins, e.g., sirtuins other than Sirt4.

Proteins described herein can be made by recombinant or other methods. See, e.g., techniques described in Sambrook & Russell, Molecular Cloning: A Laboratory Manual, 3rd Edition, Cold Spring Harbor Laboratory, N.Y. (2001). The proteins can be purified, e.g., using purification tags and other standard methods. See, e.g., techniques described in Scopes (1994) Protein Purification: Principles and Practice, New York: Springer-Verlag.

ADP-Ribosyltransferase Activity

ADP-ribosylation results in the transfer of one adenosine diphosphate ribose group from a donor (e.g., NAD) to an amino acid residue (e.g., cysteine, threonine) of a substrate (e.g., glutamate dehydrogenase, aldehyde dehydrogenase, or a histone). An ADP-ribosyltransferase is an enzyme (e.g. a protein or polypeptide) that can catalyze an ADP-ribosylation reaction.

For example, it is possible to monitor the addition of ADP from a [$^{32}$P]-NAD to a substrate (e.g., glutamate dehydrogenase, aldehyde dehydrogenase, or histones). In one embodiment, the ADP-ribosyltransferase activity is evaluated by providing a protein to be evaluated (about 0-1 µg) (e.g., a Sirt4 protein) to a reaction buffer comprising, e.g., 50 mM Tris-HCl, pH 8.0, 4 mM MgCl$_2$, 0.2 mM DTT, 1 µM cold or nonradiolabeled NAD, 0.08 µM [$^{32}$P]-NAD, and admixing or gently vortexing to dilute, resuspend, or mix the protein. Substrates (e.g., glutamate dehydrogenase, aldehyde dehydrogenase, or histones, about 0-1 µg) are then added, and the reaction mixture is incubated at ambient temperature (18-25° C.) for 30-120 minutes. The presence or absence of ADP-ribosylation products (e.g., ADP-ribosylated proteins) is detected, e.g., using autoradiography. The amount of ADP-ribosylation, for example, in the presence and absence of an agent to be tested, can be determined using suitable techniques, including, but not limited to, densitometric scanning of autoradiographs or phosphoimaging techniques of gels. (See Ausubel et al., *Current Protocols in Molecular Biology*, John Wiley & Sons (1999).)

Confirmation of ADP-ribosylation of substrates and, thus, ADP-ribosyltransferase activity of an agent can be performed, for example, by adding a suitable amount of snake venom phosphodiesterase (e.g., 2 mg/ml, specific activity 1.5 U/mg) to the resulting product of the reaction mixture described above. The reaction product and phosphodiesterase are incubated at about 37° C. for about an hour. Absence of an autoradiographic band following phosphodiesterase digestion, as compared with presence of an autoradiographic band in the absence of digestion, indicates that the substrate was ADP-ribosylated. ADP-ribosyltransferase activity can also be verifies by the addition of one or more specific ADP-ribosylation inhibitors, including, but not limited to, novobiocin and coumermycin A1, to in vitro assays described above. The inhibitor(s) can be added before or after the addition of the substrate. The absence of a band in an autoradiograph following the addition of a specific ADP-ribosylation inhibitor indicates that the agent has ADP-ribosyltransferase activity.

Exemplary substrates include, e.g., glutamate dehydrogenase (GDH), aldehyde dehydrogenase (ADH), adenine nucleotide transporter (ANT) and its homologs, e.g., mitochondrial carrier proteins, or histones, or a fragment of any of the above. Substrates can be obtained from any species of organism, including human, murine, or other mammal, other animals (e.g., nematode, fruit fly), or other organism, e.g., yeast. In one embodiment, the substrate is obtained from the same species as the SIRT4 protein.

The fragment can be conserved, e.g., at or near the ADP ribosylation site. Exemplary fragments of human GDH include: a fragment from a region of about 1-50, 50-100, 100-150, 150-200, 250-300, 300-350, 350-400, 400-450, 450-500, or 500-550.

Interaction Assays

In some embodiments, interaction with (e.g., binding to) Sirt4 can be assayed, e.g., in vitro or in a cell. The reaction mixture can include, e.g., a co-factor such as NAD and/or a NAD analog, a substrate or other binding partner or potentially interacting fragment thereof. Exemplary binding partners include GDH, IDE, ANT, or interacting fragments thereof. Preferably the binding partner is a direct binding partner.

In other embodiments, the reaction mixture can include a Sirt4 binding partner, and compounds can be screened, e.g., in an in vitro assay, to evaluate the ability of a test compound to modulate interaction between a Sirt4 and a Sirt4 binding partner. This type of assay can be accomplished, for example, by coupling one of the components with a radioisotope or enzymatic label such that binding of the labeled component to the other can be determined by detecting the labeled compound in a complex. A component can be labeled with $^{125}$I, $^{35}$S, $^{33}$P, $^{32}$P, $^{14}$C, or $^{3}$H, either directly or indirectly, and the radioisotope detected by direct counting of radioemmission or by scintillation counting. Alternatively, a component can be enzymatically labeled with, for example, horseradish peroxidase, alkaline phosphatase, or luciferase, and the enzymatic label detected by determination of conversion of an appropriate substrate to product. Competition assays can also be used to evaluate a physical interaction between a test compound and a target.

Cell-free assays involve preparing a reaction mixture of the target protein (e.g., Sirt4) and the test compound under conditions and for a time sufficient to allow the two components to interact and bind, thus forming a complex that can be removed and/or detected.

The interaction between two molecules can also be detected, e.g., using a fluorescence assay in which at least one molecule is fluorescently labeled. One example of such an assay includes fluorescence energy transfer (FET or FRET for fluorescence resonance energy transfer) (see, for example, U.S. Pat. Nos. 5,631,169; 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FET binding event can be conveniently measured through standard fluorometric detection means well known in the art (e.g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP. See, e.g., Nasir et al. (1999) *Comb Chem HTS* 2:177-190; Jameson et al. (1995) *Methods Enzymol* 246:283; Seethala et al. (1998) *Anal Biochem.* 255:257. Fluorescence polarization can be monitored in multiwell plates, e.g., using the POLARION™ reader (Tecan, Maennedorf, Switzerland). See, e.g., Parker et al. (2000) *J Biomolecular Screening* 5:77-88; and Shoeman, et al. (1999) *Biochem* 38:16802-16809.

In another embodiment, evaluating binding of a Sirt4 protein to a compound can include a real-time monitoring of the binding interaction, e.g., using Biomolecular Interaction Analysis (BIA) (see, e.g., Sjolander and Urbaniczky (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, Sirt4 protein is anchored onto a solid phase. The Sirt4/test compound complexes anchored on the solid phase can be detected at the end of the reaction, e.g., the binding reaction. For example, Sirt4 protein can be anchored onto a solid surface, and the test compound, (which is not anchored), can be labeled, either directly or indirectly, with detectable labels discussed herein.

It may be desirable to immobilize either Sirt4 protein or a Sirt4 binding partner to facilitate separation of complexed from uncomplexed forms of one or both of the proteins, as well as to accommodate automation of the assay. Binding of a test compound to Sirt4, or interaction of Sirt4 with a second component in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/mammalian homolog of a SIR2 fusion proteins or glutathione-S-transferase/target fusion proteins can be adsorbed onto glutathione SEPHAROSE® beads (Sigma Chemical, St. Louis, Mo.) or glutathione derivatized microtiter plates, which are then combined with the test compound or the test compound and either the non-adsorbed target protein or Sirt4, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of Sirt4 binding or activity determined using standard techniques.

Other techniques for immobilizing either Sirt4 or a target molecule on matrices include using conjugation of biotin and streptavidin. Biotinylated Sirt4 or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface, e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with Sirt4 or target molecules, but which do not interfere with binding of Sirt4 to its target molecule. Such antibodies can be derivatized to the wells of the plate, and unbound target or Sirt4 trapped in the wells by antibody conjugation. Methods for detecting such complexes, in addition to those described above for the GST-immobilized complexes, include immunodetection of complexes using antibodies reactive with Sirt4 or the target molecule, as well as enzyme-linked assays which rely on detecting an enzymatic activity associated with Sirt4 or the target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. *Current Protocols in Molecular Biology* 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting Sirt4 or a biologically active portion thereof with a known compound which binds Sirt4 to form an assay mixture, contacting the assay mixture with a test compound, and determining the ability of the test compound to interact with Sirt4, wherein determining the ability of the test compound to interact with Sirt4 includes determining the ability of the test compound to preferentially bind to Sirt4 or a biologically active portion thereof, or to modulate the activity of a target molecule, as compared to the known compound.

Sirt4 can, in vivo, interact with one or more cellular macromolecules, such as proteins. Such cellular macromolecules are referred to herein as "Sirt4 binding partners." Exemplary Sirt4 binding partners include GDH, ANT, and IDE. Compounds that disrupt such interactions can be useful in regulating the activity of Sirt4. Such compounds can include, but are not limited to molecules such as antibodies, peptides, and small molecules. Compounds that disrupt binding can themselves interact with Sirt4 protein or with a Sirt4 binding partner.

To identify compounds that modulate (e.g., interfere with) the interaction between the target product and its binding partner(s), for example, a reaction mixture containing the target product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target and its cellular or extracellular binding partner. Control reaction mixtures are incubated without the test compound or with a placebo. The formation of any complexes between the target product and the cellular or extracellular binding partner is then detected. The formation of a complex in the control reaction, but not in the reaction mixture containing the test compound, indicates that the compound interferes with the interaction of the target product and the interactive binding partner. Additionally, complex formation within reaction mixtures containing the test compound and normal target product can also be compared to complex formation within reaction mixtures containing the test compound and mutant target product. This comparison can be important in those cases wherein it is desirable to identify compounds that disrupt interactions of mutant but not normal target products.

These assays can be conducted in a heterogeneous or homogeneous format. Heterogeneous assays involve anchoring either the target product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target product or the partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment, a homogeneous assay can be used. For example, a preformed complex of the target product and the interactive cellular or extracellular binding partner product is prepared in that either the target products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target product-binding partner interaction can be identified.

In yet another aspect, Sirt4 can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other Sirt4 binding proteins that may be involved in Sirt4 activity. In one embodiment, the two-hybrid assay is used to monitor an interaction between two components, e.g., Sirt4 and, e.g., GDH, ANT, IDE, or fragments thereof. The two hybrid assay can also be conducted in the presence of a test compound, and the assay is used to determine whether the test compound enhances or diminishes the interaction between the components.

Cell-Based Assays

Cell-based assays can be used to evaluate compounds for their ability to interact with Sirt4 protein, e.g., bind or modulate the enzymatic activity of a Sirt4 protein. Useful assays include assays in which a Sirt4-associated parameter is evaluated. Other parameters that can be evaluated include parameters that assess insulin production or secretion.

In addition, it is possible to evaluate the modification state of a substrate in a Sirt4-expressing cell. For example, one can evaluate the ADP-ribosylation state of a substrate, such as glutamate dehydrogenase (GDH), aldehyde dehydrogenase (ADH), or histones, or a fragment of any of the above, or a Sirt4 binding partner. Optionally, the substrate can be immunoprecipitated from an extract made from the Sirt4 expressing cell (e.g., contacted or not contacted with a test compound). The precipitated substrate can then be evaluated. In another variation, the modified form of the substrate is detected using a reagent that discriminates between the modified and unmodified form. For example, the reagent is an antibody that specifically recognizes the ADP-ribosylated form.

Another exemplary cell based assay can include contacting a cell expressing a Sirt4 protein with a test compound and determining the ability of the test compound to modulate (e.g.

stimulate or inhibit) an activity of a Sirt4 protein, and/or determine the ability of the test compound to modulate expression of Sirt4, e.g., by detecting Sirt4 nucleic acids (e.g., mRNA or cDNA) or proteins in the cell. Determining the ability of the test compound to modulate Sirt4 activity can be accomplished, for example, by determining the ability of a Sirt4 protein or nucleic acid to bind to or interact with a substrate (e.g., as described above), to bind or interact with the test molecule, and by determining the ability of the test molecule to modulate a parameter, e.g., insulin secretion, insulin levels, or β-amyloid peptide accumulation.

Cell-based systems can be used to identify compounds that decrease expression and/or activity and/or effect of Sirt4. Such cells can be recombinant or non-recombinant, such as cell lines that express SIRT4 gene. In some embodiments, the cells can be recombinant or non-recombinant cells which express a Sirt4 binding partner. Exemplary systems include mammalian or yeast cells that express Sirt4, e.g., from a recombinant nucleic acid. In utilizing such systems, cells are exposed to compounds suspected of increasing expression and/or activity of Sirt4. After exposure, the cells are assayed, for example, for Sirt4 expression or activity.

Alternatively, the cells may also be assayed for the activation or inhibition of the ADP-ribosylation function of Sirt4, or modulation of insulin secretion or β-amyloid peptide accumulation. In one embodiment, the levels of ADP-ribosylation of a mitochondrial protein, e.g., glutamate dehydrogenase, are evaluated, e.g., in isolated mitochondria. In another embodiment, secreted insulin or β-amyloid peptide can be measured directly, e.g., with an immunoglobulin, e.g., by ELISA. The cells can also be assayed for ATP levels or ATP/ADP ratio. ATP and ADP in sample extracts can be measured using chromatographic methods, as described herein. ATP levels can also be measured by using cells transfected with a reporter gene, such as a luciferase expression construct designed to emit a luminescence signal that is directly correlated to ATP concentration (Kohler et al. (1998) *FEBS Lett* 441:97-102 and Kennedy et al. (1999) *J Biol Chem* 274:13281-91). ATP and ADP can also be measured, e.g., using enzymatic methods, e.g., using the ENLITEN® ATP Assay System (Promega, Madison, Wis.) or see Adra et al. (1987) *Gene* 60:65-74, U.S. Pat. No. 4,923,796.

A cell-based assay can be performed using a single cell, or a collection of at least two or more cells. The cell can be a yeast cell (e.g., *Saccharomyces cerevisiae*) or a mammalian cell, including but not limited to somatic or embryonic cells (e.g., pancreatic or brain cells), HepG2 cells, MIN6 cells, INS-1 cells, Chinese hamster ovary cells, HeLa cells, human 293 cells, and monkey COS-7 cells. The collection of cells can form a tissue. A "tissue" refers to a collection of similar cell types (such as epithelium, connective, muscle, and nerve tissue).

In another embodiment, modulators of Sirt4 gene expression are identified. For example, a cell or cell free mixture is contacted with a candidate compound and the expression of Sirt4 mRNA or protein evaluated relative to the level of expression of Sirt4 mRNA or protein in the absence of the candidate compound. When expression of the Sirt4 mRNA or protein is greater in the presence of the candidate compound than in its absence, the candidate compound is identified as a stimulator of Sirt4 mRNA or protein expression. Alternatively, when expression of Sirt4 mRNA or protein is less (statistically significantly less) in the presence of the candidate compound than in its absence, the candidate compound is identified as an inhibitor of the Sirt4 mRNA or protein expression. The level of Sirt4 mRNA or protein expression can be determined by methods for detecting Sirt4 mRNA or protein, e.g., using probes or antibodies, e.g., labeled probes or antibodies.

In addition to cell-based and in vitro assay systems, non-human organisms, e.g., transgenic non-human organisms or a model organism, can also be used. A transgenic organism is one in which a heterologous DNA sequence is chromosomally integrated into the germ cells of the animal. A transgenic organism will also have the transgene integrated into the chromosomes of its somatic cells. Organisms of any species, including, but not limited to: yeast, worms, flies, fish, reptiles, birds, mammals (e.g., mice, rats, rabbits, guinea pigs, pigs, micro-pigs, and goats), and non-human primates (e.g., baboons, monkeys, chimpanzees) may be used in the methods described herein.

A transgenic cell or animal used in the methods disclosed herein can include a transgene that encodes, e.g., Sirt4. The transgene can encode a protein that is normally exogenous to the transgenic cell or animal, including a human protein, e.g., human Sirt4. The transgene can be linked to a heterologous or a native promoter. A transgenic animal can also be produced with reduced expression or activity of, e.g., Sirt4, e.g., a Sirt4 deletion or mutant. Methods of making transgenic cells and animals are known in the art.

Accordingly, in another embodiment, this disclosure features a method of identifying a compound as a candidate of treatment of a metabolic disorder, e.g., a disorder characterized by an insufficiency or excess of insulin, e.g., type 1 diabetes, type 2 diabetes, or hyperinsulinemia. The method includes: providing a compound which interacts with, e.g., binds to, Sirt4; evaluating the effect of the compound on insulin secretion; and further evaluating the effect of the test compound on a subject, e.g., an animal model, e.g., an animal model for a metabolic disorder, e.g., type 1 diabetes or type 2 diabetes. Exemplary animal models are described below. The interaction between a test compound and Sirt4 can be evaluated by any of the methods described herein, e.g., using cell-based assays or cell-free in vitro assays.

Accordingly, in another embodiment, this disclosure features a method of identifying a compound as a candidate of treatment of a β-amyloid disorder, e.g., a disorder characterized by β-amyloid accumulation, e.g., Alzheimer's disease. The method includes: providing a compound which interacts with, e.g., binds to, Sirt4; evaluating the effect of the compound on β-amyloid accumulation; and further evaluating the effect of the test compound on a subject, e.g., an animal model, e.g., an animal model for a β-amyloid disorder, e.g., Alzheimer's disease. Exemplary animal models are described below. The interaction between a test compound and Sirt4 can be evaluated by any of the methods described herein, e.g., using cell-based assays or cell-free in vitro assays.

Test Compounds

A "compound" or "test compound" can be any chemical compound, for example, a macromolecule (e.g., a polypeptide, a protein complex, or a nucleic acid) or a small molecule (e.g., an amino acid, a nucleotide, an organic or inorganic compound). The test compound can have a formula weight of less than about 10 000 grams per mole, less than 5 000 grams per mole, less than 1 000 grams per mole, or less than about 500 grams per mole. The test compound can be naturally occurring (e.g., a herb or a nature product), synthetic, or both. Examples of macromolecules are proteins, protein complexes, and glycoproteins, nucleic acids, e.g., DNA, RNA (e.g., double stranded RNA or RNAi) and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, nucleosides, glycosidic compounds, organic or inorganic compounds e.g., heteroorganic or organometallic compounds. One exemplary type of protein compound is an antibody or a modified scaffold domain protein. A test compound can be the only substance assayed by the method described herein. Alternatively, a collection of test compounds can be assayed either consecutively or concurrently by the methods described herein.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum *C&EN*, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., framework).

Devices for the preparation of combinatorial libraries are commercially available (see, e.g., 357 MPS, 390 MPS, Advanced Chem Tech, Louisville Ky.; SYMPHONY™, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Asinex, Moscow, RU, Tripos, Inc., St. Louis, Mo.; ChemStar, Ltd, Moscow, RU; 3D Pharmaceuticals, Exton, Pa.; Martek Biosciences, Columbia, Md.; etc.).

Test compounds can also be obtained from: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the "one-bead one-compound" library method; and synthetic library methods using affinity chromatography selection. The biological libraries include libraries of nucleic acids and libraries of proteins. Some nucleic acid libraries encode a diverse set of proteins (e.g., natural and artificial proteins; others provide, for example, functional RNA and DNA molecules such as nucleic acid aptamers or ribozymes. A peptoid library can be made to include structures similar to a peptide library. (See also Lam (1997) *Anticancer Drug Des.* 12:145). A library of proteins may be produced by an expression library or a display library (e.g., a phage display library).

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310).

Antibodies

Immunoglobulins can be produced that bind to Sirt4 or a Sirt4 binding partner (e.g., a protein that interacts with Sirt4). For example, an immunoglobulin can bind to Sirt4 and prevent Sirt4 enzymatic activity or an interaction between Sirt4 and a Sirt4 binding partner (e.g., GDH, IDE, or ANT). In one embodiment, the immunoglobulin is human, humanized, deimmunized, or otherwise non-antigenic in the subject.

In one embodiment, an immunoglobulin can be produced that can distinguish between mature, processed Sirt4 and unprocessed Sirt4, e.g., an antibody that binds preferentially to one form relative to the other. For example, an antibody that binds preferentially to the mature processed form can be an antibody that binds to amino acid residues 29-32 of a Sirt4 whose N-terminus begins at a residue corresponding to residue 29 of SEQ ID NO:1. An antibody that binds preferentially to an unprocessed Sirt4 can be an antibody that binds to amino acid residues 1-28 of SEQ ID NO:1.

Antibodies that bind specifically to mono-ADP-ribose can be utilized to distinguish ADP-ribosylated substrates form non-ADP-ribosylated substrates (see, e.g., Meyer and Hilz (1986) *Eur J Biochem* 155:157-65).

An immunoglobulin can be, for example, an antibody or an antigen-binding fragment thereof. As used herein, the term "immunoglobulin" refers to a protein consisting of one or more polypeptides that include one or more immunoglobulin variable domain sequences. A typical immunoglobulin includes at least a heavy chain immunoglobulin variable domain and a light chain immunoglobulin variable domain. An immunoglobulin protein can be encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 kDa or 214 amino acids) are encoded by a variable region gene at the NH2-terminus (about 110 amino acids) and a kappa or lambda constant region gene at the COOH-terminus. Full-length immunoglobulin "heavy chains" (about 50 kDa or 446 amino acids), are similarly encoded by a variable region gene (about 116 amino acids) and one of the other aforementioned constant region genes, e.g., gamma (encoding about 330 amino acids). The term "antigen-binding fragment" of an antibody (or simply "antibody portion" or "fragment"), as used herein, refers to one or more fragments of a full-length antibody that retain the ability to specifically bind to the antigen. Examples of antigen-binding fragments include: (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques, and the fragments are screened for utility in the same manner as are intact antibodies.

In one embodiment, the antibody against Sirt4 or another protein is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey). Preferably, the non-human antibody is a rodent (mouse or rat antibody). Method of producing rodent antibodies are known in the art. Non-human antibodies can be modified, e.g., humanized or deimmunized. Human monoclonal antibodies can be generated using transgenic mice carrying the human immunoglobulin genes rather than the mouse system (see, e.g., WO 91/00906 and WO 92/03918). Other methods for generating immunoglobulin ligands include phage display (e.g., as described in U.S. Pat. No. 5,223,409 and WO 92/20791).

Sirt4 Modulating Nucleic Acids

Nucleic acid molecules (e.g., DNA or RNA molecules) can be used to modulate (e.g., increase or decrease) Sirt4 expression or activity.

A Sirt4 modulator can be a nucleic acid molecule designed to increase expression or activity of Sirt4, e.g., an exogenous copy of the Sirt4 gene under the control of a promoter, e.g., a targeted promoter.

A Sirt4 modulator can be a siRNA, anti-sense RNA, or a ribozyme, which can decrease the expression of Sirt4. In some aspects, a cell or subject can be treated with a compound that modulates the expression of a gene, e.g., a nucleic acid which modulates, e.g., decreases, expression of a polypeptide which inhibits Sirt4. Such approaches include oligonucleotide-based therapies such as RNA interference, antisense, ribozymes, and triple helices.

Gene expression can be modified by gene silencing using double-strand RNA (Sharp (1999) *Genes and Development* 13: 139-141). RNAi methods, including double-stranded RNA interference (dsRNAi) or small interfering RNA (siRNA), have been extensively documented in a number of organisms, including mammalian cells and the nematode *C. elegans* (Fire, A., et al, *Nature,* 391, 806-811, 1998).

dsRNA can be delivered to cells or to an organism to antagonize Sirt4 or another protein described herein. For example, a dsRNA that is complementary to a Sirt4 nucleic acid can silence protein expression of the Sirt4. The dsRNA can include a region that is complementary to a coding region of a Sirt4 nucleic acid, e.g., a 5' coding region, a region encoding a Sirt4 core domain, a 3' coding region, or a non-coding region, e.g., a 5' or 3' untranslated region. dsRNA can be produced, e.g., by transcribing a cassette (in vitro or in vivo) in both directions, for example, by including a T7 promoter on either side of the cassette. The insert in the cassette is selected so that it includes a sequence complementary to the Sirt4 nucleic acid. The sequence need not be full length, for example, an exon, or between 19-50 nucleotides or 50-200 nucleotides. The sequence can be from the 5' half of the transcript, e.g., within 1000, 600, 400, or 300 nucleotides of the ATG. See also, the HISCRIBE™ RNAi Transcription Kit (New England Biolabs, MA) and Fire, A. (1999) *Trends Genet.* 15, 358-363. dsRNA can be digested into smaller fragments. See, e.g., US Patent Application 2002-0086356 and 2003-0084471.

In one embodiment, an siRNA is used. siRNAs are small double stranded RNAs (dsRNAs) that optionally include overhangs. For example, the duplex region is about 18 to 25 nucleotides in length, e.g., about 19, 20, 21, 22, 23, or 24 nucleotides in length. Typically, the siRNA sequences are exactly complementary to the target mRNA. It may also be possible to agonize activity of a Sirt4 by using an siRNA to inhibit a negative regulator of the Sirt4.

Double-stranded inhibitory RNA can also be used to selectively reduce the expression of one allele of a gene and not the other, thereby achieving an approximate 50% reduction in the expression of a Sirt4 antagonist polypeptide. See Garrus et al. (2001) *Cell* 107(1):55-65.

"Ribozymes" are enzymatic RNA molecules which cleave at specific sites in RNA. Ribozymes that can specifically cleave nucleic acids that encode or that are required for the expression of Sirt4 may be designed according to well-known methods.

A nucleic acid for modulating Sirt4 expression, activity, or function can be inserted into a variety of DNA constructs and vectors for the purposes of gene therapy. Vectors include plasmids, cosmids, artificial chromosomes, viral elements, and RNA vectors (e.g., based on RNA virus genomes). The vector can be competent to replicate in a host cell or to integrate into a host DNA. Viral vectors include, e.g., replication defective retroviruses, adenoviruses and adeno-associated viruses.

Examples of vectors include replication defective retroviral vectors, adenoviral vectors and adeno-associated viral vectors. Adenoviral vectors suitable for use by the methods disclosed herein include (Ad.RSV.lacZ), which includes the Rous sarcoma virus promoter and the lacZ reporter gene as well as (Ad.CMV.lacZ), which includes the cytomegalovirus promoter and the lacZ reporter gene. Methods for the preparation and use of viral vectors are described in WO 96/13597, WO 96/33281, WO 97/15679, and Trapnell et al., *Curr. Opin. Biotechnol.* 5(6):617-625, 1994, the contents of which are incorporated herein by reference.

A gene therapy vector is a vector designed for administration to a subject, e.g., a mammal, such that a cell of the subject is able to express a therapeutic gene contained in the vector. The therapeutic gene may encode a protein (e.g., Sirt4). The therapeutic gene can also be used to provide a non-coding transcript, e.g., an antisense RNA, a ribozyme, or a dsRNA, that targets an RNA of a sirtuin gene, e.g., a Sirt4 gene).

The gene therapy vector can contain regulatory elements, e.g., a 5' regulatory element, an enhancer, a promoter, a 5' untranslated region, a signal sequence, a 3' untranslated region, a polyadenylation site, and a 3' regulatory region. For example, the 5' regulatory element, enhancer or promoter can regulate transcription of the DNA encoding the therapeutic polypeptide or other transcript. The regulation can be tissue specific. For example, the regulation can restrict transcription of the desired gene, e.g., Sirt4, to pancreas cells, e.g., pancreatic islet β-cells. For example, the regulation can restrict transcription of the desired gene, e.g., Sirt4, to nervous tissue cells, e.g., neuronal or microglial cells. Alternatively, regulatory elements can be included that respond to an exogenous drug, e.g., a steroid, tetracycline, or the like. Thus, the level and timing of expression of the therapeutic nucleic acid can be controlled.

Gene therapy vectors can be prepared for delivery as naked nucleic acid, as a component of a virus, or of an inactivated virus, or as the contents of a liposome or other delivery vehicle. See, e.g., US 2003-0143266 and 2002-0150626. In one embodiment, the nucleic acid is formulated in a lipid-protein-sugar matrix to form microparticles., e.g., having a diameter between 50 nm to 10 micrometers. The particles may be prepared using any known lipid (e.g., dipalmitoylphosphatidylcholine, DPPC), protein (e.g., albumin), or sugar (e.g., lactose).

The gene therapy vectors can be delivered using a viral system. Exemplary viral vectors include vectors from retroviruses, e.g., Moloney retrovirus, adenoviruses, adeno-associated viruses, and lentiviruses, e.g., Herpes simplex viruses (HSV). HSV, for example, is potentially useful for infecting nervous system cells. See, e.g., US 2003/0147854, 2002/0090716, 2003/0039636, 2002/0068362, and 2003/0104626. The gene delivery agent, e.g., a viral vector, can be produced from recombinant cells which produce the gene delivery system.

A gene therapy vector can be administered to a subject, for example, by intravenous injection, by local administration (see U.S. Pat. No. 5,328,470) or by stereotactic injection (see e.g., Chen et al. (1994) *Proc. Natl. Acad. Sci. USA* 91:3054-3057). The gene therapy agent can be further formulated, for example, to delay or prolong the release of the agent by means of a slow release matrix. One method of providing a therapeutic agent, is by inserting a gene therapy vector into cells harvested from a subject. The cells are infected, for example, with a retroviral gene therapy vector, and grown in culture. The subject is then replenished with the infected culture cells. The subject is monitored for recovery and for production of the therapeutic polypeptide or nucleic acid.

The disclosure also includes vectors, such as gene therapy vectors, that include a Sirt4 regulatory sequence (e.g., a Sirt4 promoter) for regulating a coding sequence other than Sirt4.

Cell-based therapeutic methods include introducing a nucleic acid that provides a therapeutic activity operably linked to a promoter into a cell in culture. The therapeutic nucleic acid can provide the desired modulation of Sirt4 activity in a cultured cell, e.g., an increase or decrease in Sirt4 activity to an insulin-secreting cell. Further, it is also possible to modify cells, e.g., stem cells, using nucleic acid recombination, e.g., to insert a transgene, e.g., a transgene that provides a therapeutic activity. The modified stem cell can be administered to a subject. Methods for cultivating stem cells in vitro are described, e.g., in US Application 2002/0081724. In some examples, the stem cells can be induced to differentiate in the subject and express the transgene. For example, the stem cells can be differentiated into pancreas, liver, adipose, neuronal or skeletal muscle cells. The stem cells can be derived from a lineage that produces cells of the desired tissue type, e.g., pancreas, liver, adipose, neuronal, or skeletal muscle cells.

Modifications to nucleic acid molecules may be introduced as a means of increasing intracellular stability and half-life. Exemplary modifications include the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Artificial Transcription Factors

Artificial transcription factors can also be used to regulate genes described herein, e.g., genes encoding Sirt4, GDH, IDE, or ANT.

The artificial transcription factor can be designed or selected from a library. The protein can include one or more zinc finger domains. For example, the protein can be prepared by selection in vitro (e.g., using phage display, U.S. Pat. No. 6,534,261) or in vivo, or by design based on a recognition code (see, e.g., WO 00/42219 and U.S. Pat. No. 6,511,808). See, e.g., Rebar et al. (1996) *Methods Enzymol* 267:129; Greisman and Pabo (1997) *Science* 275:657; Isalan et al. (2001) *Nat. Biotechnol* 19:656; and Wu et al. (1995) *Proc. Nat. Acad. Sci. USA* 92:344 for, among other things, methods for creating libraries of varied zinc finger domains.

Optionally, the artificial transcription factor can be fused to a transcriptional regulatory domain, e.g., an activation domain to activate transcription or a repression domain to repress transcription. The artificial transcription factor can itself be encoded by a heterologous nucleic acid that is delivered to a cell (e.g., a vector described herein) or the transcription factor itself can be delivered to a cell (see, e.g., U.S. Pat. No. 6,534,261). The heterologous nucleic acid that includes a sequence encoding the transcription factor can be operably linked to an inducible promoter, e.g., to enable fine control of the level of the transcription factor in the cell.

Gene Expression and Transcript Analysis

Different aspects disclosed herein can include evaluating expression of one or more genes described herein (e.g., genes encoding Sirt4, insulin, GDH, IDE, and ANT). Expression of a gene can be evaluated by detecting an mRNA, e.g., the transcript from the gene of interest or detecting a protein, e.g., the protein encoded by the gene of interest. Gene expression can also be measured, e.g., using an indirect method, e.g., using a reporter construct (e.g., as described below).

Reporter genes for measuring expression of Sirt4, or a Sirt4 target or binding partner, can be made by operably linking a regulatory sequence, e.g., a regulatory sequence of the Sirt4 gene, to a sequence encoding a reporter gene. A number of methods are available for designing reporter genes. For example, the sequence encoding the reporter protein can be linked in frame to all or part of the sequence that is normally regulated by the regulatory sequence. Such constructs can be referred to as translational fusions. It is also possible to link the sequence encoding the reporter protein to only regulatory sequences, e.g., the 5' untranslated region, TATA box, and/or sequences upstream of the mRNA start site. Such constructs can be referred to as transcriptional fusions. Still other reporter genes can be constructed by inserting one or more copies (e.g., a multimer of three, four, or six copies) of a regulatory sequence into a neutral or characterized promoter.

Reporter constructs can be used to evaluate expression of any gene, e.g., genes encoding Sirt4, insulin, GDH, ANT, or IDE, or other gene described herein.

Exemplary reporter proteins include chloramphenicol acetyltransferase, green fluorescent protein and other fluorescent proteins (e.g., artificial variants of GFP), beta-lactamase, beta-galactosidase, luciferase, and so forth. The reporter protein can be any protein other than the protein encoded by the endogenous gene that is subject to analysis. Epitope tags, e.g., flag or his tags, can also be used.

Exemplary methods for evaluating mRNAs include northern analysis, RT-PCR, microarray hybridization, SAGE, differential display, and monitoring reporter genes. Exemplary methods for evaluating proteins include immunoassays (e.g., ELISAs, immunoprecipitations, westerns), 2D-gel electrophoresis, and mass spectroscopy. It is possible to evaluate fewer than 100, e.g., less than 20, 10, 5, 4, or 3 different molecular species, e.g., to only evaluate the expression of the gene of interest, although it is typically useful to include at least one or two controls (e.g., a house keeping gene). It is also possible to evaluate multiple molecular species, e.g., in parallel, e.g., at least 10, 50, 20, 100, or more different species. See, e.g., the usage of microarrays, e.g. as described below.

One method for comparing transcripts uses nucleic acid microarrays that include a plurality of addresses, each address having a probe specific for a particular transcript, at least one of which is specific for a gene of interest, e.g., a gene encoding Sirt4, insulin, GDH, IDE, and ANT. Such arrays can include at least 100, or 1000, or 5000 different probes, so that a substantial fraction, e.g., at least 10, 25, 50, or 75% of the genes in an organism are evaluated. mRNA can be isolated from a cell or other sample of the organism. The mRNA can be reversed transcribed into labeled cDNA. The labeled cDNAs are hybridized to the nucleic acid microarrays. The arrays are detected to quantitate the amount of cDNA that hybridizes to each probe, thus providing information about the level of each transcript.

Methods for making and using nucleic acid microarrays are well known. For example, nucleic acid arrays can be fabricated by a variety of methods, e.g., photolithographic methods (see, e.g., U.S. Pat. Nos. 5,143,854; 5,510,270; and. 5,527,681), mechanical methods (e.g., directed-flow methods as described in U.S. Pat. No. 5,384,261), pin based methods (e.g., as described in U.S. Pat. No. 5,288,514), and bead based techniques (e.g., as described in PCT US/93/04145). The probe can be a single-stranded nucleic acid, a double-stranded nucleic acid (e.g., which is denatured prior to or during hybridization), or a nucleic acid having a single-stranded region and a double-stranded region. Preferably, the probe is single-stranded. The probe can be selected by a variety of criteria, and preferably is designed by a computer program with optimization parameters. The probe can be selected to hybridize to a sequence rich (e.g., non-homopolymeric) region of the nucleic acid. The $T_m$ of the probe can be optimized by prudent selection of the complementarity region and length. Ideally, the $T_m$ of all probes on the array is similar, e.g., within 20, 10, 5, 3, or 2° C. of one another. A database scan of available sequence information for a species can be used to determine potential cross-hybridization and specificity problems.

The isolated mRNA from samples for comparison can be reversed transcribed and optionally amplified, e.g., by rtPCR, e.g., as described in (U.S. Pat. No. 4,683,202). The nucleic acid can be labeled during amplification, e.g., by the incorporation of a labeled nucleotide. Examples of preferred labels include fluorescent labels, e.g., red-fluorescent dye Cy5 (Amersham) or green-fluorescent dye Cy3 (Amersham), and chemiluminescent labels, e.g., as described in U.S. Pat. No. 4,277,437. Alternatively, the nucleic acid can be labeled with biotin, and detected after hybridization with labeled streptavidin, e.g., streptavidin-phycoerythrin (Molecular Probes).

The labeled nucleic acid can be contacted to the array. In addition, a control nucleic acid or a reference nucleic acid can be contacted to the same array. The control nucleic acid or reference nucleic acid can be labeled with a label other than the sample nucleic acid, e.g., one with a different emission maximum. Labeled nucleic acids can be contacted to an array under hybridization conditions. The array can be washed, and then imaged to detect fluorescence at each address of the array.

A general scheme for producing and evaluating profiles can include the following. The extent of hybridization at an address is represented by a numerical value and stored, e.g., in a vector, a one-dimensional matrix, or one-dimensional array. The vector x has a value for each address of the array. For example, a numerical value for the extent of hybridization at a first address is stored in variable $x_a$. The numerical value can be adjusted, e.g., for local background levels, sample amount, and other variations. Nucleic acid is also prepared from a reference sample and hybridized to an array (e.g., the same or a different array), e.g., with multiple addresses. The vector y is construct identically to vector x. The sample expression profile and the reference profile can be compared, e.g., using a mathematical equation that is a function of the two vectors. The comparison can be evaluated as a scalar value, e.g., a score representing similarity of the two profiles. Either or both vectors can be transformed by a matrix in order to add weighting values to different nucleic acids detected by the array.

The expression data can be stored in a database, e.g., a relational database such as a SQL database (e.g., Oracle or Sybase database environments). The database can have multiple tables. For example, raw expression data can be stored in one table, wherein each column corresponds to a nucleic acid being assayed (e.g., one or more of genes encoding Sirt4, insulin, GDH, ANT, or IDE, or other gene described herein), and each row corresponds to a sample. A separate table can store identifiers and sample information, e.g., the batch number of the array used, date, and other quality control information.

Other methods for quantitating mRNAs include: quantitative RT-PCR. In addition, two nucleic acid populations can be compared at the molecular level, e.g., using subtractive hybridization or differential display to evaluate differences in mRNA expression, e.g., between a cell of interest and a reference cell.

Pharmaceutical Compositions

An agent that modulates activity of Sirt4 can be incorporated into a pharmaceutical composition, e.g., a composition that includes a pharmaceutically acceptable carrier.

As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the methods disclosed herein, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Examples of modulators of Sirt4 activity include nucleic acids that encode a Sirt4, or fragments thereof, nucleic acids that inhibit Sirt4 gene expression, and polypeptides that have a Sirt4 activity, fragments thereof, as well as antibodies that bind to and/or inhibit a Sirt4. Such modulators can be provided as a pharmaceutical composition. Other types of modulators include small molecule inhibitors and activators, e.g., as described herein.

A therapeutically effective amount of protein or polypeptide (i.e., an effective dosage) includes ranges, e.g., from about 0.001 to 30 mg/kg body weight, preferably about 0.01 to 25 mg/kg body weight. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, a composition that includes a modulator of Sirt4 activity is used to modulate (e.g., increase, decrease) the amount of insulin secreted by the pancreas.

In one embodiment, a composition that includes a modulator of Sirt4 activity is used to decrease the accumulation of β-amyloid peptide.

Diabetes

An agent that modulates Sirt4 expression or activity can be used to treat or prevent diabetes. The agent can be administered to a subject in an amount effective to treat, prevent, or ameliorate at least one symptom of diabetes. For example, an agent that decreases Sirt4 expression or activity can be used to increase insulin secretion, e.g., in a hypoinsulinemic subject. An agent that, e.g., increases Sirt4 expression can be used to decrease insulin secretion, e.g., in a hyperinsulinemic subject.

Examples of diabetes include insulin dependent diabetes mellitus and non-insulin dependent diabetes. For example the method includes administering to a patient having diabetes or at risk of diabetes a compound described herein.

For example, a compound described herein can be administered to a subject in a therapeutically effective amount to increase insulin secretion in response to glucose, decrease insulin secretion in response to glucose, decrease gluconeogenesis, improve glycemic control (i.e., lower fasting blood glucose), or normalize insulin sensitivity. The compound can be administered to a subject suffering from or at risk for diabetes or obesity.

In some instances, a patient can be identified as being at risk of developing diabetes (pre-diabetes) by having impaired glucose tolerance (IGT), insulin resistance, obesity, metabolic syndrome X, misfunction of glucose regulation by liver, fat, brain, and/or muscle, or fasting hyperglycemia.

Insulin dependent diabetes mellitus (Type 1 diabetes) is an autoimmune disease, where insulitis leads to the destruction of pancreatic β-cells. At the time of clinical onset of type 1 diabetes mellitus, significant number of insulin producing β cells are destroyed and only 15% to 40% are still capable of insulin production (McCulloch et al. (1991) *Diabetes* 40:673-679). β-cell failure results in a life long dependence on daily insulin injections and exposure to the acute and late complication of the disease.

Type 2 diabetes mellitus is a metabolic disease of impaired glucose homeostasis characterized by hyperglycemia, or high blood sugar, as a result of defective insulin action which manifests as insulin resistance, defective insulin secretion, or both. A patient with Type 2 diabetes mellitus has abnormal carbohydrate, lipid, and protein metabolism associated with insulin resistance and/or impaired insulin secretion. The disease leads to pancreatic beta cell destruction and eventually absolute insulin deficiency. Without insulin, high glucose levels remain in the blood. The long term effects of high blood glucose include blindness, renal failure, and poor blood circulation to these areas, which can lead to foot and ankle amputations. Early detection is critical in preventing patients from reaching this severity. The majority of patients with diabetes have the non-insulin dependent form of diabetes, currently referred to as Type 2 diabetes mellitus.

This disclosure also includes methods of treating disorders related to or resulting from diabetes, for example end organ damage, diabetic gastroparesis, diabetic neuropathy, cardiac dysrythmia, etc.

Exemplary molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., *Diabetes*, 50:1126-33 (2001); and a transgenic mouse with a dominant-negative IGF-1 receptor (KR-IGF-1R) having Type 2 diabetes-like insulin resistance.

Metabolic Syndrome

An agent that modulates Sirt4 expression or activity can be used to treat or prevent metabolic syndrome. The agent can be administered to a subject in an amount effective to treat, prevent, or ameliorate at least one symptom of metabolic syndrome.

Metabolic syndrome (e.g., Syndrome X) is a syndrome characterized by a group of metabolic risk factors in one person. These factors include two or more of (particularly three, four, five or more, or all of): central obesity (excessive fat tissue in and around the abdomen), atherogenic dyslipidemia (blood fat disorders—mainly high triglycerides and low HDL cholesterol—that foster plaque buildups in artery walls); insulin resistance or glucose intolerance (the body can't properly use insulin or blood sugar); prothrombotic state (e.g., high fibrinogen or plasminogen activator inhibitor-1 (PAI-1) in the blood); raised blood pressure (i.e., hypertension) (130/85 mmHg or higher); and proinflammatory state (e.g., elevated high-sensitivity C-reactive protein in the blood).

The underlying causes of this syndrome include overweight/obesity, physical inactivity and genetic factors. People with metabolic syndrome are at increased risk of coronary heart disease, other diseases related to plaque build-ups in artery walls (e.g., stroke and peripheral vascular disease), and type 2 diabetes. Metabolic syndrome is closely associated with a generalized metabolic disorder called insulin resistance, in which the body fails to utilize insulin efficiently.

Alzheimer's Disease

An agent that modulates Sirt4 expression or activity, preferably one that increases Sirt4 expression or activity, can be used to treat or prevent Alzheimer's Disease (AD). The agent can be an agent described herein or an agent identified by a method described herein. The agent can be administered in an amount effective to treat, prevent, or ameliorate at least one symptom of AD.

Alzheimer's Disease (AD) is a complex neurodegenerative disease that results in the irreversible loss of neurons and is an example of a neurodegenerative disease that has symptoms caused at least in part by protein aggregation.

Clinical hallmarks of Alzheimer's disease include progressive impairment in memory, judgment, orientation to physical surroundings, and language. Neuropathological hallmarks of AD include region-specific neuronal loss, amyloid plaques, and neurofibrillary tangles.

Amyloid plaques are extracellular plaques containing the β amyloid peptide (also known as Aβ, or Aβ42), which is a cleavage product of the β-amyloid precursor protein (also known as APP). Neurofibrillary tangles are insoluble intracellular aggregates composed of filaments of the abnormally hyperphosphorylated microtubule-associated protein, tau. Amyloid plaques and neurofibrillary tangles may contribute to secondary events that lead to neuronal loss by apoptosis (Clark and Karlawish, *Ann. Intern. Med.* 138(5):400-410 (2003)). For example, β-amyloid induces caspase-2-dependent apoptosis in cultured neurons (Troy et al. *J. Neurosci.* 20(4):1386-1392). The deposition of plaques in vivo may trigger apoptosis of proximal neurons in a similar manner.

Mutations in genes encoding APP, presenilin-1, and presenilin-2 have been implicated in early-onset AD (Lendon et al. *JAMA* 227:825 (1997)). Mutations in these proteins have been shown to enhance proteolytic processing of APP via an intracellular pathway that produces Aβ. Aberrant regulation of Aβ processing may be central to the formation of amyloid plaques and the consequent neuronal damage associated with plaques.

A variety of criteria, including genetic, biochemical, physiological, and cognitive criteria, can be used to evaluate AD in a subject. Symptoms and diagnosis of AD are known to medical practitioners. Some exemplary symptoms and markers of AD are presented below. Information about these indications and other indications known to be associated with AD can be used as an "AD-related parameter." An AD-related parameter can include qualitative or quantitative information. An example of quantitative information is a numerical value of one or more dimensions, e.g., a concentration of a protein or a tomographic map. Qualitative information can include an assessment, e.g., a physician's comments or a binary ("yes/no") and so forth. An AD-related parameter includes information that indicates that the subject is not diagnosed with AD or does not have a particular indication of AD, e.g., a cognitive test result that is not typical of AD or a genetic apolipoprotein E (APOE) polymorphism not associated with AD.

Progressive cognitive impairment is a hallmark of AD. This impairment can present as decline in memory, judgment, decision making, orientation to physical surroundings, and language (Nussbaum and Ellis, *New Eng. J. Med.* 348(14): 1356-1364 (2003)). Exclusion of other forms of dementia can assist in making a diagnosis of AD.

Neuronal death leads to progressive cerebral atrophy in AD patients. Imaging techniques (e.g., magnetic resonance imaging, or computed tomography) can be used to detect AD-associated lesions in the brain and/or brain atrophy.

The insulin degrading enzyme (IDE) can degrade β-amyloid protein in neuronal and microglial cell cultures (Qiu et al. (1997) *J. Biol. Chem.* 272:6641-6; Qiu et al. (1998) *J. Biol. Chem.* 273:32730-8; Vekrellis et al. (2000) *J. Neurosci.* 20:1657-65; Sudoh et al. (2002) *Biochemistry* 41:1091-9), and can eliminate the neurotoxicity of β-amyloid protein (Mukherjee et al. (2000) *J. Neurosci.* 20:8745-9). Furthermore, IDE −/−mice presented chronic elevation of β-amyloid protein, similar to that seen in AD patients (Farris et al. (2003) *Proc Nat'l Acad Sci USA* 100:4162-7).

AD patients may exhibit biochemical abnormalities that result from the pathology of the disease. For example, levels of tau protein in the cerebrospinal fluid is elevated in AD patients (Andreasen, N. et al. *Arch Neurol.* 58:349-350 (2001)). Levels of amyloid beta 42 (Aβ42) peptide can be reduced in CSF of AD patients (Galasko, D., et al. *Arch. Neurol.* 55:937-945 (1998)). Levels of Aβ42 can be increased in the plasma of AD patients (Ertekein-Taner, N., et al. *Science* 290:2303-2304 (2000)). Techniques to detect biochemical abnormalities in a sample from a subject include cellular, immunological, and other biological methods known in the art. For general guidance, see, e.g., techniques described in Sambrook & Russell, *Molecular Cloning: A Laboratory Manual,* 3rd Edition, Cold Spring Harbor Laboratory, N.Y. (2001), Ausubel et al., *Current Protocols in Molecular Biology* (Greene Publishing Associates and Wiley Interscience, N.Y. (1989), (Harlow, E. and Lane, D. (1988) *Antibodies: A Laboratory Manual*, Cold Spring Harbor Laboratory Press, Cold Spring Harbor, N.Y.), and updated editions thereof.

For example, antibodies, other immunoglobulins, and other specific binding ligands can be used to detect a biomolecule, e.g., a protein or other antigen associated with AD. For example, one or more specific antibodies can be used to probe a sample. Various formats are possible, e.g., ELISAs, fluorescence-based assays, western blots, and protein arrays. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). Nucleic Acids Res. 28, e3, I-VII; MacBeath, G., and Schreiber, S. L. (2000). *Science* 289, 1760-1763; and WO 99/51773A1. Proteins can also be analyzed using mass spectroscopy, chromatography, electrophoresis, enzyme interaction or using probes that detect post-translational modification (e.g., a phosphorylation, ubiquitination, glycosylation, methylation, or acetylation).

Metabolites that are associated with AD can be detected by a variety of means, including enzyme-coupled assays, using labeled precursors, and nuclear magnetic resonance (NMR). For example, NMR can be used to determine the relative concentrations of phosphate-based compounds in a sample, e.g., creatine levels. Other metabolic parameters such as redox state, ion concentration (e.g., $Ca^{2+}$) (e.g., using ion-sensitive dyes), and membrane potential can also be detected (e.g., using patch-clamp technology).

In one embodiment, a non-human animal model of AD (e.g., a mouse model) is used, e.g., to evaluate a compound or a therapeutic regimen, e.g., of an agent described herein. For example, U.S. Pat. No. 6,509,515 describes one such model animal which is naturally able to be used with learning and memory tests. The animal expresses an amyloid precursor protein (APP) sequence at a level in brain tissues such that the animal develops a progressive neurologic disorder within a short period of time from birth, generally within a year from birth, preferably within 2 to 6 months, from birth. The APP protein sequence is introduced into the animal, or an ancestor of the animal, at an embryonic stage, preferably the one cell, or fertilized oocyte, stage, and generally not later than about the 8-cell stage. The zygote or embryo is then developed to term in a pseudo-pregnant foster female. The amyloid precursor protein genes are introduced into an animal embryo so as to be chromosomally incorporated in a state which results in super-endogenous expression of the amyloid precursor protein and the development of a progressive neurologic disease in the cortico-limbic areas of the brain, areas of the brain which are prominently affected in progressive neurologic disease states such as AD. The gliosis and clinical manifestations in affected transgenic animals model neurologic disease. The progressive aspects of the neurologic disease are characterized by diminished exploratory and/or locomotor behavior and diminished 2-deoxyglucose uptake/utilization and hypertrophic gliosis in the cortico-limbic regions of the brain. Other animal models are also described in U.S. Pat. Nos. 5,387,742; 5,877,399; 6,358,752; and 6,187,992.

Additionally, glutamate is a key neurotransmitter. Sirt4 can function to regulate glutamate dehydrogenase, and thus glutamate levels in the brain. Sirt4 can play an important role in monitoring synapse and neuron function. Mice with an activating mutation in glutamate dehydrogenase suffer from neurological problems [ref].

Parkinson's Disease

Parkinson's disease includes neurodegeneration of dopaminergic neurons in the substantia nigra resulting in the degeneration of the nigrostriatal dopamine system that regulates motor function. This pathology, in turn, leads to motor dysfunctions. (see, e.g., and Lotharius et al., Nat. Rev. Neurosci., 3:932-42 (2002).) Exemplary motor symptoms include: akinesias, stooped posture, gait difficulty, postural instability, catalepsy, muscle rigidity, and tremor. Exemplary non-motor symptoms include: depression, lack of motivation, passivity, dementia and gastrointestinal dysfunction (see, e.g., Fahn, Ann. N.Y. Acad. Sci., 991:1-14 (2003) and Pfeiffer, Lancet Neurol., 2:107-16 (2003)) Parkinson's has been observed in 0.5 to 1 percent of persons 65 to 69 years of age and 1 to 3 percent among persons 80 years of age and older. (see, e.g., Nussbaum et al., N. Engl. J. Med., 348:1356-64 (2003)).

An agent that modulates Sirt4 activity can be used to ameliorate at least one symptom of a subject that has Parkinson's disease.

Molecular markers of Parkinson's disease include reduction in aromatic L-amino acid decarboxylase (AADC). (see, e.g., US Appl 20020172664); loss of dopamine content in the nigrostriatal neurons (see, e.g., Fahn, Ann. N.Y. Acad. Sci., 991:1-14 (2003) and Lotharius et al., Nat. Rev. Neurosci., 3:932-42 (2002)). In some familial cases, PD is linked to mutations in single genes encoding alpha-synuclein and parkin (an E3 ubiquitin ligase) proteins. (e.g., Riess et al., J. Neurol. 250 Suppl 1:13-10 (2003) and Nussbaum et al., N. Engl. J. Med., 348:1356-64 (2003)). A missense mutation in a neuron-specific C-terminal ubiquitin hydrolase gene is also associated with Parkinson's. (e.g., Nussbaum et al., N. Engl. J. Med., 348:1356-64 (2003))

A compound or library of compounds described herein can be evaluated in a non-human animal model of Parkinson's disease. Exemplary animal models of Parkinson's disease include primates rendered parkinsonian by treatment with the dopaminergic neurotoxin 1-methyl-4 phenyl 1,2,3,6-tetrahydropyridine (MPTP) (see, e.g., US Appl 20030055231 and Wichmann et al., Ann. N.Y. Acad. Sci., 991:199-213 (2003); 6-hydroxydopamine-lesioned rats (e.g., Lab. Anim. Sci., 49:363-71 (1999)); and transgenic invertebrate models (e.g., Lakso et al., J. Neurochem., 86:165-72 (2003) and Link, Mech. Ageing Dev., 122:1639-49 (2001)).

Evaluating Huntington's Disease

An agent that modulates the activity of Sirt4 can be used to ameliorate at least one symptom of Huntington's disease in a subject.

A variety of methods are available to evaluate and/or monitor Huntington's disease. A variety of clinical symptoms and indicia for the disease are known. Huntington's disease causes a movement disorder, psychiatric difficulties and cognitive changes. The degree, age of onset, and manifestation of these symptoms can vary. The movement disorder can include quick, random, dance-like movements called chorea.

One method for evaluating Huntington's disease uses the Unified Huntington's disease Rating Scale (UNDRS). It is also possible to use individual tests alone or in combination to evaluate if at least one symptom of Huntington's disease is ameliorated. The UNDRS is described in *Movement Disorders* (vol. 11:136-142, 1996) and Marder et al. *Neurology* (54:452-458, 2000). The UNDRS quantifies the severity of Huntington's Disease. It is divided into multiple subsections: motor, cognitive, behavioral, functional. In one embodiment, a single subsection is used to evaluate a subject. These scores can be calculated by summing the various questions of each section. Some sections (such as chorea and dystonia) can include grading each extremity, face, bucco-oral-ligual, and trunk separately.

Exemplary motor evaluations include: ocular pursuit, saccade initiation, saccade velocity, dysarthria, tongue protrusion, finger tap ability, pronate/supinate, a fist-hand-palm sequence, rigidity of arms, bradykinesia, maximal dystonia (trunk, upper and lower extremities), maximal chorea (e.g., trunk, face, upper and lower extremities), gait, tandem walking, and retropulsion. An exemplary treatment can cause a change in the Total Motor Score 4 (TMS-4), a subscale of the UHDRS, e.g., over a one-year period.

A number of animal model system for Huntington's disease are available. See, e.g., Brouillet, Functional Neurology 15(4): 239-251 (2000); Ona et al. Nature 399: 263-267 (1999), Bates et al. Hum Mol. Genet. 6(10):1633-7 (1997); Hansson et al. J. of Neurochemistry 78: 694-703; and Rubinsztein, D. C., Trends in Genetics, Vol. 18, No. 4, pp. 202-209 (a review on various animal and non-human models of HD).

Genetic Information

SIRT4 genetic information can be obtained, e.g., by evaluating genetic material (e.g., DNA or RNA) from a subject (e.g., as described below). Genetic information refers to any indication about nucleic acid sequence content at one or more nucleotides. Genetic information can include, for example, an indication about the presence or absence of a particular polymorphism, e.g., one or more nucleotide variations. Exemplary polymorphisms include a single nucleotide polymorphism (SNP), a restriction site or restriction fragment length, an insertion, an inversion, a deletion, a repeat (e.g., trinucleotide repeat, a retroviral repeat), and so forth.

Exemplary SIRT4 SNPs include: rs16950058; rs12425285; rs12424555; rs12307919; rs12300927; rs11834400; rs11614455; rs11613753; rs11609118; rs11412750; rs11378799; rs11065078; rs11065077; rs11065075; rs2905543; rs2701643; rs2522141; rs2522139; rs2522138; rs2522130; rs2522129; rs2464297; rs2464296; rs2428384; rs2261612; rs13461273; rs13461272; rs6400038; and rs6399397.

It is possible to digitally record or communicate genetic information in a variety of ways. Typical representations include one or more bits, or a text string. For example, a biallelic marker can be described using two bits. In one embodiment, the first bit indicates whether the first allele (e.g., the minor allele) is present, and the second bit indicates whether the other allele (e.g., the major allele) is present. For markers that are multi-allelic, e.g., where greater than two alleles are possible, additional bits can be used as well as other forms of encoding (e.g., binary, hexadecimal text, e.g., ASCII or Unicode, and so forth). In some embodiments, the genetic information describes a haplotype, e.g., a plurality of polymorphisms on the same chromosome. However, in many embodiments, the genetic information is unphased.

Methods of Evaluating Genetic Material

There are numerous methods for evaluating genetic material to provide genetic information. These methods can be used to evaluate a SIRT4 locus as well as other loci.

Nucleic acid samples can analyzed using biophysical techniques (e.g., hybridization, electrophoresis, and so forth), sequencing, enzyme-based techniques, and combinations-thereof. For example, hybridization of sample nucleic acids to nucleic acid microarrays can be used to evaluate sequences in an mRNA population and to evaluate genetic polymorphisms. Other hybridization based techniques include sequence specific primer binding (e.g., PCR or LCR); Southern analysis of DNA, e.g., genomic DNA; Northern analysis of RNA, e.g., mRNA; fluorescent probe based techniques (see, e.g., Beaudet et al. (2001) Genome Res. 11(4):600-8); and allele specific amplification. Enzymatic techniques include restriction enzyme digestion; sequencing; and single base extension (SBE). These and other techniques are well known to those skilled in the art.

Electrophoretic techniques include capillary electrophoresis and Single-Strand Conformation Polymorphism (SSCP) detection (see, e.g., Myers et al. (1985) *Nature* 313:495-8 and Ganguly (2002) *Hum Mutat.* 19(4):334-42). Other biophysical methods include denaturing high pressure liquid chromatography (DHPLC).

In one embodiment, allele specific amplification technology that depends on selective PCR amplification may be used to obtain genetic information. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition, it is possible to introduce a restriction site in the region of the mutation to create cleavage-based detection (Gasparini et al. (1992) *Mol. Cell Probes* 6:1). In another embodiment, amplification can be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

Enzymatic methods for detecting sequences include amplification based-methods such as the polymerase chain reaction (PCR; Saiki, et al. (1985) Science 230, 1350-1354) and ligase chain reaction (LCR; Wu. et al. (1989) *Genomics* 4, 560-569; Barringer et al. (1990), *Gene* 1989, 117-122; F. Barany. 1991, *Proc. Natl. Acad. Sci. USA* 1988, 189-193); transcription-based methods utilize RNA synthesis by RNA polymerases to amplify nucleic acid (U.S. Pat. Nos. 6,066,457; 6,132,997; 5,716,785; Sarkar et al., *Science* (1989) 244:331-34; Stofler et al., *Science* (1988) 239:491); NASBA (U.S. Pat. Nos. 5,130,238; 5,409,818; and 5,554,517); rolling circle amplification (RCA; U.S. Pat. Nos. 5,854,033 and 6,143,495) and strand displacement amplification (SDA; U.S. Pat. Nos. 5,455,166 and 5,624,825). Amplification methods can be used in combination with other techniques.

Other enzymatic techniques include sequencing using polymerases, e.g., DNA polymerases and variations thereof such as single base extension technology. See, e.g., U.S. Pat. Nos. 6,294,336; 6,013,431; and 5,952,174

Mass spectroscopy (e.g., MALDI-TOF mass spectroscopy) can be used to detect nucleic acid polymorphisms. In one embodiment, (e.g., the MassEXTEND™ assay, SEQUENOM, Inc.), selected nucleotide mixtures, missing at least one dNTP and including a single ddNTP is used to extend a primer that hybridizes near a polymorphism. The nucleotide mixture is selected so that the extension products between the different polymorphisms at the site create the greatest difference in molecular size. The extension reaction is placed on a plate for mass spectroscopy analysis.

Fluorescence based detection can also be used to detect nucleic acid polymorphisms. For example, different terminator ddNTPs can be labeled with different fluorescent dyes. A primer can be annealed near or immediately adjacent to a polymorphism, and the nucleotide at the polymorphic site can be detected by the type (e.g., "color") of the fluorescent dye that is incorporated.

Hybridization to microarrays can also be used to detect polymorphisms, including SNPs. For example, a set of different oligonucleotides, with the polymorphic nucleotide at varying positions with the oligonucleotides can be positioned on a nucleic acid array. The extent of hybridization as a function of position and hybridization to oligonucleotides specific for the other allele can be used to determine whether a particular polymorphism is present. See, e.g., U.S. Pat. No. 6,066,454.

In one implementation, hybridization probes can include one or more additional mismatches to destabilize duplex formation and sensitize the assay. The mismatch may be directly adjacent to the query position, or within 10, 7, 5, 4, 3, or 2 nucleotides of the query position. Hybridization probes can also be selected to have a particular $T_m$, e.g., between 45-60° C., 55-65° C., or 60-75° C. In a multiplex assay, $T_m$'s can be selected to be within 5, 3, or 2° C. of each other, e.g., probes for rs1800591 and rs2866164 can be selected with these criteria.

It is also possible to directly sequence the nucleic acid for a particular genetic locus, e.g., by amplification and sequencing, or amplification, cloning and sequence. High throughput automated (e.g., capillary or microchip based) sequencing apparati can be used. In still other embodiments, the sequence of a protein of interest is analyzed to infer its genetic sequence. Methods of analyzing a protein sequence include protein sequencing, mass spectroscopy, sequence/epitope specific immunoglobulins, and protease digestion.

Any combination of the above methods can also be used. The above methods can be used to evaluate any genetic locus, e.g., in a method for analyzing genetic information from particular groups of individuals or in a method for analyzing a polymorphism associated with a metabolic disorder, e.g., diabetes, or other disorder described herein, e.g., the SIRT4 locus.

Evaluating Markers of a Metabolic Disorder, e.g., Diabetes, or Other Disorder Described Herein A variety of criteria, including genetic, biochemical, physiological, and cognitive criteria, can be used to evaluate a metabolic disorder, e.g., diabetes, or other disorder described herein in a subject. Symptoms and diagnosis of a metabolic disorder, e.g., diabetes, or other disorder described herein are known to medical practitioners. Some exemplary symptoms and markers of a metabolic disorder, e.g., diabetes, or other disorder described herein are presented below. Information about these indications and other indications known to be associated with a metabolic disorder, e.g., diabetes, or other disorder described herein can be used as a parameter associated with the disorder.

A parameter can include qualitative or quantitative information. An example of quantitative information is a numerical value of one or more dimensions, e.g., a concentration of a protein or a tomographic map. Qualitative information can include an assessment, e.g., a physician's comments or a binary ("yes"/"no") and so forth. An parameter can include information that indicates that the subject is not diagnosed with a metabolic disorder, e.g., diabetes, or other disorder described herein or does not have a particular indication of a metabolic disorder, e.g., diabetes, or other disorder described herein.

Techniques to detect biochemical abnormalities in a sample from a subject include cellular, immunological, and other biological methods known in the art. For general guidance, see, e.g., techniques described in Sambrook & Russell, *Molecular Cloning: A Laboratory Manual*, 3$^{rd}$ Edition, Cold Spring Harbor Laboratory, N.Y. (2001), Ausubel et al., Current Protocols in Molecular Biology (Greene Publishing Associates and Wiley Interscience, N.Y. (1989), (Harlow, E. and Lane, D. (1988) *Antibodies: A Laboratory Manual*, Cold Spring Harbor Laboratory Press, Cold Spring Harbor, N.Y.), and updated editions thereof.

For example, antibodies, other immunoglobulins, and other specific binding ligands can be used to detect a biomolecule, e.g., a protein or other antigen associated with a metabolic disorder, e.g., diabetes, or other disorder described herein. For example, one or more specific antibodies can be used to probe a sample. Various formats are possible, e.g., ELISAs, fluorescence-based assays, Western blots, and protein arrays. Methods of producing polypeptide arrays are described in the art, e.g., in De Wildt et al. (2000). Nature Biotech. 18, 989-994; Lueking et al. (1999). Anal. Biochem. 270, 103-111; Ge, H. (2000). Nucleic Acids Res. 28, e3, I-VII; MacBeath, G., and Schreiber, S. L. (2000). Science 289, 1760-1763; and WO 99/51773A1.

Proteins can also be analyzed using mass spectroscopy, chromatography, electrophoresis, enzyme interaction or using probes that detect post-translational modification (e.g., a phosphorylation, ubiquitination, glycosylation, methylation, or acetylation).

Nucleic acid expression can be detected in cells from a subject, e.g., removed by surgery, extraction, post-mortem or other sampling (e.g., blood, CSF). Expression of one or more genes can be evaluated, e.g., by hybridization based techniques, e.g., Northern analysis, RT-PCR, SAGE, and nucleic acid arrays. Nucleic acid arrays are useful for profiling multiple mRNA species in a sample. A nucleic acid array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

Metabolites that are associated with a metabolic disorder, e.g., diabetes, or other disorder described herein can be detected by a variety of means, including enzyme-coupled assays, using labeled precursors, and nuclear magnetic resonance (NMR). For example, NMR can be used to determine the relative concentrations of phosphate-based compounds in a sample, e.g., creatine levels. Other metabolic parameters such as redox state, ion concentration (e.g., $Ca^{2+}$) (e.g., using ion-sensitive dyes), and membrane potential can also be detected (e.g., using patch-clamp technology).

Information about an a metabolic disorder, e.g., diabetes, or other disorder described herein-associated marker can be recorded and/or stored in a computer-readable format. Typically the information is linked to a reference about the subject and also is associated (directly or indirectly) with information about the identity of one or more nucleotides in the subject's SIRT4 genes.

Identifying Relevant Genotypes

Methods for identifying genotypes associated with a metabolic disorder, e.g., diabetes, or other disorder described herein can include comparisons to one or more reference sequences or an association study among individuals that have a particular characteristic, e.g., a particular parameter, e.g., associated with a disorder described herein, or a diagnosis of a metabolic disorder, e.g., diabetes, or other disorder described herein diagnosis.

Multiple sets of reference sequences may be used for comparison. Exemplary reference sequences include sequences from subjects at risk for or diagnosed with a metabolic disorder, e.g., diabetes, or other disorder described herein and sequences from subjects that are not at risk for or diagnosed with a metabolic disorder, e.g., diabetes, or other disorder described herein.

By evaluating one or more genetic loci, it is possible to determine an association for each locus or for each allele of each locus, and a phenotype. One type of test of association is the G-Test, but other statistical measures can also be used. A high degree of association, e.g., a high ch-square statistic, can indicate that a particular locus is associated with a state (e.g., a phenotype). This type of associational study can be used to map a genetic locus that is associated with the state. Associated loci can be used, e.g., for diagnostic evaluations (e.g., genetic counseling, risk evaluation, prophylactic care, care management, and so forth) and for research (e.g., identifying targets for therapeutics).

As seen herein, it is also possible to identify genes associated with disorders by using a method that includes: a) identifying a plurality of human individuals characterized by a disorder or having a genetic relationship with an subject characterized by the disorder; and b) comparing distribution of a plurality of genetic markers among the subjects of the first plurality to distribution of markers of the plurality of genetic markers among subjects of a second plurality of human subjects, wherein the human subjects of the second plurality have attained at least 90, 95, 98, or 100 years of age. For example, the plurality of genetic markers includes at least one, 10, 20, 30 or 50 markers from each chromosome. The method can further include evaluating a measure of linkage disequilibrium (e.g., a LOD score). For example, each subject of the first plurality is suffering or at risk for an age-associated disorder or each subject of the first plurality is genetically related to an subject suffering or at risk for an age-associated disorder.

In one embodiment, the first plurality includes at least 50, 100, 150, 200, or 300 subjects. In one embodiment, the human subjects of the second plurality are free of an a metabolic disorder, e.g., diabetes, or other disorder described herein diagnosis. For example, the human subjects of the second plurality are cognitively intact at the age of 85, 90, 95, 98, or 100 and/or the human subjects of the second plurality are free of a symptom or diagnosis of the disorder. In one embodiment, the second plurality includes at least 50, 100, 150, 200, 300, 500 or 800 subjects.

Pharmacogenomics

Both prophylactic and therapeutic methods of treatment may be specifically tailored or modified, based on knowledge obtained from a pharmacogenomics analysis. In particular, a subject can be treated based on the presence or absence of a genetic polymorphism associated with a metabolic disorder, e.g., diabetes, or other disorder described herein, e.g., a polymorphism associated with the SIRT4 locus.

Pharmacogenomics allows a clinician or physician to target prophylactic or therapeutic treatments to patients who will most benefit from the treatment and to avoid the treatment of patients who will experience toxic or other undesirable drug-related side effects. In particular, a diet or drug that affects a metabolic disorder, e.g., diabetes, or other disorder described herein can be prescribed as a function of the subject's SIRT4 locus. For example, if the individual's SIRT4 locus includes an allele that is predisposed to a metabolic disorder, e.g., diabetes, or other disorder described herein relative to other alleles, the individual can be indicated for a prophylactic treatment for a drug that alleviates a metabolic disorder, e.g., diabetes, or other disorder described herein. In another example, the individual is placed in a monitoring program, e.g., to closely monitor for physical manifestations of a metabolic disorder, e.g., diabetes, or other disorder described herein onset.

These and other aspects of the invention are described further in the following examples, which are illustrative and in no way limiting.

EXAMPLES

Experimental Procedures

Plasmids

EST clones containing human and mouse Sirt4 cDNA were obtained from the American Type Culture Collection (Manassas, Va.). Human Sirt4 cDNA was amplified by PCR with the oligonucleotides MHSirt4-3 (5'-CACCGCGGTG GCGGCCGCATGAAGATGAGCTTTGCGTTGACTT TC-3') (SEQ ID NO:4) and MHSirt4-4 (5'.-CTTGTAATC CTCGAGGCATGGGTCTATCAAAGGCAGC-3') (SEQ ID NO:5). The human Sirt4 cDNA fragment was digested at sites within these oligonucleotide primers with NotI and XhoI, and the resulting fragment was inserted into the vector pCMV-FLAG-4A™ (Invitrogen; Carlsbad, Calif.) that had been digested with the same enzymes. The resulting plasmid, phSirt4FLAG, directs the overexpression of human Sirt4 with a C-terminal FLAG in mammalian cells. phSirt4 directs the overexpression of human Sirt4 in mammalian cells and was created by amplification of the Sirt4 gene using the primers MHSirt4-3 and MHSirt4-QC2 (5'-☐CTTGTAATC CTCGAGTCAGCATGGGTCTATCAAAGGCAGC-3') (SEQ ID NO:6). RNAi retroviral plasmids were constructed using pSUPER.retro™ as the backbone plasmid (OligoEngine, Seattle, Wash.). Mouse Sirt4 RNAi-a and -b were constructed by targeting the sequences 5'-CGCTTCCAAGC-CCTGAACC-3' (SEQ ID NO:7) and 5'-GGAGAGTTGCT-GCCTTTAA-3' (SEQ ID NO:8), respectively.

Cell Culture

HEK293T and HEPG2 cells were grown in DMEM medium supplemented with fetal bovine serum (FBS; 10% v/v), L-glutamine (2 mM), penicillin (100 units/ml), and streptomycin (100 µg/ml). MIN6 cells were grown in DMEM medium 1640, supplemented with FBS (15% v/v), L-glutamine (2 mM), sodium bicarbonate (1 mM), β-mercaptoethanol (2.5 µl/500 ml), penicillin (100 units/ml), and streptomycin (100 µg/ml). Cells were cultured at 37° C. in a humidified incubator containing 5% $CO_2$. All studies were performed using asynchronous log-phase cultures, and MIN6 cells were used between passages 29 and 40.

Viral Production and Infections

The pBp-amphotrophic viruses were produced by cotransfection of 293T (Phoenix) cells with the pBABE™ and pSUPER™ constructs as described (Picard et al. (2004) Nature 429:771-6). Transfections were carried out using jetPEI™ (Qbiogene, Carlsbad, Calif.). Virus was harvested 48 hours post-transfection and added to MIN6 cells in the presence of polybrene (10 µg/ml). Eight hours after viral infection, fresh media was added. MIN6 cells were selected with puromycin (1 μg/mL) 48 h following infection.

Immunoprecipitation

Cells were harvested 48 h post-transfection by scraping into PBS and centrifugation, and then incubated for 30 min in 3 ml of ice-cold NP40 lysis buffer (50 mM Tris pH 8.0, 150 mM NaCl, 1% NP40) containing protease inhibitors (EDTA-free COMPLETE™; Roche Molecular Biochemicals, Indianapolis, Ind.), and dithiothreitol (1 mM DTT; Sigma, St. Louis, Mo.). The lysate was clarified by centrifugation for 15 min at 4° C. at 14,000 rpm in a tabletop centrifuge, and the resulting supernatant was incubated at 4° C. for 2 h with Protein A resin (Sigma) that had been conjugated with anti-FLAG M2 (Sigma) or the appropriate antibody. Samples were washed four times with 10 ml of NP40 lysis buffer and the hSirt4-FLAG protein was eluted by the addition of FLAG peptide (400 μg/ml, in 50 mM Tris pH 8.0, 150 mM NaCl, 10 mM DTT). Alternatively, protein complexes were eluted from the Protein A resin by adding protein sample buffer (50 mM Tris-HCl (pH 6.8) containing 2% β-mercaptoethanol, 2% SDS, 10% glycerol, 0.01% bromophenol blue), and then analyzed by SDS-PAGE and Western blotting.

Deacetylase Assay

Deacetylase activity of immunoprecipitated and dialyzed hSirt4-FLAG (50 ng) was assessed by the FLUOR DE LYS$^3$ kit according to the manufacturer's directions (BIOMOL Research Laboratories Inc., Pa.). hSirt1-FLAG was used as a positive control. Experiments were performed in the presence and absence of 1 mM $NAD^+$.

ADP-Ribosylation Assays

ADP-ribosylation activity was assessed as described in Tanny et al. (1999) *Cell* 99:735-45. Briefly, hSirt4-FLAG (50 ng), hSirt5-FLAG (50 ng), or a buffer control were incubated with 3 μg histones and 3 μCi of $^{32}P-NAD^+$ in 50 mM Tris-HCl, pH 8.0, 150 mM NaCl, 10 mM DTT. The reaction mixture was incubated for 1 hr at 37° C., and the reaction stopped by the addition of 90 μA ice-cold 22% trichloroacetic acid (TCA), incubated on ice for 15 min, and centrifuged at 13,000 g for 15 minutes. The pellets were resuspended and loaded onto 8.5% or 15% SDS polyacrylamide gels. After electrophoresis, gels were stained with Coomassie brilliant blue and $^{32}P$ in the gel detected by autoradiography.

Western Blots

Cells were lysed in protein sample buffer, vortexed, boiled for 5 minutes, and centrifuged at 17,000×g for 5 min. Extracts corresponding to equivalent cell numbers (or 5-15 Tg protein) were subjected to SDS-PAGE (4-15% gradient) according to the method of Laemmli ((1970) *Nature* 227:680-685), and transferred onto nitrocellulose membranes and incubated for 60 min with blocking solution (3% lowfat milk, 0.1% TWEEN®-20 in PBS). Membranes were incubated for 1 hour with appropriate primary antibodies. The anti-mono-ADP-ribose antibody was as described (Meyer et al. (1986) *Eur J Biochem* 155:157-65). After 3-10 minutes washes in blocking buffer, membranes were incubated with the appropriate horseradish peroxidase-conjugated antibody (1:10,000). The chemiluminescent signal was generated by incubation with the ECL reagent (Amersham Biosciences, Piscataway, N.J.).

Fluorescence Microscopy

HepG2 cells were grown on coverslips and transfected with phSirt4FLAG and pDSRed™2-Mito (BD Biosciences, Palo Alto, Calif.) 48 hours before the experiment. On the day of the experiment, cells were washed twice with ice-cold PBS and then incubated in paraformaldehyde (4% w/v) at room temperature for 10 minutes. The fixed cells were washed three times with PBS and then incubated in TRITON® X-100 (0.5% v/v) for 10 min and then washed with PBS. The coverslips were mounted with VECTASHIELD® mounting media containing 4',6-diamidino-2-phenylndole, dilactate (DAPI; Vector, Burlingame, Calif.). Fluorescence was visualized by using a confocal microscope (Zeiss LSM510; Zeiss, Thornwood, N.Y.).

Immunohistochemistry of Mouse Tissues

Immunohistochemistry of endogenous Sirt4 in mouse tissue was performed using a microwave citrate unmasking protocol. Briefly, mouse organ sections were deparaffinized in xylene and rehydrated through an ethanol series. Slides were then placed in citrate buffer (10 mM citric acid and 25 mM NaOH) and microwaved on high power for 25 minutes. Slides were then cooled in running tap water and soaked in PBS+0.1% Tween®-20 for 10 minutes at room temperature. Slides were incubated in 10% donkey serum for 1 hour at room temperature to block non-specific antibody binding. After 1 hour, primary antibody (1:100) was added, and slides were incubated overnight at 4° C. in a humidified chamber. A primary antibody against mouse Sirt4 was produced in a rabbit against the peptide LEMNFPLSSAAQDP (SEQ ID NO:9), which is in the C-terminal region of the protein. Slides were then washed three times in PBS+0.1% TWEEN®-20 at room temperature for 10 minutes each. Secondary antibody (1:200) was added, and the slides were incubated for 1 hour at 37° C. Slides were then washed three times in PBS+0.1% TWEEN®-20 at room temperature, counterstained with DAPI, and coverslipped. Mouse monoclonal antibody for detection of insulin was obtained from Zymed Laboratories (San Francisco, Calif.). Secondary antibodies were obtained from Molecular Probes (Eugene, Oreg.): ALEXA FLUOR® 488 donkey α-mouse IgG and ALEXA FLUOR®594 donkey α-rabbit IgG. Images were acquired using a SPOT™ digital camera (Diagnostic Instruments, Inc, Sterling Heights, Mich.) mounted on a ECLIPSE E600™ fluorescence microscope (Nikon).

Purification of Mitochondria

Mitochondria and other subcellular fractions were purified by differential centrifugation as described (Schwer et al. (2002) *J Cell Biol* 158:647-57). Briefly, cells were collected in SEM, (150 mM NaCl, 10 mM KCl, 10 mM Tris/HCl, pH 6.7), and then disrupted by a Dounce homogenizer. Samples were centrifuged twice at 1,000×g for 5 min to pellet the nuclei and intact cells. To separate the mitochondrial fraction from the cytosolic fraction, we centrifuged the supernatant at 5,000×g for 10 min. We washed the resulting pellet with sucrose/$Mg^{2+}$ medium (10 mM Tris/HCl, pH 6.7, 250 mM sucrose, 150 mM $MgCl_2$,), recentrifuged, and resuspended the final pellet in mitochondrial suspension medium (10 mM Tris/HCl, pH 7.0, 250 mM sucrose). 10 μg of protein from each fraction was separated by SDS-PAGE and then analyzed by western blot.

Insulin Secretion Assays

MIN6 cells were plated in the wells of a 12-well plate at least 24-hours before secretion assays. Cells were washed once with Krebs-Ringer-HEPES buffer (KRB) containing 128 mMNaCl, 5 mM KCl, 2.7 mM $CaCl_2$, 1.2 mM $MgSO_4$, 1 mM $Na_2HPO_4$, 20 mM HEPES (pH 7.4). After incubation for 1-3 hours in KRB containing 3 mM glucose, the cells were incubated in KRB containing either 3 or 16.7 mM glucose at 37° C. for one hour. Insulin concentration was measured by ELISA (Alpco Diagnostics; Windham, N.H.).

Glutamate Dehydrogenase Assay

Glutamate dehydrogenase (50 μg; Ultrapure from Sigma) was incubated with or without Sirt4 (10 ng) in 200 μg of ADP-ribosylation buffer (50 mM Tris pH 8.0, 10 mM DTT, 150 mM NaCl) in the presence or absence of 1 mM NAD or 1 mM nicotinamide at 37° C. for the indicated times. Then, an aliquot of the reaction was assayed for glutamate dehydrogenase activity. Activity assays were performed at 25° C. using a BioSpec-1601 spectrophotometer (Shimadzu Scientific Instruments, Inc; Braintree, Mass.) at $A_{340}$ based on the oxidation of NADH as described previously. Data was collected for 5-10 min. at 10 sec. intervals. At the end of each experiment, less than 10% of substrates had been depleted.

Example 1

Purification and Enzymatic Activity of Sirt4

This example demonstrates that Sirt4 possesses an ADP-ribosyltransferase activity.

Figure 1A:
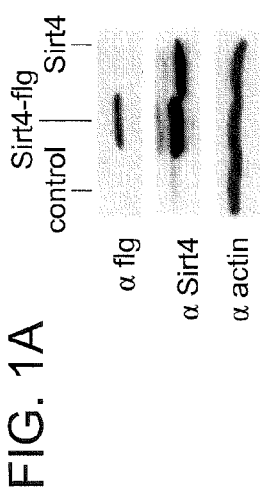
FIG. 1A. 293T cells were transiently transfected with pCMV-FLAG-4A® (control), phSirt4FLAG or hSirt4. Protein expression was verified by anti-FLAG, or anti-hSirt4 antibodies.
Figure 1B:
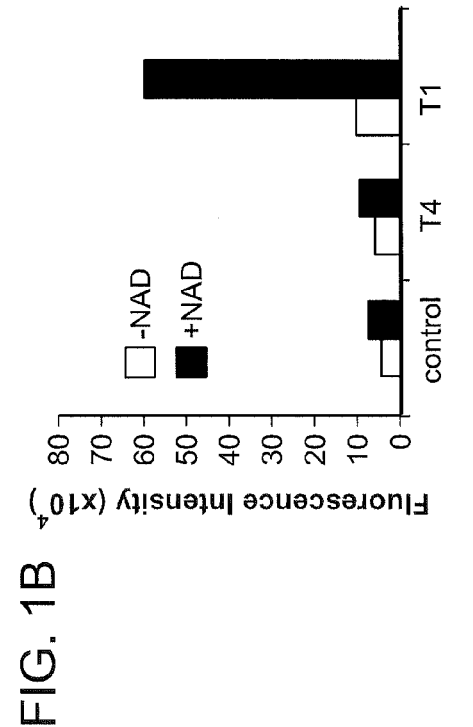
FIG. 1B. hSirt4-FLAG or hSirt1-FLAG was immunoprecipitated from 293T cells and dialyzed to remove FLAG peptide. 50 ng of each protein was assayed for deacetylase activity after a 1 hour at 37° C. incubation with the FLUOR DE LYS™ substrate (BIOMOL) in the absence (open bars) or presence (black bars) of 1 mM NAD⁺.

To investigate the enzymatic activity of hSirt4, two constructs were designed (phSirt4FLAG, phSirt4) to overproduce human Sirt4 with or without a C-terminal FLAG tag in mammalian cells. When 293T cells were transfected with phSirt4FLAG, a 34 kDa band was produced that was recognized by both anti-FLAG and anti-hSirt4 antibodies (FIG. 1A). The FLAG-tagged protein migrated more slowly than did the native version of Sirt4.

Figure 1C:
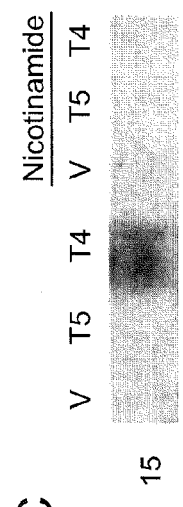
FIG. 1C. ADP-ribosyltransferase activity of hSirt4-FLAG, hSirt5-FLAG or buffer control was assessed. 50 ng of protein was incubated with [$^{32}$P]-NAD⁺ in the presence of core histone proteins as the substrate. Experiments were also performed in the presence of 1 mM nicotinamide.

The enzymatic activity of Sirt4-FLAG protein immunoprecipitated from mammalian cells in a nondenaturing buffer was evaluated. Sirt4 was able to transfer a radioactive ADP-ribosyl group from NAD to histones (FIG. 1C). This ADP-ribosylation activity was inhibited by 1 mM nicotinamide (FIG. 1C). Mass spectroscopy confirmed that Sirt4 transferred an approximately 500 Dalton moiety to Histone 2A. The molecular weight of this moiety corresponds to the molecular weight of ADP-ribose (FIG. 1D).

Example 2

Subcellular Localization of Sirt4

This example demonstrates that Sirt4 is localized to mitochondria.

Figure 2A:
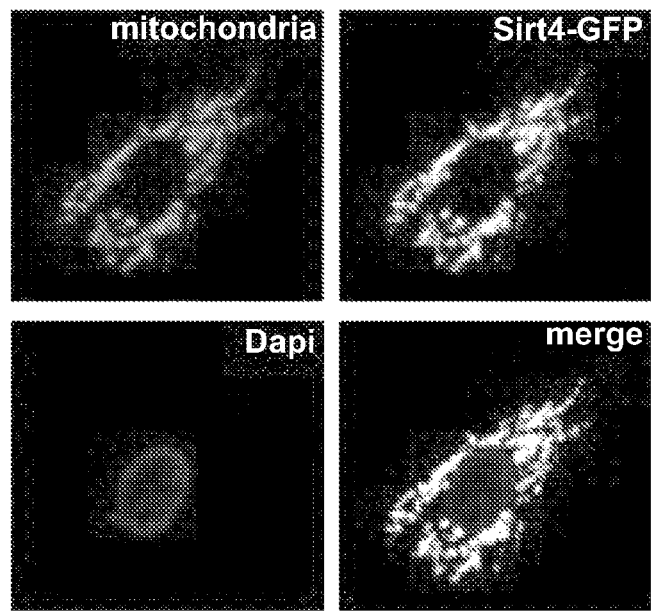
FIG. 2A. HepG2 cells were co-transfected with phSirt4-GFP (green), pDS-RED-MITO (red) or pGFP alone (FIG. 2B. green), and the fluorescence was visualized after 48 h using a confocal microscope.
Figure 2B:
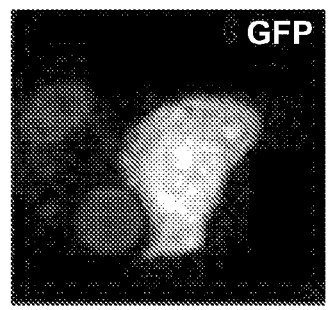
FIG. 2. Sirt4 localizes to mitochondria in human and mouse cells.
FIG. 2C. MIN6 cells were disrupted by homogenization and the mitochondrial fraction was isolated by sucrose centrifugation. Mitochondrial enrichment in the final sample was assessed by anti-HSP60 antibody. Endogenous Sirt4 was detected by anti-mSirt4 antibody.
FIG. 2D. N-terminal sequences for hSirt3 (SEQ ID NO: 10) and hSirt4 (SEQ ID NO: 11) are shown, and their potential cleavage sites are indicated by arrows.

Mammalian homologs of Sir2 have been localized to the nucleus (Luo et al. (2001) *Cell* 107:137-48; Vaziri et al. (2001) *Cell* 107:149-59), cytosol (North et al. (2003) *Mol Cell* 11:437-44), and mitochondria (Onyango et al. (2002) *Proc Natl Acad Sci USA* 99:13653-8; Schwer et al. (2002) *J Cell Biol* 158:647-57). To determine the localization of Sirt4, a plasmid was constructed (phSirt4GFP) that fused the C-terminus of human Sirt4 with GFP (Sirt4-GFP). When HepG2 cells were transiently transfected with phSirt4GFP, a punctate staining pattern was observed (FIG. 2A). Cotransfection experiments were performed with plasmids that target DSRed2 to the mitochondria (pDSRed™2-Mito) or peroxisome (pDSRed™2-Peroxi). Sirt4-GFP colocalized with DSRed™2 that was targeted to the mitochondria (FIG. 2A), but did not colocalize with the peroxisomal DSRed™ marker. Transfections with GFP alone (i.e., GFP that is not fused to Sirt4) did not result in a distinct localization pattern (FIG. 2B).

Figure 2C:
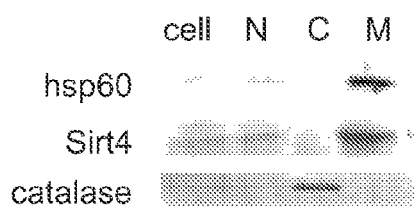

The mitochondrial localization of Sirt4 was verified by subcellular fractionation. Sirt4-FLAG was detected in the cell extract, whole cell/nucleus, and mitochondrial fractions, but not in the cytosolic/light fraction (FIG. 2C). HSP60, a mitochondrial marker, also co-fractionated with Sirt4-FLAG, while catalase could be detected strongly in the cytosolic/light fraction, but not in the mitochondrial fraction (FIG. 2C). In separate experiments, endogenous Sirt4 was detected in the mitochondrial fraction of both 293T and mouse MIN6 cells. These results strongly suggest that Sirt4 is localized to the mitochondria of human and mouse cells.

The N-terminus of Sirt4-FLAG was analyzed by Edman degradation to determine whether Sirt4 is post-translationally cleaved during mitochondrial import. As depicted in FIG. 2D, the first 28 amino acid residues were absent from the N-terminus, indicating that the protein had been post-translationally processed. In addition, a Sirt4-FLAG construct lacking the first 28 amino acids was not stable in cells. Thus, Sirt4 is post-translationally processed, likely by cleavage after serine 28, upon targeting to the mitochondria.

Example 3

Expression of Sirt4 in Mouse Tissues

This example demonstrates the distribution of Sirt4 in mouse tissues.

Figure 3A:
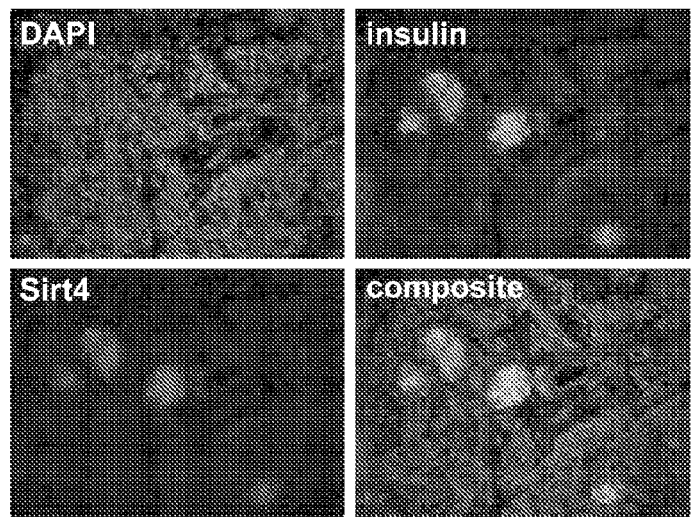
FIG. 3. Sirt4 is abundant in pancreatic islets. Sections of mouse pancreas were assessed for Sirt4 expression by anti-mSirt4 antibodies (red), and β-cells were identified by using antibodies against insulin (green). Samples were visualized at 10× (FIG. 3A) or 40× (FIG. 3B) magnification.
Figure 3B:
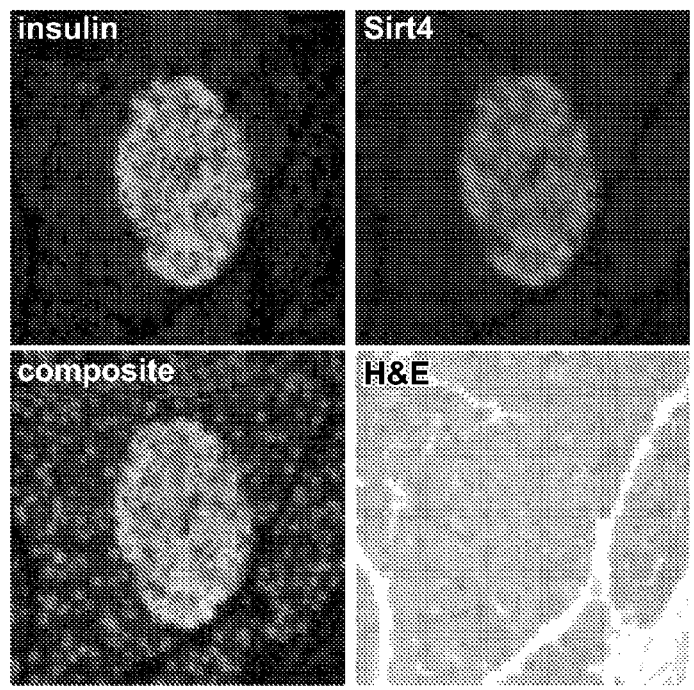

To understand the biological function of Sirt4, its endogenous expression profile in mouse tissues was determined by immunohistochemistry using antibodies generated against the C-terminus of mouse Sirt4. High levels of staining were observed in neurons and pancreatic islets. Moderate staining was observed in muscle, heart, liver, and kidney, and testes. Sirt4 was expressed strongly in islets of the pancreas, but not in surrounding goblet or acinar cells (FIGS. 3A and B). The expression of Sirt4 overlapped with the expression of insulin within islets (FIG. 3), indicating that Sirt4 may be involved in normal β-cell function.

Example 4

Sirt4 Regulates the Production and Secretion of Insulin

Figure 4A:
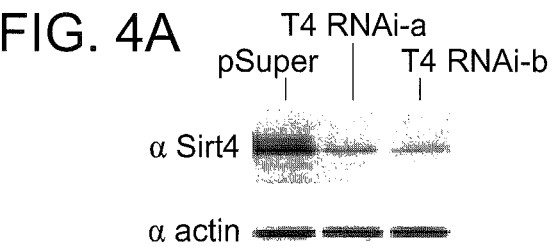
FIG. 4A. The levels of Sirt4 were reduced in MIN6 cells infected with virus that contained Sirt4 RNAi sequences compared to cells infected with pSUPER.
Figure 4B:
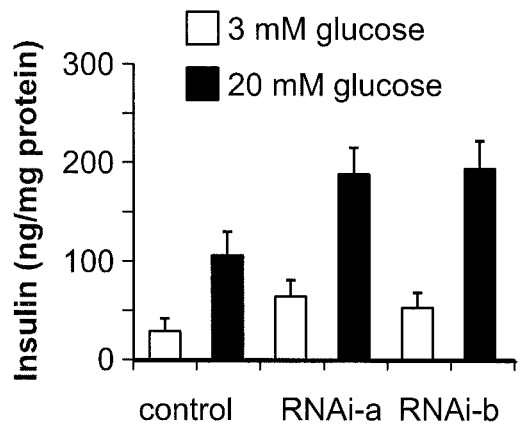
FIG. 4B. Insulin secretion was measured from control or RNAi MIN6 cells. Cells were pre-incubated with KRB buffer containing 3 mM glucose, then cells were shifted to buffer containing either 3 mM (open bars) or 16.7 mM glucose (filled bars). Insulin in the buffer was measured by ELISA after a 45 min incubation at 37° C.
Figure 4C:
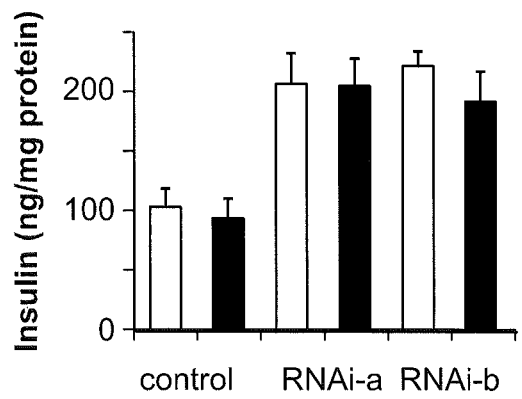
FIG. 4C. Insulin remaining inside cells was measured at the end of the insulin secretion assays by ELISA.

To test the role of Sirt4 in β-cell biology, insulin secretion in the mouse insulinoma, MIN6, β-cell line was studied. Using two separate RNAi constructs, stable MIN6 cells that had decreased levels of Sirt4 when compared to control cells that were infected with the empty vector as a control were engineered (FIG. 4A). To study insulin secretion, these cells were incubated in KRB containing 3 mM glucose, and then shifted to KRB containing either 3 (low) or 16.7 mM (high) glucose. Sirt4 RNAi treated cells secreted 2-fold more insulin when compared to control cells at both low and high glucose concentrations (FIG. 4B). The Sirt4 RNAi treated cells maintained a normal ability to respond to glucose, as the Sirt4 RNAi-expressing cells still responded to 16.7 mM glucose by secreting proportional insulin. Thus, the magnitude of insulin secretion differed between normal and Sirt4 RNAi cells, and this difference was maintained at difference glucose levels. The intracellular insulin level was determined at low and high glucose concentrations, and the Sirt4 RNAi treated cells were found to contain 2-fold higher levels of insulin (FIG. 4C).

Example 5

Sirt4 Interacts with Mitochondrial Proteins

Figure 5:
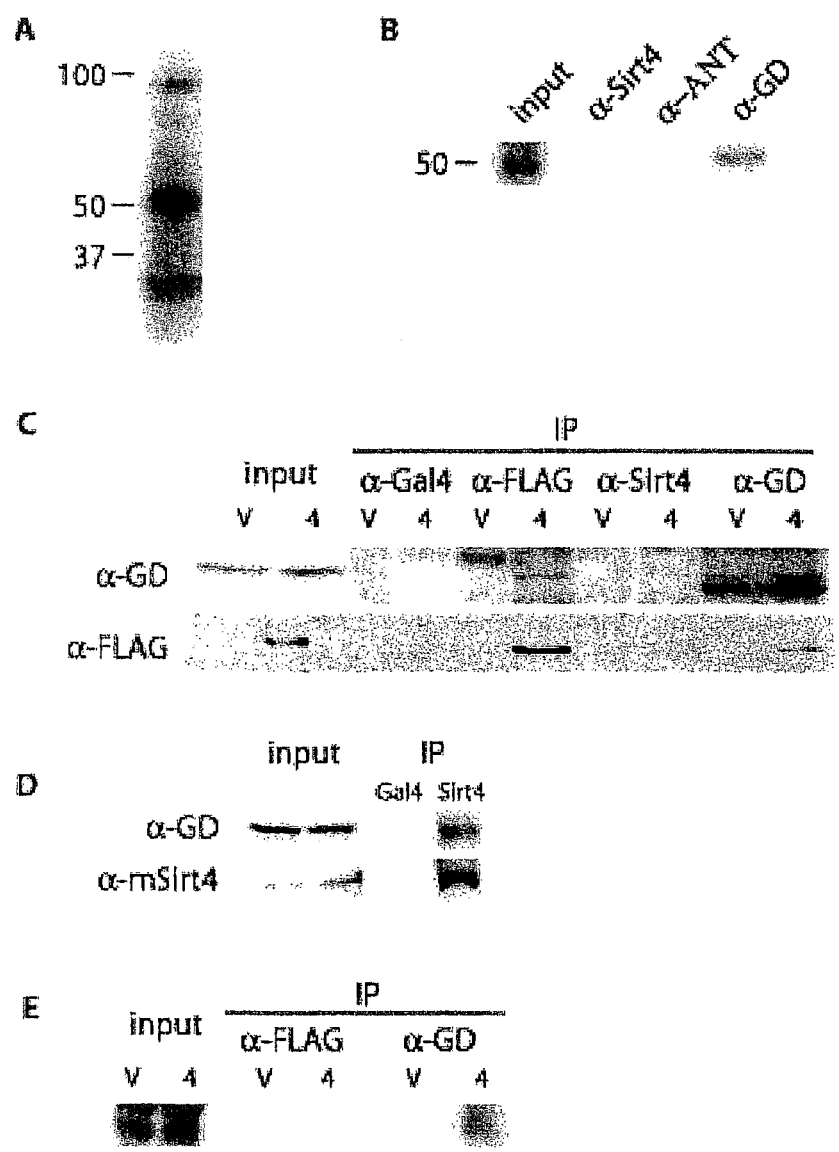
FIG. 5. Glutamate dehydrogenase is ADP-ribosylated in vivo and interacts with Sirt4.

To identify transient, yet biochemically relevant interactions, ADP-ribosylation within the mitochondria was investigated. Isolated mitochondria were incubated with [$^{32}$P]-NAD to identify ADP-ribosylated mitochondrial proteins. In agreement with previous studies (Ziegler (2000) *Eur J Biochem* 267:1550-64), three predominant modified proteins were observed (FIG. 5A), one of which has been identified as glutamate dehydrogenase (GDH) (Herrero-Yraola et al. (2001) *EMBO J* 20:2404-12). Anti-glutamate dehydrogenase immunoprecipitated a 55 kDa-radioactive protein (FIG. 5B). By contrast, immunoprecipitation by antibodies against hSirt4 or the prevalent mitochondrial protein, ANT1 did not give a significant radioactive band that migrated at 55 kDa.

The interaction between Sirt4 and mitochondrial proteins in 293T cells that overexpressed hSirt4-FLAG was investigated. Immunoprecipitations using α-FLAG antibodies isolated a complex between Sirt4-FLAG and glutamate dehydrogenase (GDH), insulin degrading enzyme (IDE), and adenine nucleotide transporter (ANT) in Sirt4 overexpressing cells, but not control cells (FIG. 5C). The complex between Sirt4-FLAG and GDH was also be identified by immunoprecipitation with α-glutamate dehydrogenase antibodies (FIG. 5C).

MIN6 cells were used to investigate the endogenous interaction between Sirt4 and GDH, IDE, and ANT. Sirt4 was immunoprecipitated from MIN6 cells using the C-terminal antibody, and the blots were probed with antibodies against GDH, IDE, and ANT. Sirt4 was able to form an endogenous complex with glutamate dehydrogenase (FIG. 5D), insulin degrading enzyme, and adenine nucleotide transporter in MIN6 cells. These results indicate that Sirt4 can form a complex with each of GDH, IDE, and ANT under physiological protein concentrations.

Mitochondria from 293T control or Sirt4-FLAG overexpressing cells were incubated with [$^{32}$P]-NAD, and the ADP-ribosylation state of glutamate dehydrogenase was measured by immunoprecipitation and subsequent autoradiography. Sirt4 overexpression enhanced the ADP-ribosylation of glutamate dehydrogenase (FIG. 5E). Moreover, a small amount of labeled glutamate dehydrogenase could be detected in a complex with Sirt4 (FIG. 5E).

It is believed that the Sirt4 may act in β-cells to control insulin levels by interactions with all of GDH, ANT, and IDE.

Example 6

Sirt4 Inhibits Glutamate Dehydrogenase Activity

Figure 6A:
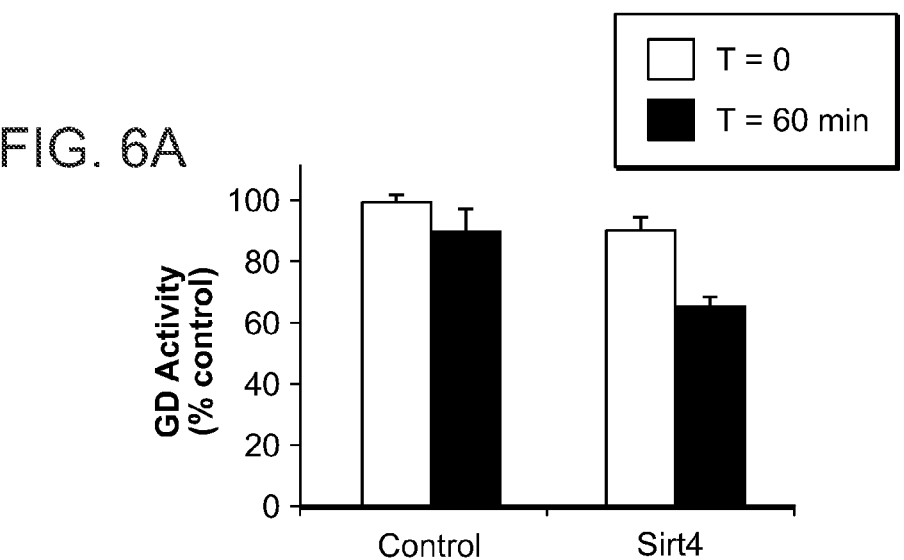
FIG. 6A. The enzymatic activity of glutamate dehydrogenase (50 mg in 200 ml) was measured before (open bars, T=0) after a 60 min incubation (filled bars, T=60) at 37° C. with hSirt4-FLAG (50 ng) or a buffer control in the presence of 1 mM NAD+. Experiments were replicated 3-5 times.
Figure 6B:
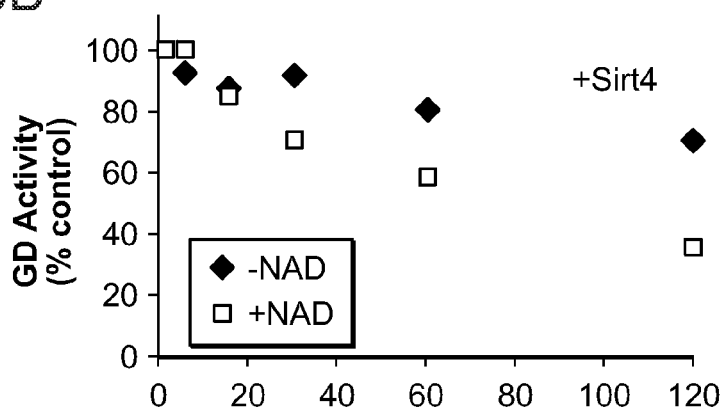
FIG. 6B. Inhibition of glutamate dehydrogenase by Sirt4 requires 1 mM NAD+. Glutamate dehydrogenase (50 mg) was incubated with Sirt4 at 37° C. in the presence (pink) or absence (blue) of 1 mM NAD+. Aliquots (1 ml) were removed at T=0, 5, 15, 30, 60, or 120 min, and glutamate dehydrogenase activity was measured for each time point.
Figure 6C:
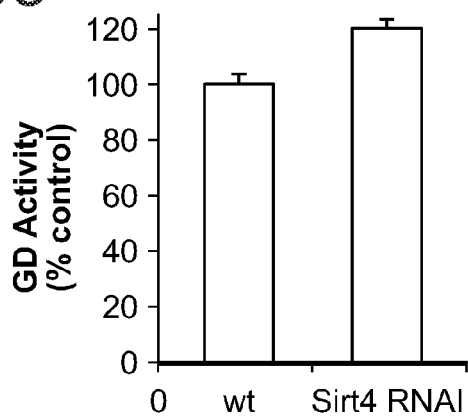
FIG. 6C. The activity of glutamate dehydrogenase was measure in mitochondrial lysates (30 mg) from control or Sirt4 RNAi cells. Experiments were performed 3-5 times using cell lines from two separate infections.

Sirt4 or a buffer control was incubated with bovine recombinant glutamate dehydrogenase for one hour in the presence of NAD. Then, the glutamate dehydrogenase activity was assessed by monitoring the disappearance of NADH ($A_{340}$). Sirt4, but not the buffer control, significantly reduced the enzymatic activity of glutamate dehydrogenase. To verify that this inhibition was dependent on the availability of NAD$^+$, we incubated Sirt4 with or without NAD$^+$ with glutamate dehydrogenase for various times. Sirt4 inhibited glutamate dehydrogenase activity only in the presence of NAD' (FIG. 6B), and within 2 hours the activity of glutamate dehydrogenase was inhibited by 50%. After incubating for 12 hours, the activity of glutamate dehydrogenase was inhibited by more than 90%.

Figure 7:
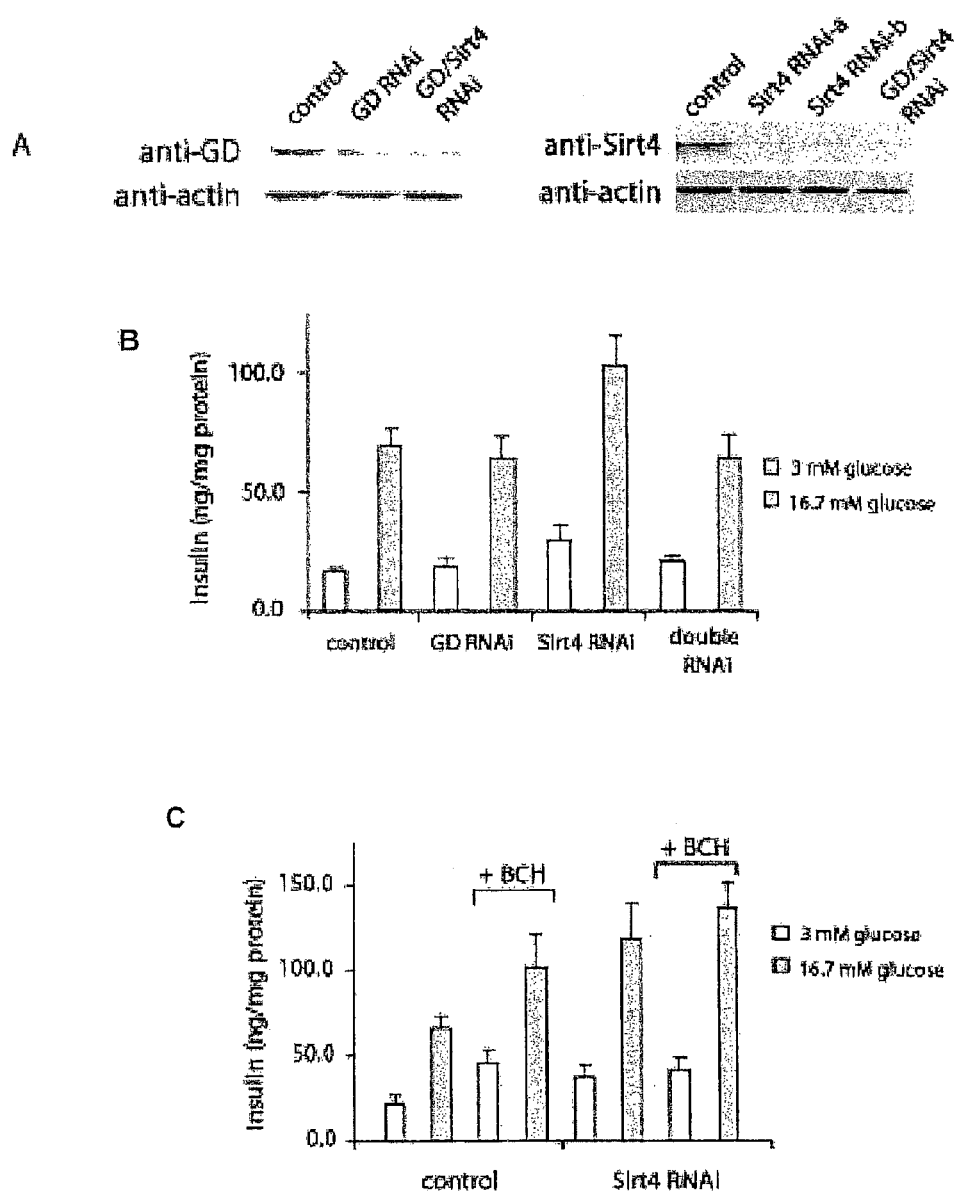
FIG. 7. Elevated glutamate dehydrogenase activity contributes to increased insulin secretion in Sirt4 RNAi cells.

MIN6 cells were co-infected with RNAi plasmids targeting Sirt4 and glutamate dehydrogenase. Co-infected cells contained less insulin than did Sirt4-RNAi cells (FIG. 7A), indicating that elevated glutamate dehydrogenase activity could account for the increase in insulin secreted. To test further whether glutamate dehydrogenase activity was altered in Sirt4 RNAi cells, insulin secretion assays were performed in the presence and absence of a glutamate dehydrogenase activator, BCH, which is known to stimulate insulin secretion. Control cells that were stimulated with both BCH and 16.7 mM glucose demonstrated enhanced insulin secretion when compared to cells stimulated with 16.7 mM glucose alone (FIG. 7B). Sirt4 RNAi treated cells did not secrete more insulin when incubated with BCH and 16.7 mM glucose when compared to the 16.7 mM glucose condition, indicating that glutamate dehydrogenase activity may be already elevated in these cells. Finally, the activity of glutamate dehydrogenase from purified mitochondria isolated from normal or Sirt4 RNAi treated cells was measured. A 20% increase in the enzymatic activity of glutamate dehydrogenase in the Sirt4 RNAi treated cells was found (FIG. 7C). Taken together, these data show that a decrease in the levels of Sirt4 leads to a functional gain in glutamate dehydrogenase activity.

Example 7

Sirt4 Function in β-cell Energetics

Figure 8A:
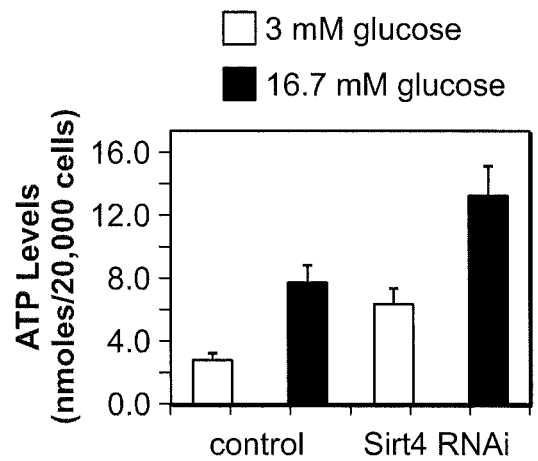
FIG. 8A. Total cellular ATP was measured in 20,000 control or Sirt4 RNAi MIN6 cells. ATP was measure after incubation in 3 (open bars) or 16.7 mM (filled bars) glucose as described for insulin secretion assays.

To explore the mechanism of how Sirt4 and glutamate dehydrogenase regulate insulin secretion from pancreatic β-cells, two parameters regulated by the mitochondria and change upon glucose stimulation were measured: ATP concentration and oxygen consumption. As expected, control cells showed an increase in ATP content when shifted from 3 to 16.7 mM glucose (FIG. 8A). Sirt4 RNAi treated cells demonstrated a significant increase in ATP content in both 3 and 16.7 mM glucose concentrations, as compared to control cells. These cells still produced more ATP when stimulated with 16.7 mM glucose, indicating that their glucose metabolism was intact.

Figure 8B:
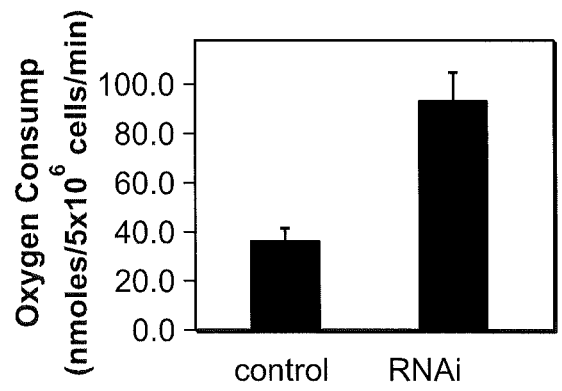
FIG. 8B. Oxygen consumption was measured using a Clark electrode in control or Sirt4 RNAi treated cells that were incubated in 16.7 mM glucose.

Oxygen consumption is another measure of the cell's metabolic state and will increase with glucose stimulation. The reduction of Sirt4 levels caused cells to consume 2-fold more oxygen in 16.7 mM glucose than the control cells (FIG. 8B). As both ATP level and rate of oxygen consumption increased in Sirt4-RNAi cells, their metabolic rate is up-regulated in a coupled process.

Example 8

Determination of Putative Regulatory Sequences for SIRT4

Figure 9:
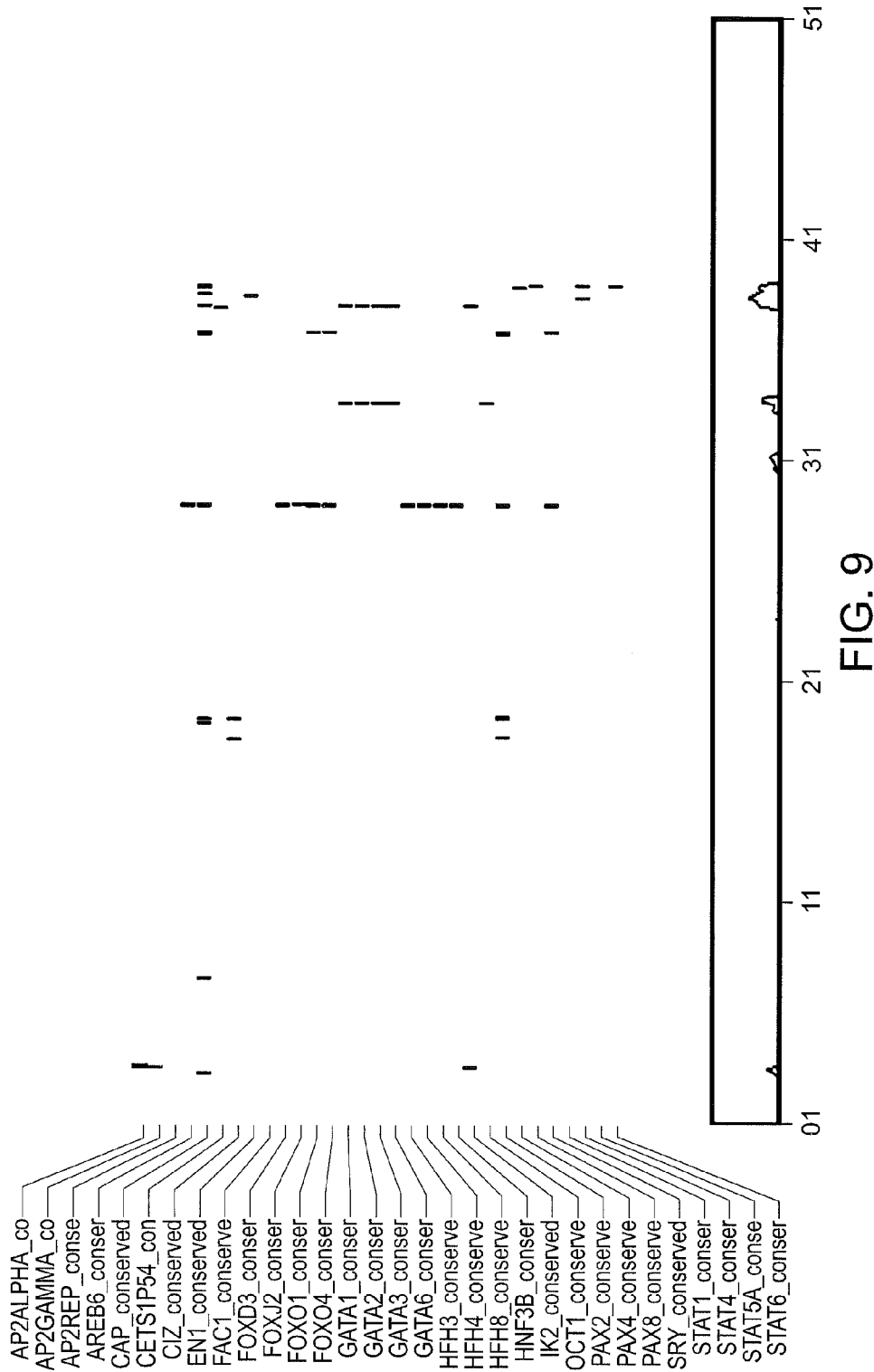
FIG. 9 is a graphical overview of conserved putative transcription factor binding sites in the region 5 kb upstream of human and mouse Sirt4 as determined using the rVISTA program. Tick marks represent conserved binding sites. Predicted transcription factors are indicated on the left. Percent identity between the sequences is indicated on the bottom graph.

To determine conserved putative transcription factor binding sites involved in the regulation of Sirt4, genomic sequences 5 kb upstream of the start of the first codon of human and mouse Sirt4 were input to the rVISTA™ program (Loots et al. (2002) Genome. Res. 12:832-839). The output of the program is shown in FIG. 9.

All patents, patent applications, and references cited herein are hereby incorporated by reference in their entirety. Other embodiments are within the scope of the following claims.

What is claimed is:

1. A method of modulating insulin secretion in response to glucose, comprising administering an agent to modulate the expression or activity of Sirt4 in an insulin-secreting cell.

2. The method of claim 1, wherein insulin secretion is increased by decreasing the expression or activity of Sirt4.

3. The method of claim 1, wherein insulin secretion is decreased by increasing the expression or activity of Sirt4.

4. The method of claim 1, wherein insulin secretion is modulated in vitro.

5. The method of claim 1, wherein insulin secretion is modulated in a subject.

6. A method of treating a metabolic disorder, comprising administering to a subject an agent that modulates the expression or activity of Sirt4 in an amount effective to treat the metabolic disorder.

7. The method of claim 6, wherein the metabolic disorder includes at least one of diabetes, insulin resistance, metabolic syndrome and pre-diabetes.

8. The method of claim 6, wherein the levels of Sirt4 are modulated in an insulin-secreting cell.

9. The method of claim 6, wherein the agent is an antagonistic nucleic acid that reduces Sirt4 expression.

10. The method of claim 6, wherein the agent comprises an siRNA that targets Sirt4 mRNA.

11. A method of treating a symptom of a neurodegenerative disorder, comprising administering to a subject a compound that increases the expression or activity of Sirt4 in an amount effective to treat the neurodegenerative disorder.

12. The method of claim 11, wherein the neurodegenerative disorder involves accumulation of β-amyloid peptide.

13. The method of claim 11, wherein the neurodegenerative disorder is Alzheimer's disease.

* * * * *

SEQUENCE LISTING

<160> NUMBER OF SEQ ID NOS: 11

<210> SEQ ID NO 1
<211> LENGTH: 314
<212> TYPE: PRT
<213> ORGANISM: Homo Sapiens

```
<400> SEQUENCE: 1

Met Lys Met Ser Phe Ala Leu Thr Phe Arg Ser Ala Lys Gly Arg Trp
 1               5                  10                  15

Ile Ala Asn Pro Ser Gln Pro Cys Ser Lys Ala Ser Ile Gly Leu Phe
            20                  25                  30

Val Pro Ala Ser Pro Pro Leu Asp Pro Glu Lys Val Lys Glu Leu Gln
        35                  40                  45

Arg Phe Ile Thr Leu Ser Lys Arg Leu Leu Val Met Thr Gly Ala Gly
    50                  55                  60

Ile Ser Thr Glu Ser Gly Ile Pro Asp Tyr Arg Ser Glu Lys Val Gly
65                  70                  75                  80

Leu Tyr Ala Arg Thr Asp Arg Arg Pro Ile Gln His Gly Asp Phe Val
                85                  90                  95

Arg Ser Ala Pro Ile Arg Gln Arg Tyr Trp Ala Arg Asn Phe Val Gly
            100                 105                 110

Trp Pro Gln Phe Ser Ser His Gln Pro Asn Pro Ala His Trp Ala Leu
        115                 120                 125

Ser Thr Trp Glu Lys Leu Gly Lys Leu Tyr Trp Leu Val Thr Gln Asn
    130                 135                 140

Val Asp Ala Leu His Thr Lys Ala Gly Ser Arg Arg Leu Thr Glu Leu
145                 150                 155                 160

His Gly Cys Met Asp Arg Val Leu Cys Leu Asp Cys Gly Glu Gln Thr
                165                 170                 175

Pro Arg Gly Val Leu Gln Glu Arg Phe Gln Val Leu Asn Pro Thr Trp
            180                 185                 190

Ser Ala Glu Ala His Gly Leu Ala Pro Asp Gly Asp Val Phe Leu Ser
        195                 200                 205

Glu Glu Gln Val Arg Ser Phe Gln Val Pro Thr Cys Val Gln Cys Gly
    210                 215                 220

Gly His Leu Lys Pro Asp Val Val Phe Phe Gly Asp Thr Val Asn Pro
225                 230                 235                 240

Asp Lys Val Asp Phe Val His Lys Arg Val Lys Glu Ala Asp Ser Leu
                245                 250                 255

Leu Val Val Gly Ser Ser Leu Gln Val Tyr Ser Gly Tyr Arg Phe Ile
            260                 265                 270

Leu Thr Ala Trp Glu Lys Lys Leu Pro Ile Ala Ile Leu Asn Ile Gly
        275                 280                 285

Pro Thr Arg Ser Asp Asp Leu Ala Cys Leu Lys Leu Asn Ser Arg Cys
    290                 295                 300

Gly Glu Leu Leu Pro Leu Ile Asp Pro Cys
305                 310

<210> SEQ ID NO 2
<211> LENGTH: 333
<212> TYPE: PRT
<213> ORGANISM: Mus Musculus

<400> SEQUENCE: 2

Met Ser Gly Leu Thr Phe Arg Pro Thr Lys Gly Arg Trp Ile Thr His
 1               5                  10                  15

Leu Ser Arg Pro Arg Ser Cys Gly Pro Ser Gly Leu Phe Val Pro Pro
            20                  25                  30

Ser Pro Pro Leu Asp Pro Glu Lys Ile Lys Glu Leu Gln Arg Phe Ile
        35                  40                  45

Ser Leu Ser Lys Lys Leu Leu Val Met Thr Gly Ala Gly Ile Ser Thr
```

```
             50                  55                  60
Glu Ser Ser Ile Pro Asp Tyr Arg Ser Glu Lys Val Gly Leu Tyr Ala
 65                  70                  75                  80

Arg Thr Asp Arg Arg Pro Ile Gln His Ile Asp Phe Val Arg Ser Ala
                 85                  90                  95

Pro Val Arg Gln Arg Tyr Trp Ala Arg Asn Phe Val Gly Trp Pro Gln
            100                 105                 110

Phe Ser Ser His Gln Pro Asn Pro Ala His Trp Ala Leu Ser Asn Trp
        115                 120                 125

Glu Arg Leu Gly Lys Leu His Trp Leu Val Thr Gln Asn Val Asp Ala
    130                 135                 140

Leu His Ser Lys Ala Gly Ser Gln Arg Leu Thr Glu Leu His Gly Cys
145                 150                 155                 160

Met His Arg Val Leu Cys Leu Asn Cys Gly Glu Gln Thr Ala Arg Arg
                165                 170                 175

Val Leu Gln Glu Arg Phe Gln Ala Leu Asn Pro Ser Trp Ser Ala Glu
            180                 185                 190

Ala Gln Gly Val Ala Pro Asp Gly Asp Val Phe Leu Thr Glu Glu Gln
        195                 200                 205

Val Arg Ser Phe Gln Val Pro Cys Cys Asp Arg Cys Gly Gly Pro Leu
    210                 215                 220

Lys Pro Asp Val Val Phe Phe Gly Asp Thr Val Asn Pro Asp Lys Val
225                 230                 235                 240

Asp Phe Val His Arg Arg Val Lys Glu Ala Asp Ser Leu Leu Val Val
                245                 250                 255

Gly Ser Ser Leu Gln Val Tyr Ser Gly Tyr Arg Phe Ile Leu Thr Ala
            260                 265                 270

Arg Glu Gln Lys Leu Pro Ile Ala Ile Leu Asn Ile Gly Pro Thr Arg
        275                 280                 285

Ser Asp Asp Leu Ala Cys Leu Lys Leu Asp Ser Arg Cys Gly Glu Leu
    290                 295                 300

Leu Pro Leu Ile Asp Pro Arg Arg Gln His Ser Asp Val Gln Arg Leu
305                 310                 315                 320

Glu Met Asn Phe Pro Leu Ser Ser Ala Ala Gln Asp Pro
                325                 330

<210> SEQ ID NO 3
<211> LENGTH: 262
<212> TYPE: PRT
<213> ORGANISM: Homo Sapiens

<400> SEQUENCE: 3

Leu Gln Arg Phe Ile Thr Leu Ser Lys Arg Leu Leu Val Met Thr Gly
  1               5                  10                  15

Ala Gly Ile Ser Thr Glu Ser Gly Ile Pro Asp Tyr Arg Ser Glu Lys
             20                  25                  30

Val Gly Leu Tyr Ala Arg Thr Asp Arg Arg Pro Ile Gln His Gly Asp
         35                  40                  45

Phe Val Arg Ser Ala Pro Ile Arg Gln Arg Tyr Trp Ala Arg Asn Phe
     50                  55                  60

Val Gly Trp Pro Gln Phe Ser Ser His Gln Pro Asn Pro Ala His Trp
 65                  70                  75                  80

Ala Leu Ser Thr Trp Glu Lys Leu Gly Lys Leu Tyr Trp Leu Val Thr
                 85                  90                  95

Gln Asn Val Asp Ala Leu His Thr Lys Ala Gly Ser Arg Arg Leu Thr
```

```
                        100                 105                 110
Glu Leu His Gly Cys Met Asp Arg Val Leu Cys Leu Asp Cys Gly Glu
        115                 120                 125

Gln Thr Pro Arg Gly Val Leu Gln Glu Arg Phe Gln Val Leu Asn Pro
    130                 135                 140

Thr Trp Ser Ala Glu Ala His Gly Leu Ala Pro Asp Gly Asp Val Phe
145                 150                 155                 160

Leu Ser Glu Glu Gln Val Arg Ser Phe Gln Val Pro Thr Cys Val Gln
                165                 170                 175

Cys Gly His Leu Lys Pro Asp Val Val Phe Phe Gly Asp Thr Val
            180                 185                 190

Asn Pro Asp Lys Val Asp Phe Val His Lys Arg Val Lys Glu Ala Asp
        195                 200                 205

Ser Leu Leu Val Val Gly Ser Ser Leu Gln Val Tyr Ser Gly Tyr Arg
    210                 215                 220

Phe Ile Leu Thr Ala Trp Glu Lys Lys Leu Pro Ile Ala Ile Leu Asn
225                 230                 235                 240

Ile Gly Pro Thr Arg Ser Asp Asp Leu Ala Cys Leu Lys Leu Asn Ser
                245                 250                 255

Arg Cys Gly Glu Leu Leu
            260

<210> SEQ ID NO 4
<211> LENGTH: 45
<212> TYPE: DNA
<213> ORGANISM: Artificial Sequence
<220> FEATURE:
<223> OTHER INFORMATION: Primer

<400> SEQUENCE: 4
caccgcggtg gcggccgcat gaagatgagc tttgcgttga ctttc         45

<210> SEQ ID NO 5
<211> LENGTH: 37
<212> TYPE: DNA
<213> ORGANISM: Artificial Sequence
<220> FEATURE:
<223> OTHER INFORMATION: Primer

<400> SEQUENCE: 5
cttgtaatcc tcgaggcatg ggtctatcaa aggcagc               37

<210> SEQ ID NO 6
<211> LENGTH: 40
<212> TYPE: DNA
<213> ORGANISM: Artificial Sequence
<220> FEATURE:
<223> OTHER INFORMATION: Primer

<400> SEQUENCE: 6
cttgtaatcc tcgagtcagc atgggtctat caaaggcagc            40

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
cgcttccaag ccctgaacc                                   19
```

```
<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ggagagttgc tgcctttaa                                                    19

<210> SEQ ID NO 9
<211> LENGTH: 14
<212> TYPE: PRT
<213> ORGANISM: Mus Musculus

<400> SEQUENCE: 9

Leu Glu Met Asn Phe Pro Leu Ser Ser Ala Ala Gln Asp Pro
1               5                   10

<210> SEQ ID NO 10
<211> LENGTH: 30
<212> TYPE: PRT
<213> ORGANISM: Homo Sapiens

<400> SEQUENCE: 10

Met Ala Phe Trp Gly Trp Arg Ala Ala Ala Leu Arg Leu Trp Gly
1               5                   10                  15

Arg Val Val Glu Arg Val Glu Ala Gly Gly Val Gly Pro
            20                  25                  30

<210> SEQ ID NO 11
<211> LENGTH: 32
<212> TYPE: PRT
<213> ORGANISM: Homo Sapiens

<400> SEQUENCE: 11

Met Lys Met Ser Phe Ala Leu Thr Phe Arg Ser Ala Lys Gly Arg Trp
1               5                   10                  15

Ile Ala Asn Pro Ser Gln Pro Cys Ser Lys Ala Ser Ile Gly Leu Phe
            20                  25                  30
```